(12) United States Patent
Gao et al.

(10) Patent No.: US 10,836,775 B2
(45) Date of Patent: Nov. 17, 2020

(54) 6,6-FUSED HETEROARYL PIPERIDINE ETHER ALLOSTERIC MODULATORS OF THE M4 MUSCARINIC ACETYLCHOLINE RECEPTOR

(71) Applicants: Merck Sharp & Dohme Corp., Rahway, NJ (US); Xiaolei Gao, Bridgewater, NJ (US); Sandra L. Knowles, Princeton, NJ (US); Chunsing Li, Shanghai (CN); Michael Man-Chu Lo, Bedminster, NJ (US); Robert D. Mazzola, Jr., Stewartsville, NJ (US); Ling Tong, Warren, NJ (US)

(72) Inventors: Xiaolei Gao, Bridgewater, NJ (US); Sandra L. Knowles, Princeton, NJ (US); Chunsing Li, Shanghai (CN); Michael Man-Chu Lo, Bedminster, NJ (US); Robert D. Mazzola, Jr., Stewartsville, NJ (US); Ling Tong, Warren, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/471,675

(22) PCT Filed: Dec. 18, 2017

(86) PCT No.: PCT/US2017/066918
§ 371 (c)(1),
(2) Date: Jun. 20, 2019

(87) PCT Pub. No.: WO2018/118735
PCT Pub. Date: Jun. 28, 2018

(65) Prior Publication Data
US 2019/0315762 A1 Oct. 17, 2019

(30) Foreign Application Priority Data
Dec. 22, 2016 (WO) ................ PCT/CN2016/111529

(51) Int. Cl.
C07D 491/052 (2006.01)
C07D 471/04 (2006.01)
C07D 491/048 (2006.01)
C07D 498/04 (2006.01)

(52) U.S. Cl.
CPC ....... *C07D 491/052* (2013.01); *C07D 471/04* (2013.01); *C07D 491/048* (2013.01); *C07D 498/04* (2013.01)

(58) Field of Classification Search
CPC .................................................. C07D 491/052
See application file for complete search history.

(56) References Cited

U.S. PATENT DOCUMENTS

| 5,574,044 | A | 11/1996 | Thompson et al. |
| 5,691,323 | A | 11/1997 | Thompson et al. |
| 6,699,880 | B1 | 3/2004 | Yamakawa et al. |
| 6,900,224 | B2 | 5/2005 | Ledoussal et al. |
| 7,074,801 | B1 | 7/2006 | Yoshida et al. |
| 7,858,635 | B2 | 12/2010 | Makings et al. |
| 7,964,602 | B2 | 6/2011 | MacDonald et al. |
| 8,071,776 | B2 | 12/2011 | Rubio Esteban et al. |
| 8,168,639 | B2 | 5/2012 | Kogan |
| 8,349,850 | B2 | 1/2013 | Tworowski et al. |
| 8,614,319 | B2 | 12/2013 | Tworowski et al. |
| 9,034,872 | B2 | 5/2015 | Tworowski et al. |
| 9,056,875 | B2 | 6/2015 | Lindsley et al. |
| 9,056,876 | B2 | 6/2015 | Conn et al. |
| 9,493,481 | B2 | 11/2016 | Lindsley et al. |
| 9,593,106 | B2 | 3/2017 | Livermore et al. |
| 9,637,498 | B2 | 5/2017 | Lindsley et al. |
| 9,670,183 | B2 | 6/2017 | Brown et al. |
| 9,758,506 | B2 | 9/2017 | Brown et al. |
| 9,868,746 | B2 | 1/2018 | Lindsley et al. |
| 10,329,289 | B2 | 6/2019 | Bao et al. |
| 10,351,564 | B2 | 7/2019 | Gao et al. |
| 10,512,638 | B2 | 12/2019 | Rudd et al. |
| 2007/0004763 | A1 | 1/2007 | Baindur et al. |
| 2008/0306107 | A1 | 12/2008 | Griffin et al. |
| 2009/0247584 | A1 | 10/2009 | Holzemann |
| 2016/0200733 | A1 | 7/2016 | Lindsley et al. |
| 2017/0096437 | A1 | 4/2017 | Congreve et al. |
| 2017/0369505 | A1 | 12/2017 | Lindsley et al. |

FOREIGN PATENT DOCUMENTS

| CN | 105073729 | 11/2015 |
| JP | 2013237634 | 11/2013 |
| JP | 2014047192 | 3/2014 |
| JP | 2014062063 | 4/2014 |
| WO | WO1998006697 | 2/1998 |
| WO | WO1999032481 | 7/1999 |
| WO | 2005042542 A1 | 5/2005 |
| WO | WO2005100351 | 10/2005 |
| WO | WO2006125180 | 11/2006 |
| WO | WO2006135649 | 12/2006 |

(Continued)

OTHER PUBLICATIONS

Online: "http://www.chembridge.com/screening_librarires/" Jan. 22, 2013.*

(Continued)

*Primary Examiner* — David K O'Dell
(74) *Attorney, Agent, or Firm* — J. Eric Thies; John C. Todaro

(57) ABSTRACT

The present invention is directed to 6,6-fused heteroarylpiperidine ether compounds which are allosteric modulators of the M4 muscarinic acetylcholine receptor. The present invention is also directed to uses of the compounds described herein in the potential treatment or prevention of neurological and psychiatric disorders and diseases in which M4 muscarinic acetylcholine receptors are involved. The present invention is also directed to compositions comprising these compounds. The present invention is also directed to uses of these compositions in the potential prevention or treatment of such diseases in which M4 muscarinic acetylcholine receptors are involved.

13 Claims, No Drawings

(56) References Cited

FOREIGN PATENT DOCUMENTS

| WO | WO2011087776 | | 7/2011 | | |
|---|---|---|---|---|---|
| WO | 2011143495 | A1 | 11/2011 | | |
| WO | WO2011143495 | | 11/2011 | | |
| WO | WO2012020813 | | 2/2012 | | |
| WO | WO2012154731 | | 11/2012 | | |
| WO | WO2013056015 | | 4/2013 | | |
| WO | WO2013122107 | | 8/2013 | | |
| WO | WO2014035829 | | 3/2014 | | |
| WO | WO2014101373 | | 7/2014 | | |
| WO | WO2016147011 | | 9/2016 | | |
| WO | WO2017021728 | | 2/2017 | | |
| WO | WO2017077292 | | 5/2017 | | |
| WO | WO2017107087 | | 6/2017 | | |
| WO | WO-2017107087 | A1 * | 6/2017 | ........... | C07D 471/04 |
| WO | WO2017112556 | | 6/2017 | | |
| WO | WO2017112719 | | 6/2017 | | |

OTHER PUBLICATIONS

Kennedy Synthesis and Structure—Activity Relationships of Allosteric Potentiators of the M4 Muscarinic Acetylcholine Receptor ChemMedChem 2009, 4, 1600-1607.*

Brady "Centrally Active Allosteric Potentiators of the M4 Muscarinic Acetylcholine Receptor Reverse Amphetamine-Induced Hyperlocomotor Activity in Rats" The Journal of Pharmacology and Experimental Therapeutics 2008, vol. 327, No. 3 941-953.*

Foster "Antipsychotic-like Effects of M4 Positive Allosteric Modulators Are Mediated by CB2 Receptor-Dependent Inhibition of Dopamine Release" 2016, Neuron 91, 1244-1252.*

S.P. Carruthers et al. "The muscarinic system, cognition and schizophrenia" Neuroscience and Biobehavioral Reviews 55 (2015) 393-402.*

Bewleu, Blake R., et al., Discovery of a novel, CNS penetrant M4PAM chemotype based on a 6-fluoro-4-(pipenden-1-yl)quinoline-3-carbonitrile core, Bioorganic and Med Chem Letters, 2017, 4274-4279, 27.

Byun, Nellie B, et al., Antipsychotic Drug-like Effects of the Selective M4 Muscarinic Acetylcholine Receptor Positive Allosteric Modulator VU02552100, Neuropsychopharmacology, 2014, 1578-1593, 39.

Eglen, Richard M., Muscarinic receptor ligands and their therapeutic potential, Current Opinion in Chemical Biology, 1999, 426-432, 3.

Kargbo, Robert B., Allosteric Modulators of the M4 Muuscarinic Acetylcholine Receptor, ACS Medicinal Chemistry Letters, 2017, 903-904, 8.

Lindsey, Craig W., et al., Discovery of the mAChR subtype selective M4 positive allosteric modulators, Current Topics in Medicinal Chemistry, 2008, 531, 8-6.

Long, Madeline F., Discovery of a nove 2,4-dimethylquinoline-6-carboxamide M4 positive allosteric modulator (PAM) Chemotype via scaffold hopping, Bioorganic and Med Chem Letters, 2017, 4999-5001, 27.

Melancon, Bruce J., et al., Optimization of M4 Positive Allosteric Modulators (PAMs): The discovery of VUO476406, a non-human primate in vivo tool compound for translational pharmacology, Bioorganic and Med Chem Letters, 2017, 2296-2301, 27.

Salovich, James M., et al., Discovery of N-(4-methoxy-7-methylbenzo[d]thiazol-2-yl) . . . , Bioorganic and Med Chem Letters, 2012, 5084-5088, 22.

Tarr, James C., Challenges in the development of an M4PAM preclinical candidate: The discovery, SAR and in vivo characterization of a . . . , Bioorganic and Med Chem Letters, 2017, 2990-2995, 27.

Tarr, James C., et al., Challenges in the development of an M4PAM Preclinical candidate: . . . , Bioorganic and Med Chem Letters, 2017, 5179-5184, 27.

Utley, Thomas, Synthesis and SAR of a novel metabotropic glutamate receptor 4 . . . , Bioorganic and Med Chem Letters, 2011, 6955-6959, 21.

Wood, Michael R., et al., Discovery and Optimization of a novel series of highly CNS penetrant M4PAMS based on a 5,6-dimethul-4-(piperidin-1-yl)thieno[2,3-d]pyrimidine core, Bioorganic and Med Chem Letters, 2016, 3029-3033, 26.

Wood, Michael R., et al., Discovery of VU0467485/AZ13713945: An M4PAM evaluated as a Preclinical candidate for the Treatment of Schizophrenia, ACS Medicinal Chemistry Letters, 2017, 233-238, 8.

PCT Search Report and Written Opinion for PCT/CN2016/111529 dated Sep. 26, 2017; 9 pages.

PCT Search Report and Written Opinion for PCT/US2017/066918 dated Apr. 6, 2018; 9 pages.

RN: 1552923-38-2 Registry STN American Chemical Society; Feb. 23, 2014.

RN: 1546829-79-1 Registry STN American Chemical Society; Feb. 23, 2014.

RN: 1424588-49-7 Registry STN American Chemical Society; Feb. 23, 2014.

RN:1394484-56-0 Registry STN American Chemical Society; Feb. 23, 2014.

PUBCHEM Substance Record for SID 215465399 dated Oct. 20, 2014.

European Search Report, Application EP178853685, dated Jun. 2, 2020, 7 pages.

* cited by examiner

6,6-FUSED HETEROARYL PIPERIDINE ETHER ALLOSTERIC MODULATORS OF THE M4 MUSCARINIC ACETYLCHOLINE RECEPTOR

CROSS REFERENCE TO RELATED APPLICATIONS

This application is a U.S. National Phase application under 35 U.S.C. § 371 of PCT Application No. PCT/US2017/066918, filed Dec. 18, 2017, which claims priority under 35 U.S.C. § 119(e) from PCT/CN2016/111529, filed Dec. 22, 2016.

BACKGROUND OF THE INVENTION

Acetylcholine (ACh) is a key neurotransmitter that modulates neuronal function in the peripheral nervous system (PNS) and central nervous system (CNS). ACh mediates its actions via two families of receptors, termed the muscarinic ACh receptors (mAChRs) and the nicotinic ACh receptors (nAChRs). A large body of evidence suggests that basal forebrain cholinergic neurons and basalo-cortical cholinergic pathways are selectively vulnerable to degeneration in Alzheimer's disease. It has therefore been hypothesized that cholinergic hypofunction contributes to the cognitive deficits of patients suffering from Alzheimer's disease. Consequently, acetylcholinesterase inhibitors, which inhibit ACh hydrolysis and potentiate cholinergic signaling have been demonstrated to not only provide improvements in cognitive symptoms associated with Alzheimer's disease, but also show efficacy in treating the psychiatric symptoms. Acetylcholinesterase inhibitors, however, have not been shown to change the underlying disease pathology.

Another potential pharmacotherapeutic target to counteract cholinergic hypofunction is the activation of muscarinic acetylcholine receptors (mAChRs). Muscarinic acetylcholine receptors are members of the G protein-coupled receptor superfamily which mediate the actions of the neurotransmitter acetylcholine in both the central and peripheral nervous system. Muscarinic acetylcholine receptors are prevalent throughout the body and five distinct muscarinic receptors (M1-M5) have been identified in mammals. The muscarinic receptors are known to contain one or more allosteric sites which may alter the affinity with which muscarinic ligands bind to the primary binding or orthosteric sites. In the central nervous system, muscarinic receptors are involved in cognitive, behavior, sensory, motor and autonomic functions. The M4 muscarinic acetylcholine receptor is predominantly expressed in the striatum, but also in the hippocampus and cortex.

Muscarinic receptors in the central nervous system play a critical role in mediating higher cognitive processing and control of dopamine release. Administration of nonselective muscarinic antagonists can induce cognitive deficits and psychosis in humans suggesting that mAChR activation may provide pro-cognitive and antipsychotic efficacy. Accordingly, several mAChR agonists have been developed and entered clinical studies for the treatment of cognitive and psychiatric symptoms associated with Alzheimer's and neuropsychiatric diseases such as schizophrenia. (Carruthers, Neuroscience & Biobehavioral Rev., 2015, 55: 393-402; Jones, et al. Neuropsychopharmacology, 2012, 37: 16-42). One of these, the M1/M4 preferring mAChR agonist xanomeline was assessed in patients with Alzheimer's disease, and while showing a trend for improving cognitive deficits, did produce robust and dose-dependent reductions in hallucinations, delusions, vocal outbursts, and other behavioral disturbances in these patients. A subsequent study in patients with schizophrenia demonstrated that xanomeline produced robust improvements in positive, negative and cognitive symptoms. (Bodick, et al., Arch Neurol. 1997; 54: 465-73). Xanomeline, in addition to other mAChR agonists have been demonstrated to produce robust antipsychotic-like effects in a number of preclinical paradigms. For instance, xanomeline, reverses a number of dopamine driven behaviors, including amphetamine induced locomotion in rats, apomorphine induced climbing in mice, dopamine agonist driven turning in unilateral 6-OH-DA lesioned rats and amphetamine induced motor unrest in monkeys (without EPS liability). It also has been shown to inhibit A10, but not A9, dopamine cell firing and conditioned avoidance and induces c-fos expression in prefrontal cortex and nucleus accumbens, but not in striatum in rats. These data are all suggestive of an atypical antipsychotic-like profile. Subsequent studies with M4 knockout mice have demonstrated that the antipsychotic-like effects of xanomeline are mediated by the M4 receptor. Despite these promising clinical and preclinical effects, xanomeline, like other muscarinic agonists, ultimately failed in clinical development due to lack of adequate receptor subtype selectivity resulting in dose-limiting side effects including disturbed gastrointestinal motility, bradycardia, nausea and vomiting.

The development of selective M4 positive allosteric modulators (PAMs) is a strategy to overcome the challenges of developing selective orthosteric muscarinic agonists. Indeed, studies with M4 PAMs have shown that selective activation of M4 mAChRs can reverse both hyperdopaminergic and hypoglutamatergic behaviors in preclinical models. Accordingly, the compounds of the present invention, which are allosteric modulators of the M4 muscarinic acetylcholine receptor, are believed to be useful in the treatment of Alzheimer's disease and other diseases mediated by the muscarinic M4 muscarinic acetylcholine receptor.

SUMMARY OF THE INVENTION

The present invention is directed to 6,6-fused heteroarylpiperidine ether compounds which are allosteric modulators of the M4 muscarinic acetylcholine receptor. The present invention is also directed to uses of the compounds described herein in the potential treatment or prevention of neurological and psychiatric disorders and diseases in which M4 muscarinic acetylcholine receptors are involved. The present invention is also directed to compositions comprising these compounds. The present invention is also directed to uses of these compositions in the potential prevention or treatment of such diseases in which M4 muscarinic acetylcholine receptors are involved.

DETAILED DESCRIPTION OF THE INVENTION

The present invention is directed to compounds of the formula I:

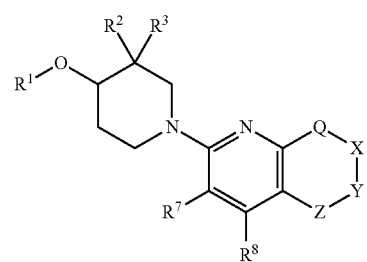

wherein:
Q is selected from the group consisting of:
- (1) —O—,
- (2) =N—,
- (3) —NR$^9$—,
- (4) —(C=O)—,
- (5) —(CHR$^{10}$)—, and
- (6) =(CR$^{10}$)—;

X is selected from the group consisting of:
- (1) =N—,
- (2) —NR$^9$—,
- (3) —(C=O)—,
- (4) —(C=NH)—,
- (5) —(CHR$^{11}$)—, and
- (6) =(CR$^{11}$)—;

Y is selected from the group consisting of:
- (1) —O—,
- (2) =N—,
- (3) —NR$^9$—,
- (4) —(C=O)—,
- (5) —(CHR$^{12}$)—, and
- (6) =(CR$^{12}$)—;

Z is selected from the group consisting of:
- (1) —(C=O)—,
- (2) —(CHR$^{10}$)—, and
- (3) =(CR$^{10}$)—;

R$^1$ is selected from the group consisting of:
- (1) —C$_{1-6}$alkyl, which is unsubstituted or substituted with substituents selected from the group consisting of: hydroxy, fluoro, —CN, —O—C$_{1-6}$alkyl, and C$_{3-6}$cycloalkyl;
- (2) a phenyl, heteroaryl or heterocyclyl ring, wherein the phenyl, heteroaryl or heterocyclyl ring is substituted with one or more R$^{1a}$, R$^{1b}$ and R$^{1c}$, wherein R$^{1a}$, R$^{1b}$ and R$^{1c}$ are independently selected from the group consisting of:
  - (a) hydrogen,
  - (b) halogen,
  - (c) C$_{1-6}$alkyl, which is unsubstituted or substituted with substituents selected from the group consisting of: hydroxy and fluoro,
  - (d) —O—C$_{1-6}$alkyl,
  - (e) C$_{3-6}$cycloalkyl, and
  - (f) —CN;

R$^2$ and R$^3$ are independently selected from the group consisting of:
- (1) hydrogen, and
- (2) fluoro;

R$^7$ and R$^8$ are independently selected from the group consisting of:
- (1) hydrogen, and
- (2) C$_{1-6}$alkyl;

R$^9$ is selected from the group consisting of:
- (1) hydrogen,
- (2) —C$_{1-6}$alkyl, which is unsubstituted or substituted with substituents selected from the group consisting of: hydroxy, methoxy, fluoro, phenyl, or pyridyl;

each of R$^{10}$, R$^{11}$ and R$^{12}$ is independently selected from the group consisting of:
- (1) hydrogen,
- (2) fluoro,
- (3) —OH,
- (4) —CH$_3$,
- (5) —CF$_3$,
- (6) —CH$_2$OH,
- (7) —CH$_2$CH$_2$OH,
- (8) —CH$_2$OCH$_3$, and
- (9) —CH$_2$CH$_2$OCH$_3$;

or a pharmaceutically acceptable salt thereof.

An embodiment of the present invention includes compounds of the formula Ia:

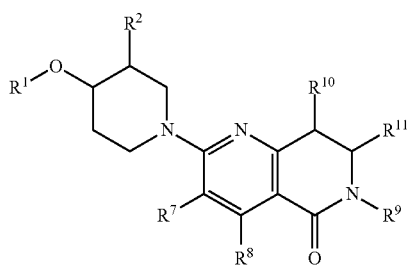

Ia wherein R$^1$, R$^2$, R$^7$, R$^8$, R$^{10}$ and R$^{11}$ are defined herein; or a pharmaceutically acceptable salt thereof.

An embodiment of the present invention includes compounds of the formula Ib:

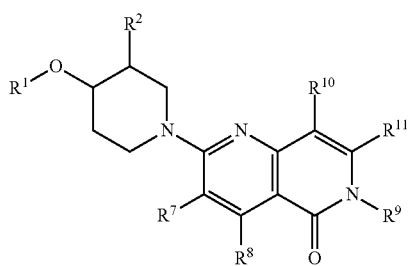

II wherein R$^1$, R$^2$, R$^7$, R$^8$, R$^{10}$ and R$^{11}$ are defined herein; or a pharmaceutically acceptable salt thereof.

An embodiment of the present invention includes compounds of the formula Ic:

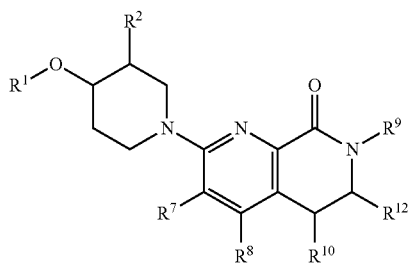

Ic wherein R$^1$, R$^2$, R$^7$, R$^8$, R$^{10}$, R$^{11}$ and R$^{12}$ are defined herein; or a pharmaceutically acceptable salt thereof.

An embodiment of the present invention includes compounds of the formula Id:

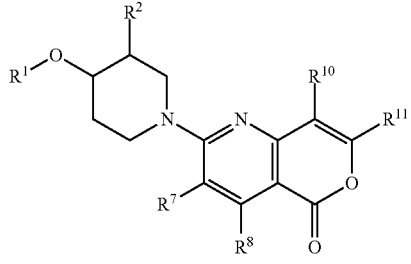

Id wherein R$^1$, R$^2$, R$^7$, R$^8$, R$^{10}$ and R$^{11}$ are defined herein; or a pharmaceutically acceptable salt thereof.

An embodiment of the present invention includes compounds of the formula Ie:

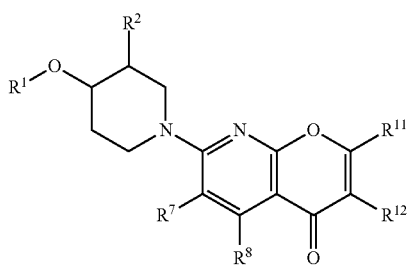

Ie wherein $R^1$, $R^2$, $R^7$, $R^8$, $R^{11}$ and $R^{12}$ are defined herein; or a pharmaceutically acceptable salt thereof.

An embodiment of the present invention includes compounds of the formula If:

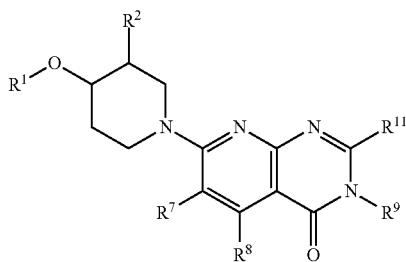

If wherein $R^1$, $R^2$, $R^7$, $R^8$, $R^9$ and $R^{11}$ are defined herein; or a pharmaceutically acceptable salt thereof.

An embodiment of the present invention includes compounds of the formula Ig:

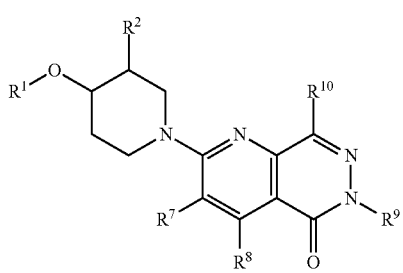

Ig wherein $R^1$, $R^2$, $R^7$, $R^8$, $R^9$ and $R^{10}$ are defined herein; or a pharmaceutically acceptable salt thereof.

An embodiment of the present invention includes compounds of the formula Ih:

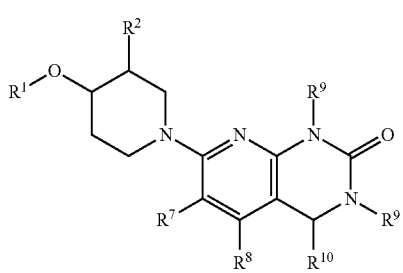

Ih wherein $R^1$, $R^2$, $R^7$, $R^8$, $R^9$ and $R^{10}$ are defined herein; or a pharmaceutically acceptable salt thereof.

An embodiment of the present invention includes compounds of the formula Ii:

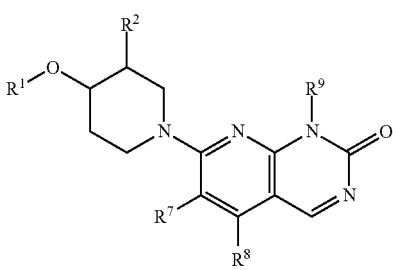

Ii wherein $R^1$, $R^2$, $R^7$, $R^8$ and $R^9$ are defined herein; or a pharmaceutically acceptable salt thereof.

An embodiment of the present invention includes compounds of the formula Ij:

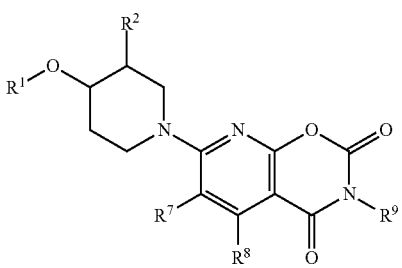

Ij wherein $R^1$, $R^2$, $R^7$, $R^8$ and $R^9$ are defined herein; or a pharmaceutically acceptable salt thereof.

An embodiment of the present invention includes compounds of the formula Ik:

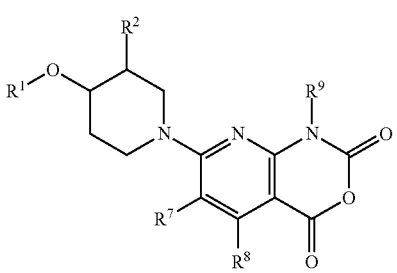

Ik wherein $R^1$, $R^2$, $R^7$, $R^8$ and $R^9$ are defined herein; or a pharmaceutically acceptable salt thereof.

An embodiment of the present invention includes compounds of the formula Im:

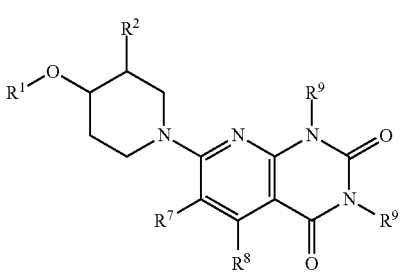

Im wherein R¹, R², R⁷, R⁸ and R⁹ are defined herein; or a pharmaceutically acceptable salt thereof.

An embodiment of the present invention includes compounds of the formula In:

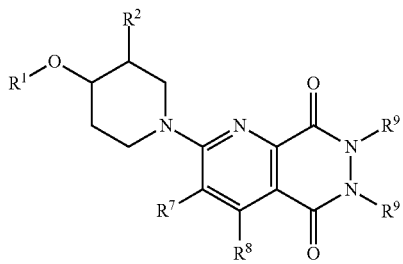

In wherein R¹, R², R⁷, R⁸ and R⁹ are defined herein; or a pharmaceutically acceptable salt thereof.

An embodiment of the present invention includes compounds of the formula Io:

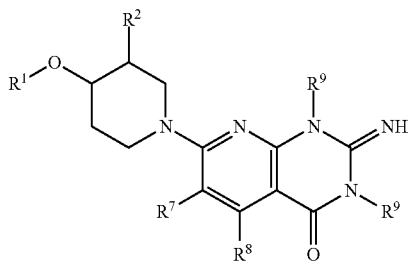

Io wherein R¹, R², R⁷, R⁸ and R⁹ are defined herein; or a pharmaceutically acceptable salt thereof.

An embodiment of the present invention includes compounds of the formula I, or a pharmaceutically acceptable salt thereof, wherein the variables -Q-X—Y—Z— comprise a group that is selected from:

(1) —(CHR¹⁰)—(CHR¹¹)—(NR⁹)—(C=O)—,
(2) —(C=O)—(NR⁹)—(CHR¹²)—(CHR¹⁰)—,
(3) —(CR¹⁰)=(CR¹¹)—O—(C=O)—,
(4) —O—(CR¹¹)=(CR¹²)—(C=O)—,
(5) —N=(CR¹¹)—(NR⁹)—(C=O)—,
(6) —(CR¹⁰)=(CR¹¹)—(NR⁹)—(C=O)—,
(7) —(CR¹⁰)=N—(NR⁹)—(C=O)—,
(8) —(NR⁹)—(C=O)—(NR⁹)—(CHR¹⁰)—,
(9) —(NR⁹)—(C=O)—N=(CR¹⁰)—,
(10) —O—(C=O)—(NR⁹)—(C=O)—,
(11) —(NR⁹)—(C=O)—O—(C=O)—,
(12) —(NR⁹)—(C=O)—(NR⁹)—(C=O)—,
(13) —(C=O)—(NR⁹)—(NR⁹)—(C=O)—, and
(14) —(NR⁹)—(C=NH)—(NR⁹)—(C=O)—.

An embodiment of the present invention includes compounds of the formula I, or a pharmaceutically acceptable salt thereof, wherein the group:

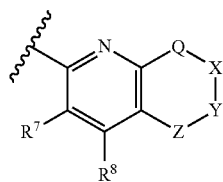

is selected from the group consisting of:

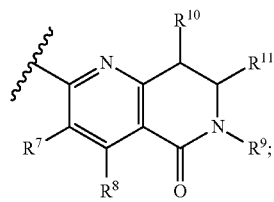

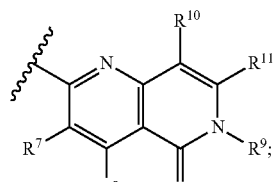

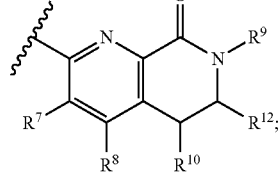

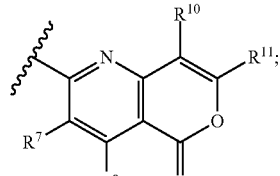

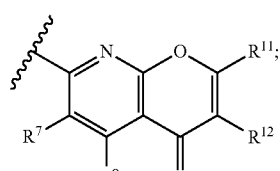

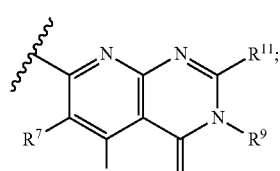

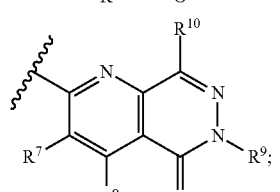

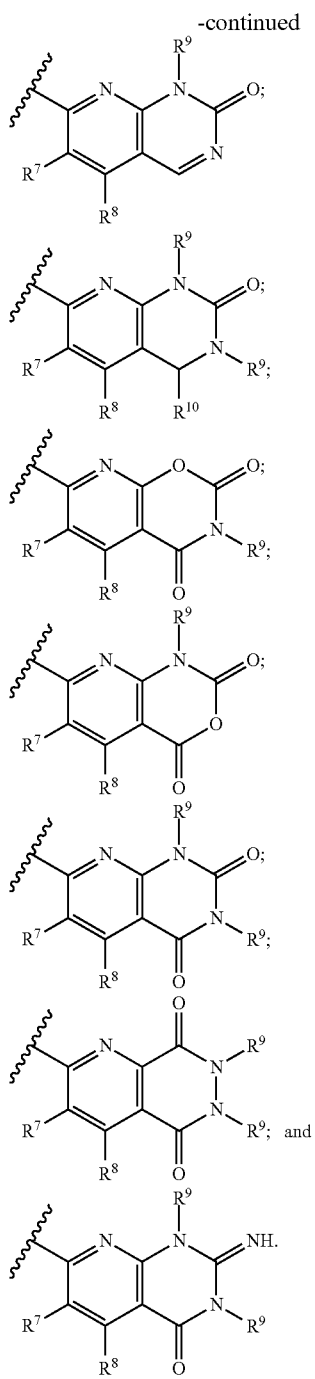

An embodiment of the present invention includes compounds wherein $R^1$ is selected from the group consisting of: benzodioxolyl, benzoimidazolyl, benzoxazolyl, benzooxazinone, benzooxazolone, benzothiazolyl, chromanyl, cyclopentapyridinyl, dihydrobenzo[1,4]dioxinyl, dihydrobenzofuranyl, dihydrobenzo[1,4]oxazinyl, dihydrofuropyridinyl, dihydroisobenzofuranyl, dihydroisoquinolinone, dihydropyranopyridinyl, dihydroimidazopyridine, dihydropyrido[1,4]oxazinyl, dihydroquinolinone, indazolyl, indanyl, indolyl, isochromanone, isobenzofuranone, isochromanyl, isoindolinyl, isoxazolyl, oxoisoindolinyl, phenyl, pyrazolopyridinyl, pyrazolyl, pyridyl, pyrrolopyridinyl, pyrimidinyl, quinolinone, quinolinyl, tetrahydrofuranyl, tetrahydroisoquinolinyl, tetrahydroquinolinyl, and tetrahydropyranyl, which is substituted with one or more of $R^{1a}$, $R^{1b}$ and $R^{1c}$.

An embodiment of the present invention includes compounds wherein $R^1$ is phenyl or pyridyl, which is substituted with $R^{1a}$, $R^{1b}$ and $R^{1c}$, wherein $R^{1a}$, $R^{1b}$ and $R^{1c}$ are independently selected from the group consisting of
(a) hydrogen,
(b) hydroxyl,
(c) halogen,
(d) $C_{1-6}$alkyl, which is unsubstituted or substituted with substituents selected from the group consisting of: hydroxy, fluoro, and —$OCH_3$,
(e) —O—$C_{1-6}$alkyl, which is unsubstituted or substituted with substituents selected from the group consisting of: hydroxy, fluoro, and —$OCH_3$,
(f) $C_{3-6}$cycloalkyl, which is unsubstituted or substituted with a substituent selected from the group consisting of: $C_{1-6}$alkyl and hydroxy; and
(g) —CN.

An embodiment of the present invention includes compounds wherein $R^1$ is phenyl or pyridyl, which is substituted with $R^{1a}$, $R^{1b}$ and $R^{1c}$, wherein $R^{1a}$, $R^{1b}$ and $R^{1c}$ are independently selected from the group consisting of
(a) hydrogen,
(b) hydroxyl,
(c) halogen,
(d) $C_{1-3}$alkyl, which is unsubstituted or substituted with a substituent selected from the group consisting of: hydroxy, 1-3 fluoro, and —$OCH_3$,
(e) —O—$C_{1-3}$alkyl, which is unsubstituted or substituted with a substituent selected from the group consisting of: 1-3 fluoro, and —$OCH_3$, and
(g) —CN.

An embodiment of the present invention includes compounds wherein $R^1$ is selected from the group consisting of:
(a) hydrogen,
(b) phenyl, which is unsubstituted or substituted with $C_{1-3}$alkyl or —CN, and
(c) pyridyl, which is unsubstituted or substituted with $C_{1-3}$alkyl or —O—$C_{1-3}$alkyl.

An embodiment of the present invention includes compounds wherein $R^1$ is phenyl, which is unsubstituted or substituted with —CN. An embodiment of the present invention includes compounds wherein $R^1$ is pyridyl, which is unsubstituted or substituted with —$OCH_3$.

An embodiment of the present invention includes compounds wherein $R^2$ is hydrogen and $R^3$ is hydrogen. An embodiment of the present invention includes compounds wherein $R^2$ is fluoro and $R^3$ is hydrogen. An embodiment of the present invention includes compounds wherein $R^2$ is fluoro and $R^3$ is fluoro.

An embodiment of the present invention includes compounds wherein $R^7$ is selected from the group consisting of:
(1) hydrogen,
(2) methyl, and
(3) ethyl.

An embodiment of the present invention includes compounds wherein $R^7$ is —$CH_3$.

An embodiment of the present invention includes compounds wherein $R^8$ is selected from the group consisting of:
(1) hydrogen,
(2) methyl, and
(3) ethyl.

An embodiment of the present invention includes compounds wherein $R^8$ is hydrogen. An embodiment of the present invention includes compounds wherein $R^8$ is —$CH_3$.

An embodiment of the present invention includes compounds wherein $R^9$ is selected from the group consisting of:
(1) hydrogen, and
(2) —$C_{1-6}$alkyl, which is unsubstituted or substituted with hydroxy, methoxy, 1-3 fluoro.

An embodiment of the present invention includes compounds wherein $R^9$ is hydrogen. An embodiment of the present invention includes compounds wherein $R^9$ is methyl. An embodiment of the present invention includes compounds wherein $R^9$ is —$CH_2CH_2OH$.

An embodiment of the present invention includes compounds wherein $R^{10}$ is hydrogen. An embodiment of the present invention includes compounds wherein $R^{10}$ is —$CH_3$. An embodiment of the present invention includes compounds wherein $R^{10}$ is —$CH_2OH$.

An embodiment of the present invention includes compounds wherein $R^{11}$ is hydrogen. An embodiment of the present invention includes compounds wherein $R^{11}$ is —$CH_3$. An embodiment of the present invention includes compounds wherein $R^{11}$ is —$CH_2OH$.

An embodiment of the present invention includes compounds wherein $R^{12}$ is hydrogen. An embodiment of the present invention includes compounds wherein $R^{12}$ is —$CH_3$. An embodiment of the present invention includes compounds wherein $R^{12}$ is —$CH_2OH$.

Certain embodiments of the present invention include a compound which is selected from the group consisting of the subject compounds of the Examples herein or a pharmaceutically acceptable salt thereof.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. Likewise, the present invention includes tautomeric forms of the compounds disclosed herein. Formula I shows the structure of the class of compounds without specific stereochemistry. At least some of the chemical names of compounds of the invention as set forth in this application may have been generated on an automated basis by use of commercially available chemical naming software programs, and have not been independently verified.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

As appreciated by those of skill in the art, halogen or halo as used herein are intended to include fluoro, chloro, bromo and iodo. Similarly, $C_{1-6}$, as in $C_{1-6}$alkyl is defined to identify the group as having 1, 2, 3, 4, 5 or 6 carbons in a linear or branched arrangement, such that $C_{1-6}$alkyl specifically includes methyl, ethyl, n-propyl, iso-propyl, n-butyl, iso-butyl, tert-butyl, pentyl, and hexyl. Substituents (such as $R^{1a}$, $R^{1b}$ and $R^{1c}$) may be absent if the valency of the group to which they are attached does not permit such substitution. The value of a variable (such as $R^9$) at a particular position is independent of its value at a different position. A group which is designated as being independently substituted with substituents may be independently substituted with multiple numbers of such substituents.

The term "heteroaryl" as used herein represents a stable monocyclic, bicyclic or tricyclic ring of up to 7 atoms in each ring, wherein at least one ring is aromatic and contains carbon and from 1 to 4 heteroatoms selected from the group consisting of O, N and S. In another embodiment, the term heteroaryl refers to a monocyclic, bicyclic or tricyclic aromatic ring of 5- to 14-ring atoms of carbon and from one to four heteroatoms selected from O, N, or S. As with the definition of heterocyclyl below, "heteroaryl" is also understood to include the N-oxide derivative of any nitrogen-containing heteroaryl. In cases where the heteroaryl substituent is bicyclic and one ring is non-aromatic, in one embodiment, the attachment is via a carbon atom of the aromatic ring. Examples of heteroaryl include but are not limited to benzodioxolyl, benzofuranyl, benzofurazanyl, benzoimidazolyl, benzimidazolonyl, benzopyrazolyl, benzothiazolyl, benzotriazolyl, benzothiophenyl, benzoxazepinyl, benzooxazinonyl, benzooxazolonyl, benzoxazolyl, carbazolyl, carbolinyl, chromanyl, cinnolinyl, cyclopentapyridinyl, dihydrobenzo[1,4]dioxinyl, dihydrobenzofuranyl, dihydrobenzo[1,4]oxazinyl, dihydrofuropyridinyl, dihydroindolyl, dihydroisobenzofuranyl, dihydroisoquinolinonyl, dihydropyranopyridinyl, dihydroimidazopyridinyl, dihydropyrido[1,4]oxazinyl, dihydroquinolinone, furanyl, imidazolyl, indolinyl, indolyl, indanyl, indolazinyl, indazolyl, isobenzofuranyl, isobenzofuranonyl, isochromanonyl, isochromanyl, isoindolinyl, isoindolyl, isoxazolinyl, isoxazolyl, isoquinolyl, isothiazolyl, isoxazolyl, naphthpyridinyl, oxadiazolyl, oxazolyl, oxazolinyl, oxetanyl, oxoisoindolinyl, pyrazinyl, pyrazolopyridinyl, pyrazolyl, pyridazinyl, pyridopyridinyl, pyridazinyl, pyridyl, pyrimidinyl, pyrimidyl, pyrrolopyridinyl, pyrrolyl, quinazolinyl, quinolyl, quinoxalinyl, tetrahydrobenzooxepinyl, tetrahydroisoquinolinyl, tetrahydropyranyl, tetrahydroquinoxalinyl, tetrazolyl, tetrazolopyridyl, thiadiazolyl, thiazolyl, thienyl, triazolyl, and N-oxides thereof, and wherein the saturated heterocyclic moieties include azetidinyl, 1,4-dioxanyl, hexahydroazepinyl, piperazinyl, piperidinyl, pyridin-2-onyl, pyrrolidinyl, morpholinyl, tetrahydrofuranyl, thiomorpholinyl, and tetrahydrothienyl, and N-oxides thereof.

"Heterocyclyl" means a non-aromatic saturated monocyclic, bicyclic, tricyclic or spirocyclic ring system comprising up to 7 atoms in each ring, or contains 3 to 14, or 5 to 10 ring atoms, in which one or more of the atoms in the ring system is an element other than carbon, for example, nitrogen, oxygen, phosphor or sulfur, alone or in combination. There are no adjacent oxygen and/or sulfur atoms present in the ring system. In one embodiment, the heterocyclyls contain about 5 to about 6 ring atoms. The heterocyclyl may be fused with an aromatic aryl group such as phenyl or heterocyclenyl. The heterocyclyl is optionally bridged (i.e., forming a bicyclic moiety), for example with a methylene, ethylene or propylene bridge. The prefix aza, oxa or thia before the heterocyclyl root name means that at least a nitrogen, oxygen or sulfur atom, respectively, is present as a ring atom. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydropyran, tetrahydrothiophenyl, lactam, lactone, and the like. "Heterocyclyl" also includes heterocyclyl rings as described above wherein =O replaces two available hydrogens on the same ring carbon atom.

The present invention also includes all pharmaceutically acceptable isotopic variations of a compound of the Formula I in which one or more atoms is replaced by atoms having the same atomic number, but an atomic mass or mass number different from the atomic mass or mass number usually found in nature. Such compounds are identical to those disclosed herein, but for the fact that one or more atoms are replaced by an atom having an atomic mass or mass number different from the atomic mass or mass number usually found in nature. Examples of isotopes that can be incorporated into the compounds of the invention include isotopes of hydrogen such as $^2$H and $^3$H, carbon such as $^{11}$C, $^{13}$C and $^{14}$C, nitrogen such as $^{13}$N and $^{15}$N, oxygen such as $^{15}$O, $^{17}$O and $^{18}$O, phosphorus such as $^{32}$P, sulfur such as $^{35}$S, fluorine such as $^{18}$F, iodine such as $^{123}$I and $^{125}$I, and chlorine such as $^{36}$Cl. Certain isotopically-labelled compounds of Formula I, for example those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy. An embodiment of the present invention includes compounds that are substituted with a positron emitting isotope. An embodiment of the present invention includes compounds that are substituted with a $^{11}$C isotope. An embodiment of the present invention includes compounds that are substituted with an $^{18}$F isotope. In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium (H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of the invention can be prepared without undue experimentation by conventional techniques well known to those skilled in the art or by processes analogous to those described in the schemes and examples herein using appropriate isotopically-enriched reagents and/or intermediates.

Those skilled in the art will recognize those instances in which the compounds of the invention may form salts. In such instances, another embodiment provides pharmaceutically acceptable salts of the compounds of the invention. Thus, reference to a compound of the invention herein is understood to include reference to salts thereof, unless otherwise indicated. The term "pharmaceutically acceptable salts" refers to salts prepared from pharmaceutically acceptable non-toxic bases or acids including inorganic or organic bases and inorganic or organic acids. In addition, when a compound of the invention contains both a basic moiety, such as, but not limited to a pyridine or imidazole, and an acidic moiety, such as, but not limited to a carboxylic acid, zwitterions ("inner salts") may be formed and are included within the present invention. Salts derived from inorganic bases include aluminum, ammonium, calcium, copper, ferric, ferrous, lithium, magnesium, manganic salts, manganous, potassium, sodium, zinc, and the like. Particular embodiments include the ammonium, calcium, magnesium, potassium, and sodium salts. Salts in the solid form may exist in more than one crystal structure, and may also be in the form of hydrates or solvates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments include the citric, hydrobromic, hydrochloric, maleic, phosphoric, sulfuric, fumaric, and tartaric acids. It will be understood that, as used herein, references to the compounds of Formula I are meant to also include the pharmaceutically acceptable salts. Salts of the compounds of the invention may be formed by methods known to those of ordinary skill in the art, for example, by reacting a compound of the invention with an amount of acid or base, such as an equivalent amount, in a medium such as one in which the salt precipitates or in an aqueous medium followed by lyophilization.

Exemplifying the invention is the use of the compounds disclosed in the Examples and herein. Specific compounds within the present invention include a compound which is selected from the group consisting of the compounds disclosed in the following Examples and pharmaceutically acceptable salts thereof and individual enantiomers or diastereomers thereof.

As used herein, the term "M4 muscarinic acetylcholine receptor" refers to one of the five subtypes of the muscarinic acetylcholine receptor, which is from the superfamily of G-protein coupled receptors. The family of muscarinic receptors is described, for example, in *Pharmacol Ther,* 1993, 58:319-379; *Eur J Pharmacol,* 1996, 295:93-102, and *Mol Pharmacol,* 2002, 61:1297-1302. The muscarinic receptors are known to contain one or more allosteric sites, which may alter the affinity with which muscarinic ligands bind to the primary binding or orthosteric sites. See, e.g., S. Lazareno, et al., *Mol Pharmacol,* 2002, 62:6, 1491-1505.

As used herein, the terms "positive allosteric modulator" and "allosteric potentiator" are used interchangeably, and refer to a ligand which interacts with an allosteric site of a receptor to augment the response produced by the endogenous ligand at the orthosteric binding site. The compounds of the invention are allosteric modulators of the M4 muscarinic acetylcholine receptor, including as positive allosteric modulators of the M4 muscarinic acetylcholine receptor and silent allosteric modulators of the M4 muscarinic acetylcholine receptor. Some of the compounds of the invention are agonists of the M4 muscarinic acetylcholine receptor. Some of the compounds of the invention are allosteric modulators of the M1 muscarinic acetylcholine receptor, or may be agonists of the M1 muscarinic acetylcholine receptor. For example, a modulator or potentiator may directly or indirectly augment the response produced by the endogenous ligand (such as acetylcholine or xanomeline) at the orthosteric site of the M4 muscarinic acetylcholine receptor in an animal, in particular, a human.

The actions of ligands at allosteric receptor sites may also be understood according to the "allosteric ternary complex model," as known by those skilled in the art. The allosteric ternary complex model is described with respect to the family of muscarinic receptors in Birdsall et al, *Life Sciences,* 2001, 68:2517-2524. For a general description of the role of allosteric binding sites, see Christopoulos, *Nature Reviews: Drug Discovery,* 2002, 1:198-210.

It is believed that the compounds of the invention bind to an allosteric binding site that is distinct from the orthosteric acetylcholine site of the M4 muscarinic acetylcholine receptor, thereby augmenting the response produced by the endogenous ligand acetylcholine at the orthosteric site of the M4 muscarinic acetylcholine receptor. It is also believed that the compounds of the invention bind to an allosteric site which is distinct from the xanomeline site of the M4 muscarinic acetylcholine receptor, thereby augmenting the response produced by the endogenous ligand xanomeline at the orthosteric site of the M4 muscarinic acetylcholine receptor.

The present invention is also directed to the use of the compounds disclosed herein as modulators of M4 muscarinic acetylcholine receptor activity. The subject compounds and pharmaceutically acceptable salts thereof are useful in a method of M4 modulating muscarinic acetylcholine receptor activity in a subject such as a mammal comprising the administration of an amount of the compound. In addition to primates, especially humans, a variety of other mammals may be administered with a compound of the present invention. The present invention is directed to a compound of the present invention or a pharmaceutically acceptable salt thereof that could be useful in therapy. The present invention may further be directed to a use of a compound of the present invention or a pharmaceutically acceptable salt thereof for the manufacture of a medicament for modulating M4 muscarinic acetylcholine receptor activity or treating the disorders and diseases noted herein in humans and animals.

A subject administered with a compound of the present invention, or a pharmaceutically acceptable salt thereof, is generally a mammal, such as a human being, male or female. The amount of compound administered to the subject is an amount sufficient to modulate the M4 muscarinic acetylcholine receptor in the subject. In an embodiment, the amount of compound can be an "effective amount" or "therapeutically effective amount", wherein the subject compound or pharmaceutical composition is administered in an amount that will elicit the biological or medical response of a tissue, system, animal or human that is being sought by the researcher, veterinarian, medical doctor or other clinician, or otherwise inhibiting the noted disease and thus producing the desired therapeutic, ameliorative, inhibitory or preventative effect. An effective amount does not necessarily include considerations of toxicity and safety related to the administration of the compound. It is recognized that one skilled in the art may affect neurological and psychiatric disorders associated with M4 muscarinic acetylcholine receptor modulation by treating a subject presently afflicted with the disorders, or by prophylactically treating a subject likely to be afflicted with the disorders, with an effective amount of a compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a subject that is predisposed to such disease or disorder. The terms "administration of" and "administering" a compound should be understood to mean providing a compound of the invention or a prodrug of a compound of the invention to to the subject. The term "dysfunction" refers to abnormality or impairment in the function of the noted system.

The term "composition" as used herein is intended to encompass a product comprising the specified ingredients in the specified amounts, as well as any product which results, directly or indirectly, from combination of the specified ingredients in the specified amounts. Such term is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The utility of the compounds in accordance with the present invention as modulators of M4 muscarinic acetylcholine receptors may be readily determined without undue experimentation by methodology well known in the art, including monitoring the mobilization of intracellular $Ca^{++}$, determining the levels of intracellular cAMP, or quantiting the exchange of GDP for $[35S]\gamma GTP$.

In a typical experiment the M4 muscarinic acetylcholine receptor modulating activity of the compounds of the present invention was determined in accordance with the following experimental method. CHO-K1 cells stably transfected with human M4 receptor and chimeric G-protein Gαqi5 (Coward P, et al., Analytical Biochemistry, 270:242-248 (1999)) are thawed from liquid $N_2$ storage, resuspended in growth medium, plated in black, clear bottom 384 well plates, and incubated 16-20 hours at 37° C., 5% $CO_2$. On the day of assay, growth medium is removed, the cells are washed 2 times with wash buffer, and cells are incubated in dye loading buffer at 37° C., 5% $CO_2$ for ~1 hour. Following dye loading the cell plates are placed in a FLIPR Tetra instrument and while monitoring dye fluorescence (excitation 470-495 nM/emission 515-575 nM), 10 uL of test substance at increasing concentrations is added, and fluorescence values are recorded for 4 min. Next, 10 uL of acetylcholine is added (final concentration calculated so as to achieve 20% of the maximum acetycholine response), and the fluorescence reading is continued for 3.5 min. In some cases, a third addition of acetylcholine (final concentration calculated to achieve 70% of the maximal acetylcholine response) is performed. The resulting dose response curves are fit to a 4 parameter logistic equation and the final result is determined as the inflection point (IP) of the curve The intrinsic M4 muscarinic acetylcholine receptor modulating activity of a compound which may be used in the present invention may be determined by these assays.

All of the final compounds of the following examples had activity in the human FLIPR-based M4 PAM assay with an IP of about 5 nM to 15000 nM against the human M4 muscarinic acetylcholine receptor. Additional data is provided in the following Examples. Such a result is indicative of the intrinsic activity of the compounds in use as a modulating the human M4 muscarinic acetylcholine receptor. In general, one of ordinary skill in the art would appreciate that a substance is considered to effectively modulate the human M4 muscarinic acetylcholine receptor if it has an IP of less than about 50 μM, or more specifically less than about 15000 nM.

The M4 muscarinic acetylcholine receptor has been implicated in a wide range of biological functions. This has suggested a potential role for these receptors in a variety of disease processes in humans or other species. The compounds of the present invention could therefore potentially have utility in treating, preventing, ameliorating, controlling or reducing the risk of a variety of neurological and psychiatric disorders associated with M4 muscarinic acetylcholine receptors, including one or more of the following conditions or diseases, and other diseases related to general M4 muscarinic acetylcholine receptor system dysfunction.

Potential conditions or disorders for which the compounds of the invention may be useful further include one or more of the following conditions or diseases: Alzheimer's disease (including mild Alzheimer's disease, moderate Alzheimer's disease and severe Alzheimer's disease), olfactory impairment associated with Alzheimer's disease, Down's syndrome, olfactory impairment associated with Down's syndrome, Parkinson's disease, olfactory impairment associated with Parkinson's disease, stroke, microgliosis brain inflammation, pre-senile dementia, senile dementia, progressive supranuclear palsy, cortical basal degeneration, β-amyloid angiopathy, cerebral amyloid angiopathy, hereditary cerebral hemorrhage, cognitive disorders (including mild cognitive impairment), glaucoma, amyloidosis, type II diabetes, diabetes-associated amyloidogenesis, scrapie, bovine spongiform encephalitis, traumatic brain injury, Creutzfeld-Jakob disease, schizophrenia, sleep disorders, pain disorders (including acute pain, inflammatory pain and neuropathic pain), pulmonary hypertension, chronic obstructive pulmonary disease (COPD), asthma, urinary incontinence, glaucoma, schizophrenia, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes, autism, atherosclerosis, tolerance and/or dependence to opioid treatment of pain, and for treatment of withdrawal syndrome of e.g., alcohol, opioids, and cocaine, Huntington's disease, drug-induced dyskinesias.

Potential conditions or disorders for which the compounds of the invention may be useful further include one or more of the following conditions or diseases: schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketamine and other dissociative anaesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Levodopa induced dyskinesia, other drug induced dyskinesia (e.g. tardive dyskinesias), Huntington's disease, Pick's disease, Creutzfeldt-Jacob disease, perinatal hypoxia, other general medical conditions or substance abuse); delirium, amnestic disorders or age related cognitive decline; delusional disorder, shared psychotic disorder, catastrophic schizophrenia, postpartum psychosis, psychotic depression, psychotic break, tardive psychosis, myxedematous psychosis, occupational psychosis, menstrual psychosis, secondary psychotic disorder, bipolar I disorder with psychotic features, and substance-induced psychotic disorder; major depressive disorder, affective disorder, bipolar disorder, electrolyte disorder, neurological disorder, hypoglycemia, AIDS, lupus, and post-traumatic stress disorder; brain tumor, dementia with Lewy bodies, multiple sclerosis, sarcoidosis, Lyme disease, syphilis, Alzheimer's disease, Parkinson's disease, and anti-NMDA receptor encephalitis. Thus, in another specific embodiment, the present invention provides a method for treating schizophrenia or psychosis comprising administering to a patient in need thereof an effective amount of a compound of the present invention. At present, the text revision of the fourth edition of the Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorder. As used herein, the term "schizophrenia or psychosis" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "schizophrenia or psychosis" is intended to include like disorders that are described in other diagnostic sources.

Potential conditions or disorders for which the compounds of the invention may be useful further include one or more of the following conditions or diseases: mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder, mood disorders due to a general medical condition, and substance-induced mood disorders; affective neurosis; depressive neurosis; anxiety neurosis; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; acute neurological and psychiatric disorders such as cerebral deficits subsequent to cardiac bypass surgery and grafting, stroke, ischemic stroke, cerebral ischemia, spinal cord trauma, head trauma, perinatal hypoxia, cardiac arrest, hypoglycemic neuronal damage; idiopathic and drug-induced Parkinson's disease; muscular spasms and disorders associated with muscular spasticity including tremors, epilepsy, convulsions, seizure disorders, absence seisures, complex partial and generalized seizures; Lennox-Gastaut syndrome; cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; dissociative disorders including multiple personality syndromes and psychogenic amnesias; substance-related disorders, substance use, substance abuse, substance seeking, substance reinstatement, all types of psychological and physical addictions and addictive behaviors, reward-related behaviors (including substance-induced delirium, persisting dementia, persisting amnestic disorder, psychotic disorder or anxiety disorder; tolerance, addictive feeding, addictive feeding behaviors, binge/purge feeding behaviors, dependence, withdrawal or relapse from substances including alcohol, amphetamines, cannabis, cocaine, hallucinogens, inhalants, morphine, nicotine, opioids, phencyclidine, sedatives, hypnotics or anxiolytics); appetite, taste, eating or drinking disorders; movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), chronic fatigue syndrome, fatigue, including Parkinson's fatigue, multiple sclerosis fatigue, fatigue caused by a sleep disorder or a circadian rhythm disorder, medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, and dyskinesias [including tremor (such as rest tremor, essential tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), restless leg syndrome and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); neurodegenerative disorders including nosological entities such as disinhibition-dementia-parkinsonism-amyotrophy complex; pallido-ponto-nigral degeneration; epilepsy; seizure disorders; attention deficit/hyperactivity disorder (ADHD); conduct disorder; migraine (including migraine headache); headache; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; emesis, nausea, vomiting; gastric dyskinesia; gastric ulcers; Kallman's syndrome (anosmia); asthma; cancer; conditions associated with visceral pain such as irritable bowel syndrome, and angina; eating disorders; urinary incontinence; substance tolerance, substance withdrawal (including, substances such as opiates, nicotine, tobacco products, alcohol, benzodiazepines, cocaine, sedatives, hypnotics, etc.); psychosis; schizophrenia; anxiety (including generalized anxiety disorder, panic disorder, and obsessive compulsive disorder); mood disorders (including depression, mania, bipolar disorders); trigeminal neuralgia; hearing loss; tinnitus; neuronal damage including ocular damage; retinopathy; macular degeneration of the eye; emesis; brain edema; pain, including acute and chronic pain states, severe pain, intractable pain, inflammatory pain, neuropathic pain, post-traumatic pain, bone and joint pain (osteoarthritis), repetitive motion pain, dental pain, cancer pain, myofascial pain (muscular injury, fibromyalgia), perioperative pain (general surgery, gynecological), chronic pain, neuropathic pain, post-traumatic pain, trigeminal neuralgia, migraine and migraine headache.

Potential sleep conditions or disorders for which the compounds of the invention may be useful include enhancing sleep quality; improving sleep quality; augmenting sleep maintenance; increasing the value which is calculated from the time that a subject sleeps divided by the time that a subject is attempting to sleep; decreasing sleep latency or onset (the time it takes to fall asleep); decreasing difficulties in falling asleep; increasing sleep continuity; decreasing the number of awakenings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; increasing daytime alertness; reducing daytime drowsiness; treating or reducing excessive daytime sleepiness; insomnia; hypersomnia; narcolepsy; interrupted sleep; sleep apnea; wakefulness; nocturnal myoclonus; REM sleep interruptions; jet-lag; shift workers' sleep disturbances; dyssomnias; night terror; insomnias associated with depression, emotional/mood disorders, as well as sleep walking and enuresis, and sleep disorders which accompany aging; Alzheimer's sundowning; conditions associated with circadian rhythmicity as well as mental and physical disorders associated with travel across time zones and with rotating shift-work schedules; conditions due to drugs which cause reductions in REM sleep as a side effect; syndromes which are manifested by non-restorative sleep and muscle pain or sleep apnea which is associated with respiratory disturbances during sleep; and conditions which result from a diminished quality of sleep.

Pain disorders for which the compounds of the invention may be useful include neuropathic pain (such as postherpetic neuralgia, nerve injury, the "dynias", e.g., vulvodynia, phantom limb pain, root avulsions, painful diabetic neuropathy, painful traumatic mononeuropathy, painful polyneuropathy); central pain syndromes (potentially caused by virtually any lesion at any level of the nervous system); postsurgical pain syndromes (eg, postmastectomy syndrome, postthoracotomy syndrome, stump pain); bone and joint pain (osteoarthritis), repetitive motion pain, dental pain, cancer pain, myofascial pain (muscular injury, fibromyalgia); perioperative pain (general surgery, gynecological), chronic pain, dysmennorhea, as well as pain associated with angina, and inflammatory pain of varied origins (e.g. osteoarthritis, rheumatoid arthritis, rheumatic disease, teno-synovitis and gout), headache, migraine and cluster headache, headache, primary hyperalgesia, secondary hyperalgesia, primary allodynia, secondary allodynia, or other pain caused by central sensitization.

The subject compounds could further be of potential use in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to subjects (animals and human) in need of such treatment in dosages that will provide optimal pharmaceutical efficacy. The selected dosage depends upon the desired therapeutic effect, on the route of administration, and on the duration of the treatment. The dose will vary from subject to subject depending upon the nature and severity of disease, the subject's weight, special diets then being followed by a subject, concurrent medication, and other factors which those skilled in the art will recognize. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Generally, dosage levels of between 0.0001 to 10 mg/kg of body weight daily are administered to the subject, e.g., humans and elderly humans, to obtain effective modulation of M4 muscarinic acetylcholine receptors. The dosage range will generally be about 0.5 mg to 1.0 g per subject per day which may be administered in single or multiple doses. In one embodiment, the dosage range will be about 0.5 mg to 500 mg per subject per day; in another embodiment about 0.5 mg to 200 mg per subject per day; and in yet another embodiment about 5 mg to 50 mg per subject per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 30 mg, 50 mg, 80 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the subject to be treated. The compounds may be administered on a regimen of 1 to 4 times per day, such as once or twice per day. The compounds may be administered before bedtime. For example, the compounds may be administered about 1 hour prior to bedtime, about 30 minutes prior to bedtime or immediately before bedtime.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is contemplated. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is contemplated. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The compounds of the present invention may be used in combination with one or more other drugs in the treatment of diseases or conditions for which the compounds of the present invention have utility, where the combination of the drugs together are safer or more effective than either drug alone. In a embodiment, the subject compound may be employed in combination with other compounds which are known in the art, either administered separately or in the same pharmaceutical compositions, including, but are not limited to: anti-Alzheimer's agents; beta-secretase inhibitors, such as verubecestat; alpha 7 nicotinic agonists, such as ABT089, SSR180711 and MEM63908; HT2a modulators, such as pimavaserin; ADAM 10 ligands or activators; gamma-secretase inhibitors, such as LY450139 and TAK 070; gamma-secretase inhibitors; gamma secretase modulators; tau phosphorylation inhibitors; glycine transport inhibitors; LXR β agonists; ApoE4 conformational modulators; NR2B antagonists; androgen receptor modulators; blockers of Aβ oligomer formation; 5-HT4 agonists, such as PRX-03140; 5-HT6 antagonists, such as GSK 742467, SGS-518, FK-962, SL-65.0155, SRA-333 and xaliproden; 5-HT1a antagonists, such as lecozotan; p25/CDKS inhibitors; NK1/NK3 receptor antagonists; COX-2 inhibitors; HMG-CoA reductase inhibitors; NSAID's including ibuprofen; vitamin E; anti-amyloid antibodies (including anti-amyloid humanized monoclonal antibodies), such as bapineuzumab, ACC001, CAD106, AZD3102, H12A11V1; anti-inflammatory compounds such as (R)-flurbiprofen, nitroflurbiprofen, ND-1251, VP-025, HT-0712 and EHT-202; PPAR gamma agonists, such as pioglitazone and rosiglitazone; CB-1 receptor antagonists or CB-1 receptor inverse agonists, such as AVE1625; antibiotics such as doxycycline and rifampin; CB-1 receptor antagonists or CB-1 receptor inverse agonists; antibiotics such as doxycycline and rifampin; N-methyl-D-aspartate (NMDA) receptor antagonists, such as memantine, neramexane and EVT101; recombinant growth hormone; growth hormone secretagogues such as ibutamoren, ibutamoren mesylate, and capromorelin; histamine $H_3$ receptor antagonists such as ABT-834, ABT 829, GSK 189254 and CEP16795; AMPA agonists or AMPA modulators, such as CX-717, LY 451395, LY404187 and S-18986; neuronal nicotinic agonists; muscarinic antagonists (e.g., M1 agonists (such as acetylcholine, oxotremorine, carbachol, or McNa343), or $M_2$ antagonists (such as atropine, dicycloverine, tolterodine, oxybutynin, ipratropium, methoctramine, tripitamine, or gallamine)); cholinesterase inhibitors (e.g., acetyl- and/or butyrylchlolinesterase inhibitors such as donepezil (Aricept®, (±)-2,3-dihydro-5,6-dimethoxy-2-[[1-(phenylmethyl)-4-piperidinyl]methyl]-1H-inden-1-one hydrochloride), tacrine, phenserine, ladostigil, ABT-089, galantamine (Razadyne®), and rivastigimine (Exelon®); N-methyl-D-aspartate receptor antagonists (e.g., Namenda® (memantine HCl, available from Forrest Pharmaceuticals, Inc.); combinations of cholinesterase inhibitors and N-methyl-D-aspartate receptor antagonists; anti-inflammatory agents that can reduce neuroinflammation; glycogen synthase kinase beta inhibitors; promoters of alpha secretase activity; PDE IV inhibitors, including MEM1414, HT0712 and AVE8112; PDE-10 inhibitors; Tau kinase inhibitors (e.g., GSK3beta inhibitors, cdk5 inhibitors, or ERK inhibitors); GSK3β inhibitors, including AZD1080, SAR502250 and CEP16805; neuronal nicotinic agonists; selective M1 agonists; HDAC inhibitors; and microtubule affinity regulating kinase (MARK) ligands; Tau aggregation inhibitors (e.g., Rember®); RAGE inhibitors (e.g., TTP 488 (PF-4494700)); anti-Abeta vaccine; APP ligands; agents that upregulate insulin, cholesterol lowering agents such as HMG-CoA reductase inhibitors (for example, statins such as Atorvastatin, Fluvastatin, Lovastatin, Mevastatin, Pitavastatin, Pravastatin, Rosuvastatin, Simvastatin) and/or cholesterol absorption inhibitors (such as Ezetimibe), or combinations of HMG-CoA reductase inhibitors and cholesterol absorption inhibitors (such as, for example, Vytorin®); fibrates (such as, for example, clofibrate, Clofibride, Etofibrate, and Aluminium Clofibrate); combinations of fibrates and cholesterol lowering agents and/or cholesterol absorption inhibitors; nicotinic receptor agonists; niacin; combinations of niacin and cholesterol absorption inhibitors and/or cholesterol lowering agents (e.g., Simcor® (niacin/simvastatin, available from Abbott Laboratories, Inc.); LXR agonists; LRP mimics; H3 receptor antagonists; histone deacetylase inhibitors; hsp90 inhibitors; 5-HT4 agonists (e.g., PRX-03140 (Epix Pharmaceuticals)); 5-HT6 receptor antagonists; mGluR1 receptor modulators or antagonists; mGluR5 receptor modulators or antagonists; mGluR2/3 antagonists; Prostaglandin EP2 receptor antagonists; PAI-1 inhibitors; agents that can induce Abeta efflux such as gelsolin; Metal-protein attenuating compound (e.g, PBT2); and GPR3 modulators; and antihistamines such as Dimebolin (e.g., Dimebon®, Pfizer); or other drugs that affect receptors or enzymes that either increase the efficacy, safety, convenience, or reduce unwanted side effects or toxicity of the compounds of the present invention.

Examples of combinations of the compounds include combinations with agents for the treatment of schizophrenia, for example in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, aiprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproelone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisuipride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, frihexyphenidyl, thioridazine, thiothixene, trifluoperazine or ziprasidone.

Examples of combinations of the compounds include combinations with agents for the treatment of pain, for example non-steroidal anti-inflammatory agents, such as aspirin, diclofenac, duflunisal, fenoprofen, flurbiprofen, ibuprofen, indomethacin, ketoprofen, ketorolac, naproxen, oxaprozin, piroxicam, sulindac and tolmetin; COX-2 inhibitors, such as celecoxib, rofecoxib, valdecoxib, 406381 and 644784; CB-2 agonists, such as 842166 and SAB378; VR-1 antagonists, such as AMG517, 705498, 782443, PAC20030, V114380 and A425619; bradykinin B1 receptor antagonists, such as SSR240612 and NVPSAA164; sodium channel blockers and antagonists, such as VX409 and SPI860; nitric oxide synthase (NOS) inhibitors (including iNOS and nNOS inhibitors), such as SD6010 and 274150; glycine site antagonists, including lacosamide; neuronal nicotinic agonists, such as ABT 894; NMDA antagonists, such as AZD4282; potassium channel openers; AMPA/kainate receptor antagonists; calcium channel blockers, such as ziconotide and NMED160; GABA-A receptor IO modulators (e.g., a GABA-A receptor agonist); matrix metalloprotease (MMP) inhibitors; thrombolytic agents; opioid analgesics such as codeine, fentanyl, hydromorphone, levorphanol, meperidine, methadone, morphine, oxycodone, oxymorphone, pentazocine, propoxyphene; neutrophil inhibitory factor (NIF); pramipexole, ropinirole; anticholinergics; amantadine; monoamine oxidase B15 ("MAO-B") inhibitors; 5HT receptor agonists or antagonists; mGlu5 antagonists, such as AZD9272; alpha agonists, such as AGNXX/YY; neuronal nicotinic agonists, such as ABT894; NMDA receptor agonists or antagonists, such as AZD4282; NM antagonists; selective serotonin reuptake inhibitors ("SSRI") and/or selective serotonin and norepinephrine reuptake inhibitors ("SSNRI"), such as duloxetine; tricyclic antidepressant drugs, norepinephrine modulators; lithium; valproate; gabapentin; pregabalin; rizatriptan; zolmitriptan; naratriptan and sumatriptan.

The compounds of the present invention may be administered in combination with compounds useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, orexin antagonists, alpha-1 antagonists, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, orexin antagonists, orexin agonists, prokineticin agonists and antagonists, pyrazolopyrimidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, filorexant, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, suvorexant, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. The subject or patient to whom the compounds of the present invention is administered is generally a human being, male or female, but may also encompass other mammals, such as dogs, cats, mice, rats, cattle, horses, sheep, rabbits, monkeys, chimpanzees or other apes or primates, for which treatment of the above noted disorders is desired.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives. Pharmaceutical compositions of the present compounds may be in the form of a sterile injectable aqueous or oleagenous suspension. Pharmaceutical compositions of the present compounds in the form of a sterile injectable aqueous or oleagenous suspension may be formulated by known techniques for depo administration and thereby provide a sustained action over a longer period. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

Several methods for preparing the compounds of this invention are illustrated in the following Schemes and Examples. Starting materials are made according to procedures known in the art or as illustrated herein. The following abbreviations are used herein: Me: methyl; Et: ethyl; t-Bu: tert-butyl; Ar: aryl; Ph: phenyl; aq: aqueous; BINAP: 2,2'-bis(diphenylphosphino)-1,1'-binaphthyl; Bn: benzyl; Ac: acetyl; Boc: tert-butyloxy carbonyl; BSA: bovine serum albumin; CAN: acetonitrile; Cbz: carboxylbenzyl; CbzCl: benzylchloroformate; CDI: carbonyl diimidazole; DABCO: 1,4-diazabicyclo[2.2.2]octane; DAST: diethylaminosulfur trifluoride; DBAD: di-tert-butyl azodicarboxylate; DCM: dichloromethane; DCE: dichloroethane; DEA: diethylamine; DEAD: diethylazodicarboxylate; DIAD: diisopropyl azodicarboxylate; DIBAL: diisobutylaluminium hydride; DIPEA: N,N-diisopropylethylamine; DMAP: 4-dimethylaminopyridine; DMF: N,N-dimethylformamide; DMP: Dess-Martin periodinane; DMS: dimethylsulfide; DMSO: dimethylsulfoxide; dppf: 1,1'-bis(diphenyl-phosphino)ferrocene; CH2Cl2: dichloromethane; EDC: N-(3-Dimethylaminopropyl)-N'-ethylcarbodiimide; Et3N: triethylamine; EtOAc: ethyl acetate; EtOH: ethanol; F-TEDA: Selectfluor®; HATU: (1-[bis(dimethylamino)methylene]-1H-1,2,3-triazolo[4,5-b]pyridinium 3-oxid hexafluorophosphate); HCl: hydrogen chloride; HOAt: 1-hydroxy-7-aza-benzotriazole; HOBT: hydroxybenzotriazole hydrate; HPLC: high performance liquid chromatography; Hunig's base: N,N-diisopropylethylamine; LDA: diisopropylamine; LHMDS: lithium bis(trimethylsilyl)amide; mCPBA: meta-chloroperbenzoic acid; MeOH: methanol; MgSO4: magnesium sulfate; Ms: methanesulfonyl; MTBE: methyl tert-butyl ether; MS: Mass spectra; NaHCO3: sodium bicarbonate; NaOH: sodium hydroxide; NBS: N-bromosuccinimide; NCS: N-chlorosuccinimide; NMM: N-methylmorpholine; NMR: nuclear magnetic resonance; PG: protecting group; PtO2: platinum oxide;PCC: pyridinium chlorochromate; rt: room temperature; SEM: 2-(Trimethylsilyl)ethoxylmethyl; SFC: supercritical fluid chromatography; SOCl2: thionyl chloride; T3P: 2,4,6-tripropyl-1,3,5,2,4,6-trioxatriphosphorinane-2,4,6-trioxide; TBAF: tetra-n-butylammonium fluoride; TBS: tert-Butyldimethylsilyl; TEA: triethylamine; TES: Triethylsilyl; TFA: trifluoroacetic acid; Tf: triflate; TFAA: trifluoroacetic anhydride; THF: tetrahydrofuran; TIPS: tri-isopropylsilyl; TLC: thin layer chromatography; Ts: toluenesulfonyl; X-Phos: 2-(dicyclohexyl-phosphino)-2',4',6'-triisopropyl-biphenyl.

The compounds of the present invention can be prepared in a variety of fashions. In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. Because the schemes are an illustration, the invention should not be construed as being limited by the chemical reactions and conditions expressed. The preparation of the various starting materials used herein is well within the skill of a person versed in the art. The following examples are provided so that the invention might be more fully understood. These examples are illustrative only and should not be construed as limiting the invention in any way. Absolute stereochemistry of separate stereoisomers in the examples and intermediates are not determined unless stated otherwise in an example or explicitly in the nomenclature.

SCHEME A

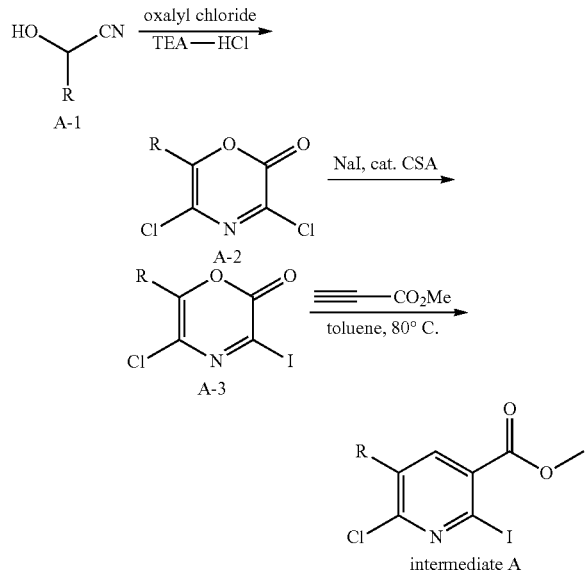

Intermediate A is prepared according to Scheme A via condensation of commercially available hydroxynitrile A-1 with oxalyl chloride to yield adduct A-2. A Finkelstein reaction of chloride A-2 with sodium iodide, catalyzed by camphorsulfonic acid (CSA) results in iodide product A-3. A hetero Diels-Alder reaction of diene A-3 with a commercially available ynone gives intermediate A.

INTERMEDIATE A1

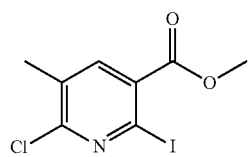

Methyl 6-chloro-2-iodo-5-methylnicotinate (Scheme A)

Step 1: 3,5-Dichloro-6-methyl-2H-1,4-oxazin-2-one

Into a 10-L 4-necked round-bottom flask was charged oxalic dichloride (3.32 kg, 26.2 mol) and chlorobenzene (3.5 L) under an inert atmosphere of nitrogen. A solution of 2-hydroxypropanenitrile (465 g, 6.54 mol) in chlorobenzene (500 mL) was added dropwise to the flask at 0° C. The system was heated to 90° C. and triethylamine hydrochloride (66.2 g, 481 mmol) was added in portions at 90° C. The resulting solution was stirred for 3 h before concentrating the mixture under reduced pressure. The resulting solution was diluted with ether (5 L) and the solids were filtered out. The filtrate concentrated and was then applied purified by silica gel column chromatography (0:1-1:4 ethyl acetate: petroleum ether) to yield the title compound.

Step 2:
5-Chloro-3-iodo-6-methyl-2H-1,4-oxazin-2-one

Into a 10-L 4-necked round-bottom flask was added 3,5-dichloro-6-methyl-2H-1,4-oxazin-2-one (471 g, 2.62 mol), acetone (10 L), NaI (1.57 kg, 10.5 mol) and camphorsulfonic acid (40 g, 172 mmol) under an atmosphere of nitrogen. The resulting solution was stirred for 3 h at 25° C. The mixture was concentrated and then diluted with water (20 L) and dichloromethane (3×5 L). The organic layers were combined and washed with brine (5 L). The mixture was dried over anhydrous sodium sulfate, filtered and was concentrated under reduced pressure to yield the title compound.

Step 3: Methyl 6-chloro-2-iodo-5-methylnicotinate

Into a 5-L 3-necked round-bottom flask was placed 5-chloro-3-iodo-6-methyl-2H-1,4-oxazin-2-one (638 g, 2.35 mol), toluene (2.3 L), and methyl prop-2-ynoate (592.8 g, 7.05 mol) under an atmosphere of nitrogen. The resulting solution was stirred for 2 days at 80° C. The reaction was cooled and the volatiles were removed under reduced pressure. The residue was purified by silica gel column chromatography (0:1-1:50 EtOAc:petroleum ether) to provide the major regioisomeric product as the title compound. MS: 312 (M+1).

The following intermediates in table A were prepared according to scheme A using the procedure outlined in the synthesis of intermediate A1 using commercially available hydroxynitriles in step 1.

TABLE A

| Intermediate | Structure | Name | MS (M + 1) |
|---|---|---|---|
| A2 | (structure) | methyl 6-chloro-5-ethyl-2-iodonicotinate | 326 |

SCHEME B

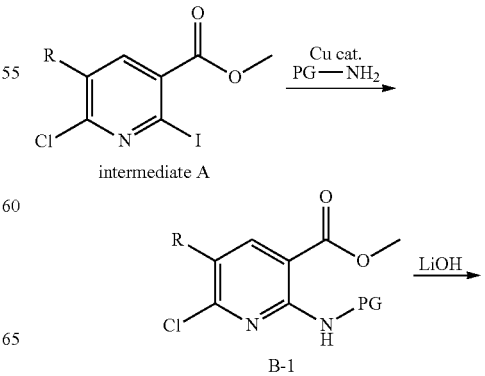

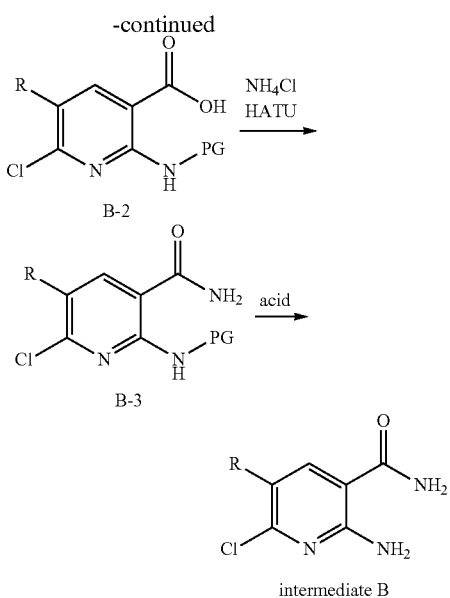

Intermediate B is prepared according to Scheme B via a copper-mediated C—N coupling reaction of commercially available amine and intermediate A to yield adduct B-1. Saponification followed by an amide coupling reaction with the corresponding acid B-2 forms amide B-3, which is deprotected under acidic conditions to yield carboxamide intermediate B.

INTERMEDIATE B1

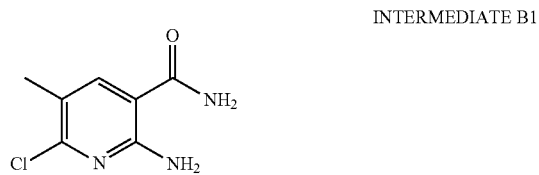

2-Amino-6-chloro-5-methylnicotinamide (Scheme B)

Step 1: Methyl 6-chloro-2-((2,4-dimethoxybenzyl)amino)-5-methylnicotinate

A solution of methyl 6-chloro-2-iodo-5-methylnicotinate (intermediate A1, 1.0 g, 3.21 mmol) and (2,4-dimethoxyphenyl)methanamine (1.88 g, 11.2 mmol) in DMF (8 mL) was added copper(I) iodide (0.306 g, 1.605 mmol) and sodium bicarbonate (0.674 g, 8.03 mmol). The mixture was stirred at 80° C. for 2 h under a nitrogen atmosphere. The mixture was diluted with water (10 mL), extracted with EtOAc (20 mL×3). The combined organics were then washed with water (30 mL×2), dried over anhydrous sodium sulfate, filtered, and concentrated under reduced pressure to give the title compound.

Step 2: 6-Chloro-2-((3,5-dimethoxybenzyl)amino)-5-methylnicotinic acid

To a mixture of methyl 6-chloro-2-((3,5-dimethoxybenzyl)amino)-5-methylnicotinate (500 mg, 1.43 mmol) in THF (5 mL) and water (5 mL) was added LiOH (68.3 mg, 2.85 mmol). The suspension was stirred at 15° C. for 2 h and was diluted with DCM (15 mL). The aqueous layer was adjusted to pH~5 with aqueous HCl (1 M) and was then extracted with EtOAc (15 mL×3). The combined organic phases were dried over anhydrous sodium sulfate, filtered and the filtrate was concentrated in vacuo to give the title compound.

Step 3: 6-Chloro-2-((2,4-dimethoxybenzyl)amino)-5-methylnicotinamide

To a mixture of 6-chloro-2-((2,4-dimethoxybenzyl)amino)-5-methylnicotinic acid (250 mg, 0.742 mmol), ammonium chloride (59.6 mg, 1.11 mmol) in DCM (15 mL) was added HATU (339 mg, 0.891 mmol) and DIPEA (0.130 mL, 0.742 mmol). The mixture was stirred at 15° C. for 2 h before the volatiles were removed under reduced pressure and the resultant residue was purified by silica gel chromatography (20%-50% EtOAc/petroleum ether) to afford the title compound.

Step 4: 2-Amino-6-chloro-5-methylnicotinamide

A mixture of 6-chloro-2-((3,5-dimethoxybenzyl)amino)-5-methylnicotinamide (0.17 g, 0.506 mmol) and TFA (0.975 mL, 12.7 mmol) in DCM (3 mL) was stirred at 15° C. for 2 h. The mixture was concentrated in vacuo and the residue was diluted with DCM (10 mL) and aqueous NaHCO$_3$ (saturated, 10 mL). The organic phase was dried over anhydrous Na$_2$SO$_4$, filtered and the filtrate was concentrated in vacuum to give a crude product. The residue was purified by silica gel chromatography (20%-70% EtOAc/petroleum ether) to give the title compound. MS: 186 (M+1).

The following intermediates in table B were prepared according to scheme B using the procedure outlined in the synthesis of intermediate B1.

TABLE B

| Intermediate | Structure | Name | MS (M + 1) |
|---|---|---|---|
| B2 | ![structure] | 2-amino-6-chloro-5-ethyl-nicotinamide | NMR data* |

*$^1$H NMR (400 MHz, DMSO-d$_6$): d 7.95 (1 H, br s), 7.90 (1 H, s), 7.35 (1 H, br s), 1.12 (3 H, t, J = 7.4 Hz).

SCHEME C

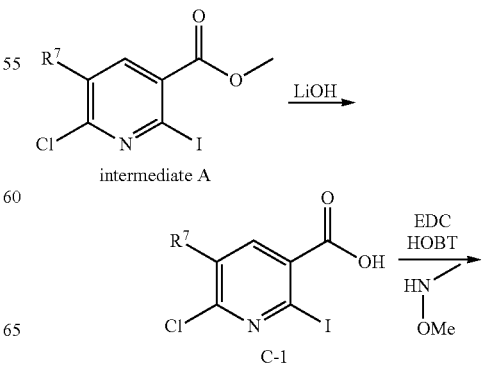

33
-continued

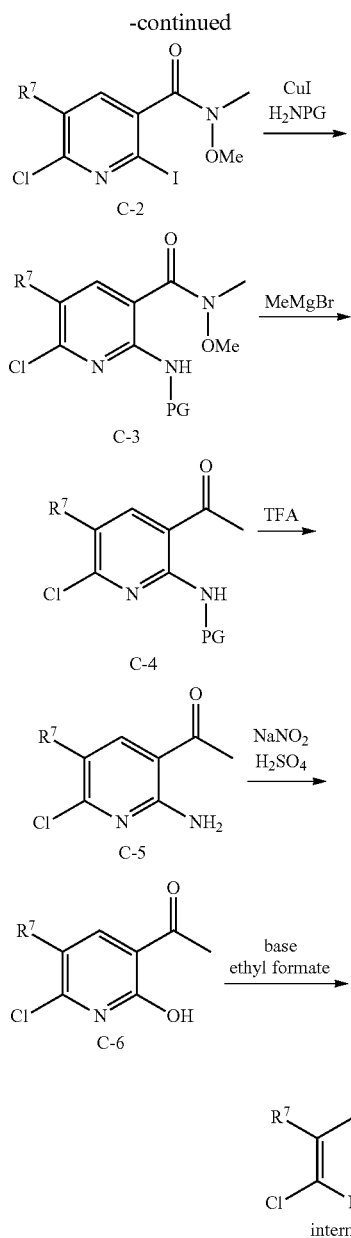

Intermediate C is prepared according to Scheme C via saponification of intermediate A to form acid C-1 was followed by an EDC-mediated coupling reaction to form Weinreb amide C-2. A Ullman-type coupling reaction with a protected amine yields adduct C-3. Ketone formation by reaction with methyl Grignard reagent is followed by deprotection to form aniline C-5. Diazotization of aniline C-5 leads to phenol C-6, which is cyclized via an aldol reaction with ethyl formate in the presence of base.

INTERMEDIATE C

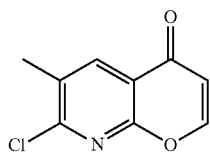

34

7-Chloro-6-methyl-4H-pyrano[2,3-b]pyridin-4-one (Scheme C)

Step 1: 6-Chloro-2-iodo-5-methylnicotinic acid

A mixture of methyl 6-chloro-2-iodo-5-methylnicotinate (intermediate A1, 2 g, 6.42 mmol) and lithium hydroxide (0.539 g, 12.84 mmol) in THF (10 mL) in water (5 mL) was stirred at RT for 1 h. The mixture was acidified with aqueous HCl (6 M) to pH~2 and then extracted with EtOAc (30 mL). The organic layer was dried over anhydrous sodium sulfate, filtered and the filtrate was concentrated to give the title compound.

Step 2: 6-Chloro-2-iodo-N-methoxy-N,5-dimethylnicotinamide

To a solution of TEA (2.68 mL, 19.26 mmol), N,O-dimethylhydroxylamine, HCl (0.939 g, 9.63 mmol), 6-chloro-2-iodo-5-methylnicotinic acid (1.910 g, 6.42 mmol) and HOBT (0.393 g, 2.57 mmol) in DCM (30 mL) was added EDC (1.48 g, 7.70 mmol). The reaction was stirred at 15° C. for 1 h and was then dissolved in DCM (30 mL), washed with water (30 mL), dried over anhydrous sodium sulfate, filtered and concentrated. The residue was purified by silica gel chromatography (70:30 petroleum ether: THF) to give the title compound.

Step 3: 6-Chloro-2-((2,4-dimethoxybenzyl)amino)-N-methoxy-N,5-dimethylnicotinamide A mixture of (2,4-dimethoxyphenyl)methanamine (1.33 g, 7.93 mmol), 6-chloro-2-iodo-N-methoxy-N,5-dimethylnicotinamide (1.80 g, 5.29 mmol), copper(I) iodide (0.302 g, 1.59 mmol) and sodium bicarbonate (1.33 g, 15.9 mmol) in DMF (25 mL) was stirred at 80° C. for 16 h under an atmosphere of nitrogen. The mixture was then cooled to RT and diluted with EtOAc (50 mL) and water (50 mL). The organic was washed with water (50 mL), dried over anhydrous sodium sulfate, filtrated and the filtrate was concentrated. The resultant residue was purified by silica gel chromatography (80:20 petroleum ether: THF) to afford the title compound.

Step 4: 1-(6-Chloro-2((2,4-dimethoxybenzyl) amino)-5-methylpyridin-3-yl)ethanone To a solution of 6-chloro-2-((2,4-dimethoxybenzyl) amino)-N-methoxy-N,5-dimethylnicotinamide (800 mg, 2.11 mmol) in THF (2 mL) was added methylmagnesium bromide (3 M in ether, 3.51 mL, 10.5 mmol) and the mixture was stirred at 0° C. for 10 min under an atmosphere of nitrogen. The reaction was quenched with HCl (1 M in water) and the pH was adjusted to ~3. The mixture was extracted with EtOAc and the organic layer was dried over anhydrous $Na_2SO_4$, filtered and the filtrate was concentrated. The residue was purified by silica gel chromatography (80:20 petroleum ether: THF) to give the title compound.

Step 5: 1-(2-Amino-6-chloro-5-methylpyridin-3-yl)ethanone

A mixture of 1-(6-chloro-2-((2,4-dimethoxybenzyl) amino)-5-methylpyridin-3-yl)ethanone (500 mg, 1.493 mmol) in TFA (10 mL) was stirred at 80° C. for 2 h. The mixture was concentrated, dissolved in DCM (20 mL), washed with aqueous NaHCO₃ (saturated, 20 mL), dried over anhydrous Na₂SO₄, filtered and the filtrate was concentrated. The residue was purified by silica gel chromatography (80:20 petroleum ether: THF) to afford the title compound.

Step 6: 1-(6-Chloro-2-hydroxy-5-methylpyridin-3-yl)ethanone

To a solution of 1-(2-amino-6-chloro-5-methylpyridin-3-yl)ethanone (150 mg, 0.812 mmol) in conc. H₂SO₄ (0.5 mL, 3.0 mmol) was added sodium nitrite (61.7 mg, 0.894 mmol). The reaction was stirred at 0° C. for 10 min before being neutralized with aqueous NaHCO₃ (saturated) at 0° C. After 1 h, the mixture was extracted with EtOAc (20 mL), the organic layer was dried over anhydrous Na₂SO₄, filtered and the filtrate was concentrated. The residue was purified by silica gel chromatography (80:20 petroleum ether: THF) to give the title compound.

Step 7: 7-Chloro-6-methyl-4H-pyrano[2,3-b]pyridin-4-one

To solution of 1-(6-chloro-2-hydroxy-5-methylpyridin-3-yl)ethanone (90 mg, 0.485 mmol) in ethyl formate (5 mL, 61.4 mmol) was added NaH (60%, 116 mg, 2.91 mmol) at 0° C. After 2 h, the mixture was acidified with aqueous HCl to pH~1 and was then stirred at 15° C. for 16 h. The mixture concentrated and purified by reverse phase HPLC (ACN/water with 0.1% HCl modifier) to afford the title compound. MS: 196 (M+1).

SCHEME D

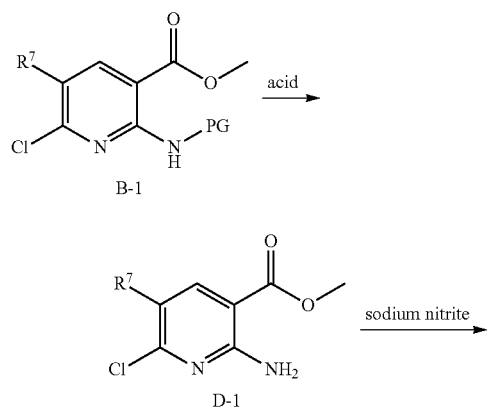

INTERMEDIATE D

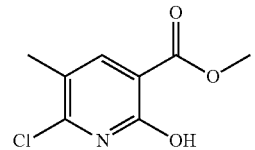

Methyl 6-chloro-2-hydroxy-5-methylnicotinate (Scheme D)

Step 1: Methyl 2-amino-6-chloro-5-methylnicotinate

A solution of methyl 6-chloro-2-((2,4-dimethoxybenzyl)amino)-5-methylnicotinate (1.2 g, 3.42 mmol) in DCM (10 mL) and TFA (2 mL) was stirred at 40° C. for 1 h. Aqueous NaHCO₃ (saturated) was added until the reaction mixture was pH~8. The mixture was extracted with EtOAc (20 mL×3) and the combined organic fractions were washed with water (40 mL), dried over anhydrous sodium sulfate, filtered and concentrated. The crude material was purified by silica gel chromatography (0-40% EtOAc/petroleum ether) to afford the title compound. MS: 201 (M+1).

Step 2: Methyl 6-chloro-2-hydroxy-5-methylnicotinate

A solution of methyl 2-amino-6-chloro-5-methylnicotinate (100 mg, 0.498 mmol) in aqueous HCl (6 M, 4 mL) and sodium nitrite (172 mg, 2.49 mmol) was stirred at 0° C. for 1 h. Aqueous NaHCO₃ (saturated) was added until the reaction mixture was pH~8. The mixture was extracted with EtOAc (10 mL×3) and the combined organic fractions were washed with water, dried over anhydrous sodium sulfate, filtered and concentrated to afford the title compound. MS: 202 (M+1)

SCHEME E

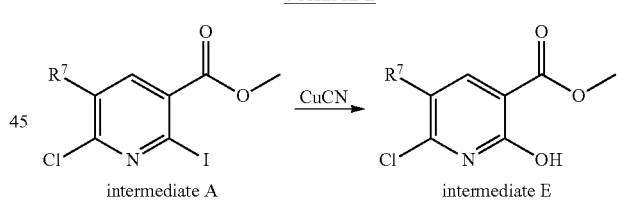

intermediate A      intermediate E

Intermediate E is prepared according to Scheme E from intermediate A via a copper-mediated cyanation to form intermediate E.

INTERMEDIATE E

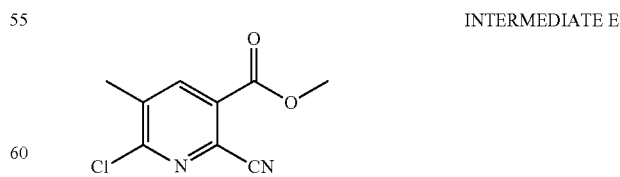

Methyl 6-chloro-2-cyano-5-methylnicotinate (Scheme E)

Into a 20-mL microwave tube was added methyl 6-chloro-2-iodo-5-methylpyridine-3-carboxylate (2 g, 6.42 mmol), Intermediate D is prepared according to Scheme D from pyridine B-1 that was prepared from the procedure outlined in Scheme B. Deprotection under acidic conditions yields aniline D-1 which is the precursor for diazotization by sodium nitrite to form intermediate D.

DMF (15 mL), and CuCN (850 mg, 9.60 mmol). The resulting solution was stirred for 5 min at 100° C. under microwave irradiation. The mixture was diluted with water (20 mL) and aqueous NH₄Cl (saturated, 100 mL). Dichloromethane (2×20 mL) was used to extract the crude material and the organic layers were combined and dried over anhydrous sodium sulfate, filtered and then concentrated. The residue was purified by silica gel chromatography (0:1-1:8 ethyl acetate:petroleum ether) to provide the title compound. MS: 211 (M+1).

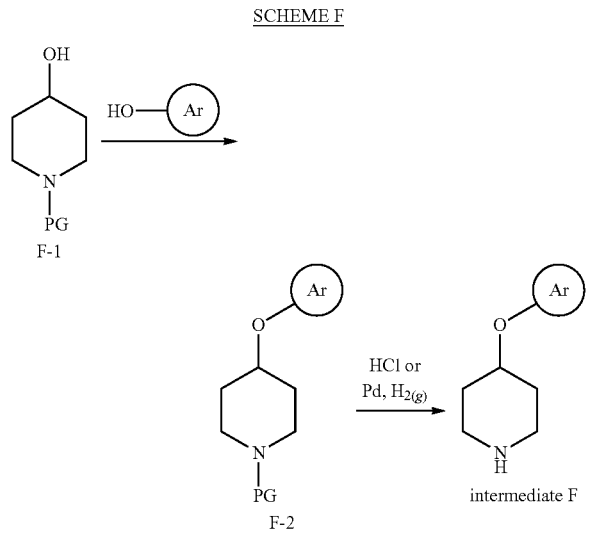

SCHEME F

Intermediate F is prepared according to scheme F via Mitsunobu reaction of commercially available N-protected piperdine F-1 with known or prepared phenols (wherein Ar is an aromatic or heteroaromatic ring of R¹) to yield adduct F-2. Subsequent deprotection of ether F-2 provides intermediate F.

added followed by the dropwise addition of DIAD (420 g, 2.08 mol) at RT. After stirring for 1 h at 40° C., the resulting solution was diluted with water (2 L) and was partitioned with EtOAc (4 L). The organic layers were combined, washed with brine (2 L), dried over anhydrous sodium sulfate, filtered and concentrated. The residue was purified by silica gel column chromatography (1/10 ethyl acetate/petroleum ether) to yield the title compound.

Step 2: 2-Methoxy-5-(piperidin-4-yloxy)pyridine dihydrochloride

A solution of tert-butyl 4-((6-methoxypyridin-3-yl)oxy) piperidine-1-carboxylate (270 g, 875.6 mmol) in methanol (2 L) was bubbled slowly with HCl (g). The resulting solution was stirred for 2 h at RT. The volatiles were removed and the crude material was diluted with hot EtOAc: MeOH (8:1) and was then cooled to obtain a precipitate that was collected by filtration to yield the title compound. ¹H NMR (300 MHz, D₂O): δ7.79-7.98 (m, 2H), 7.24-7.23 (m, 1H), 4.0 (s, 3H), 3.36-3.40 (m, 2H), 3.15-3.26 (m, 2H), 1.97-2.14 (m, 4H).

The following intermediates in table F were prepared according to scheme F using the procedure outlined in the synthesis of intermediate F1 using commercially available, known or prepared phenols in step 1 and employing various azodicarboxylates with TBAD or DIAD being the preferred reagents.

TABLE F

| Intermediate | Structure | Name | MS (M + 1) |
|---|---|---|---|
| F2 | 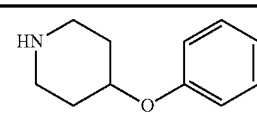 | 4-phenoxy-piperidine | 178 |
| F3 | 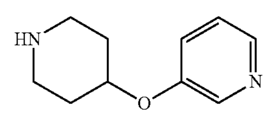 | 3-(piperidin-4-yloxy)pyridine | 179 |

INTERMEDIATE F1

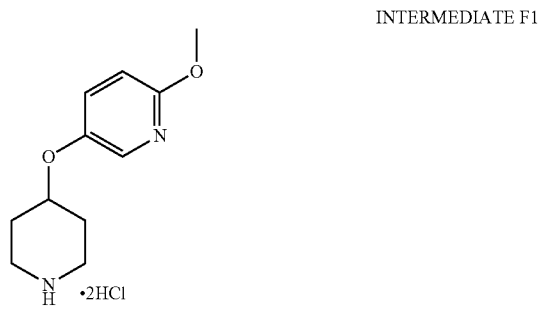

2-Methoxy-5-(piperidin-4-yloxy)pyridine dihydrochloride (Scheme F)

Step 1: tert-Butyl 4-((6-methoxypyridin-3-yl)oxy) piperidine-1-carboxylate

Into a 5-L 4-necked round-bottom flask purged and maintained with an inert atmosphere of nitrogen was placed a solution of 6-methoxypyridin-3-ol (200 g, 1.60 mol) in THF (1.5 L). tert-Butyl 4-hydroxypiperidine-1-carboxylate (386 g, 1.92 mol) and triphenylphosphine (545 g, 2.08 mol) were

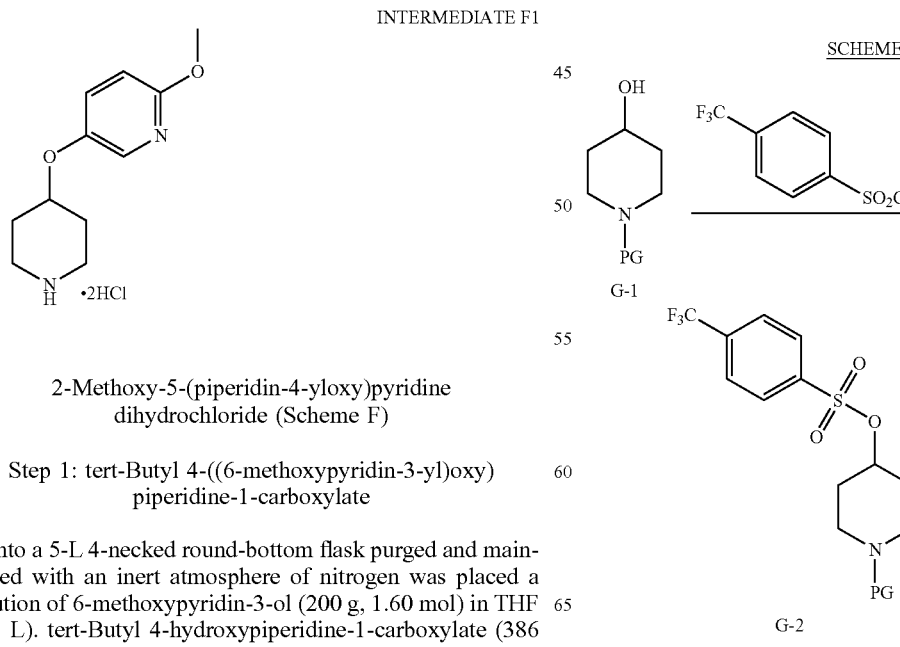

SCHEME G

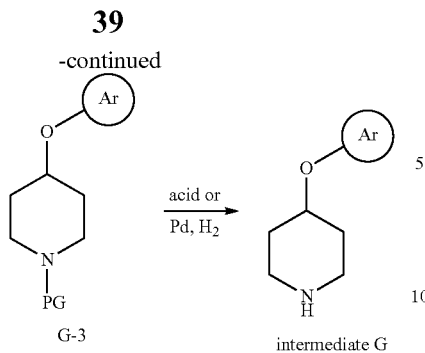

Intermediate G is prepared from a commercial alcohol G-1 (wherein PG is an amine protecting group), which after reaction with 4-(trifluoromethyl)benzenesulfonyl chloride forms adduct G-2. Displacement of sulfone G-2 by a known or prepared phenol or alcohol (wherein Ar is an aromatic or heteroaromatic ring of $R^1$) is carried out under the action of $K_3PO_4$ or $Cs_2CO_3$ to provide ether G-3. Deprotection under acidic or reductive conditions provides intermediate G.

INTERMEDIATE G1

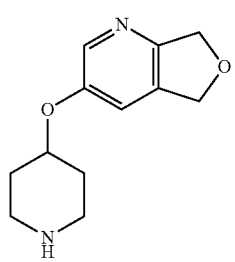

3-(Piperidin-4-yloxy)-5,7-dihydrofuro[3,4-b]pyridine (Scheme G)

Step 1: Benzyl 4-(((4-(trifluoromethyl)phenyl)sulfonyl)oxy)piperidine-1-carboxylate A solution of benzyl 4-hydroxypiperidine-1-carboxylate (200 g, 808 mmol) and DCM (2 L) was cooled below 10° C. 4-(Trifluoromethyl)benzenesulfonyl chloride (296 g, 1.21 mol) was added to the mixture followed by triethylamine (169 mL, 1.21 mol) and 4-dimethylaminopyridine (9.87 g, 81 mmol). The reaction was aged at 5° C. and slowly warmed to RT. The reaction was aged 14 h and was transferred to separatory funnel containing an aqueous 10% citric acid solution. The organic was dried over anhydrous $Na_2SO_4$ before concentrating to dryness. The residue was purified by silica gel column (0-50% EtOAc/hexanes) to give the title compound.

Step 2: Benzyl 4-((1,3-dihydro-2-benzofuran-5-yl)oxy)piperidine-1-carboxylate

To a flask was added benzyl 4-(((4(trifluoromethyl)phenyl)sulfonyl)oxy)piperidine-1-carboxylate (50.9 g, 115 mmol), 5,7-dihydrofuro[3,4-b]pyridin-3-ol (10.5 g, 77 mmol) and a fine powder of potassium tribasic phosphate (24.4 g, 115 mmol) and MeCN (100 mL). After being stirred at 60° C. for an appropriate period, the mixture was cooled and poured into water and then extracted with EtOAc. The organic layer was dried over anhydrous $Na_2SO_4$ before concentrating to dryness. The residue was purified by silica gel column (50% EtOAc/hexanes) to give the title compound.

Step 3: 4-((1,3-Dihydro-2-benzofuran-5-yl)oxy)piperidine

To a solution of benzyl 4-((5,7-dihydrofuro[3,4-b]pyridin-3-yl)oxy)piperidine-1-carboxylate (21 g, 59.3 mmol) in methanol (200 mL) was added Pearlman's Catalyst (4.16 g, 5.93 mmol) under an atmosphere of $N_2(g)$. The system was purged and was placed under an atmosphere of $H_2(g)$ with stirring at RT. Upon completion, the reaction was filtered and the filtrate was concentrated to provide the title compound, which was carried forward without further purification. MS: 221 (M+1).

SCHEME H

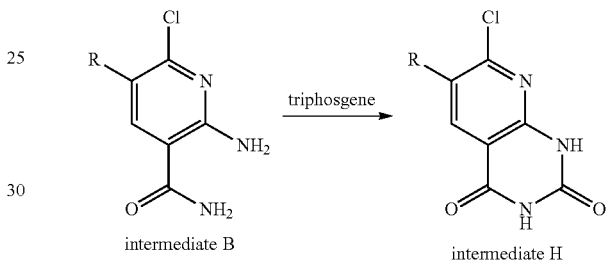

Intermediate H is prepared from intermediate B after treatment with triphosgene.

INTERMEDIATE H1

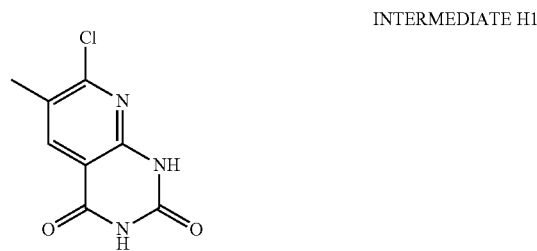

7-Chloro-6-methylpyrido[2,3-d]pyrimidine-2,4(1H,3H)-dione (Scheme H)

To a mixture of 2-amino-6-chloro-5-methylnicotinamide (intermediate B1, 50 mg, 0.269 mmol) in dioxane (2 mL) was added bis(trichloromethyl) carbonate (48.0 mg, 0.162 mmol). The reaction was stirred at 100° C. for 2 h and the cooled mixture was poured into water (5 mL), then extracted with EtOAc (5 mL×3). The combined organic layers were washed with brine (10 mL×3), dried over anhydrous $Na_2SO_4$, filtered and the filtrate was concentrated to afford the title compound. MS: 212 (M+1).

The following intermediates in table H were prepared according to scheme H using the procedure outlined in the synthesis of intermediate H1.

TABLE H

| Intermediate | Structure | Name | MS (M + 1) |
|---|---|---|---|
| H2 | 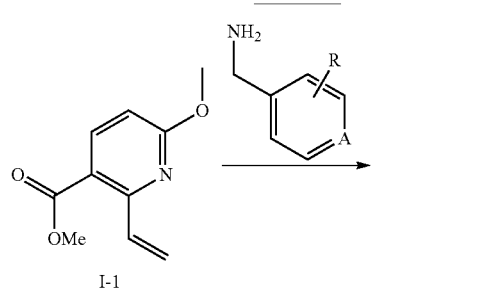 | 7-chloro-6-ethylpyrido[2,3-d]pyrimidine-2,4(1H,3H)-dione | 226 |

SCHEME I

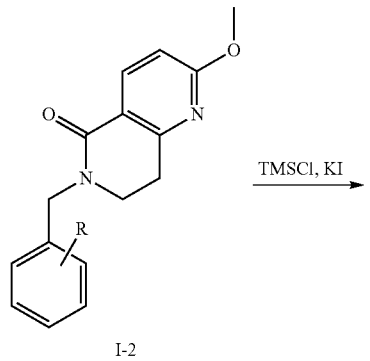

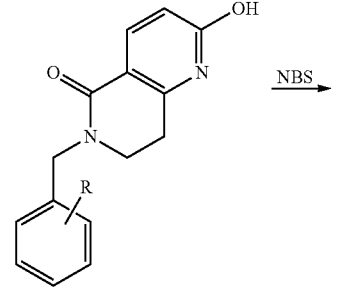

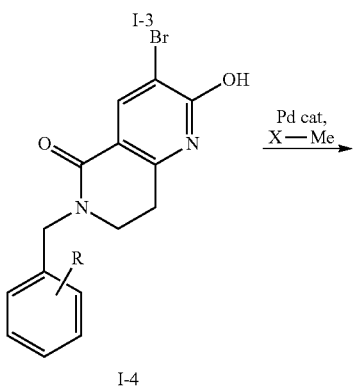

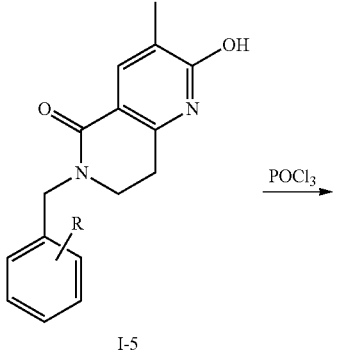

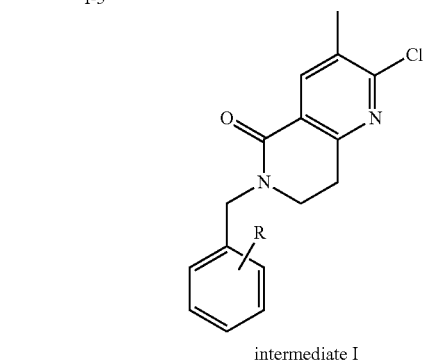

intermediate I

Intermediate I is prepared from known ester I-1 (prepared according to literature, see: Turlington, M., et al. *J. Med. Chem.* 2014, 13, 5620-5637) and is transformed to the corresponding cyclic amide I-2 after reaction with a benzyl amine. Demethylation of ether I-2 yields phenol I-3, which is then subject to electrophilic bromination to form bromide I-4. A palladium-mediated coupling reaction with a organometallic methylating reagent provides phenol I-5 which is subsequently treated with phosphoryl chloride to provide intermediate I.

INTERMEDIATE I1

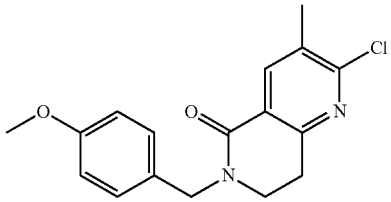

2-Chloro-6-(4-methoxybenzyl)-3-methyl-7,8-dihydro-1,6-naphthyridin-5(6H)-one (Scheme I)

Step 1: 2-Methoxy-6-(4-methoxybenzyl)-7,8-dihydro-1,6-naphthyridin-5(6H)-one

A mixture of methyl 6-methoxy-2-vinylnicotinate (3.2 g, 16.56 mmol), 4-methoxybenzylamine (5.68 g, 41.4 mmol) and DMA (10 mL) was heated for 40 min in a microwave reactor at 150° C. The mixture was then filtered, concentrated and was purified by silica gel chromatography (3:1 petroleum ether:EtOAc) to give the title compound.

Step 2: 2-Hydroxy-6-(4-methoxybenzyl)-7,8-dihydro-1,6-naphthyridin-5(6H)-one To a solution of 2-methoxy-6-(4-methoxybenzyl)-7,8-dihydro-1,6-naphthyridin-5 (6H)-one (2.8 g, 9.39 mmol) and KI (4.67 g, 28.2 mmol) in DCM (100 mL) was added TMSCl (2.40 mL, 18.77 mmol) dropwise at 0° C. The mixture was stirred at 0° C. for 30 min and then aged at RT for 12 h. The reaction was diluted with aqueous Na₂S₂O₃ (saturated, 50 mL) and extracted with DCM (50 mL×3). The organic layers were combined, washed with brine (50 mL), dried over anhydrous magnesium sulfate, filtered, and concentrated in vacuo to afford the title compound.

Step 3: 3-Bromo-2-hydroxy-6-(4-methoxybenzyl)-7,8-dihydro-1,6-naphthyridin-5(6H)-one To a solution of 2-hydroxy-6-(4-methoxybenzyl)-7,8-dihydro-1,6-naphthyridin-5 (6H)-one (2 g, 7.03 mmol) in chloroform (60 mL) was added NBS (1.50 g, 8.44 mmol) at 20° C. The mixture was stirred at RT for 16 h after which time the reaction was concentrated under reduced pressure. The residue was purified by silica gel chromatography (ethyl acetate) to afford the title compound.

Step 4: 2-Hydroxy-6-(4-methoxybenzyl)-3-methyl-7,8-dihydro-1,6-naphthyridin-5(6H)-one To a solution of 3-bromo-2-hydroxy-6-(4-methoxybenzyl)-7,8-dihydro-1,6-naphthyridin-5(6H)-one (500 mg, 1.377 mmol) and Pd(Ph₃P)₄ (477 mg, 0.413 mmol) in toluene (5 mL) was added trimethylaluminum (2 M, 2.75 mL, 5.51 mmol) under an inert nitrogen atmosphere. The mixture was stirred at 90° C. for 16 h before being quenched with water (50 mL) and extracted with EtOAc (50 mL×6). The combined organic layers were dried over anhydrous sodium sulfate, filtered, and concentrated to yield the title compound, which was used without further purification.

Step 5: 2-Chloro-6-(4-methoxybenzyl)-3-methyl-7,8-dihydro-1,6-naphthyridin-5(6H)-one To a mixture of 2-hydroxy-6-(4-methoxybenzyl)-3-methyl-7,8-dihydro-1,6-naphthyridin-5(6H)-one (300 mg, 1.00 mmol) in toluene (50 mL) was added POCl₃ (0.469 mL, 5.03 mmol). The reaction was stirred at 80° C. for 16 h before being concentrated under reduced pressure. The residue was purified by silica gel chromatography (3:1 petroleum ether:EtOAc) to give the title compound. MS: 317 (M+1).

The following intermediates in table I were prepared according to scheme I using the procedure outlined in the synthesis of intermediate I1 using commercially available benzylamines.

SCHEME J

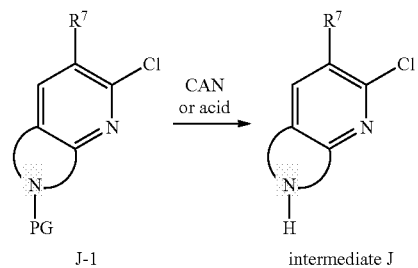

Intermediate J is prepared according to Scheme J from prepared N-protected amine or amide J-1 after treatment with CAN or acid to yield the deprotected amine or amide.

INTERMEDIATE J

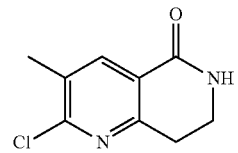

2-Chloro-3-methyl-7,8-dihydro-1,6-naphthyridin-5 (6H)-one (Scheme J)

To a solution of 2-chloro-6-(4-methoxybenzyl)-3-methyl-7,8-dihydro-1,6-naphthyridin-5(6H)-one (intermediate I1, 200 mg, 0.631 mmol) in acetonitrile (20 mL) and water (5 mL) was added ceric ammonium nitrate (1.38 g, 2.53 mmol) at 0° C. The reaction was stirred at RT for 16 h and was quenched with water (10 mL). The mixture was extracted with EtOAc (10 mL×3) and the combined organic layers were dried over anhydrous sodium sulfate, filtered and concentrated. The residue was purified by prep-TLC (1:1 petroleum ether:EtOAc) to afford the title compound. MS: 197 (M+1).

SCHEME K

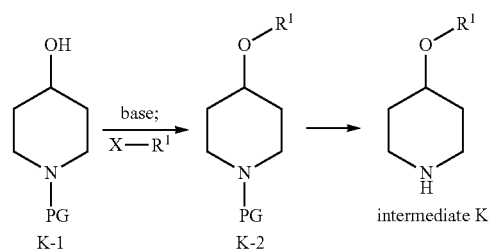

TABLE I

| Intermediate | Structure | Name | MS (M + 1) |
|---|---|---|---|
| I2 | ![structure] | 2-chloro-3-methyl-6-(pyridin-4-ylmethyl)-7,8-dihydro-1,6-naphthyridin-5(6H)-one | 288 |

Intermediate K is prepared according to Scheme K from N-protected piperidine alcohol K-1 in a two-step procedure involving base-mediated alkylation to form adduct K-2 and subsequent deprotection to reveal the piperidine amine.

INTERMEDIATE K

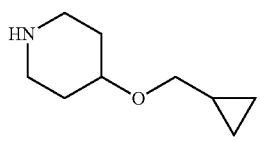

4-(Cyclopropylmethoxy)piperidine (Scheme K)

Step 1: tert-Butyl 4-(cyclopropylmethoxy)piperidine-1-carboxylate

To a solution of tert-butyl 4-hydroxypiperidine-1-carboxylate (400 mg, 1.987 mmol) in DMF (4 mL) was added sodium hydride (60%, 95 mg, 2.39 mmol) at 0° C. The reaction was stirred for 1 h before (bromomethyl)cyclopropane (322 mg, 2.39 mmol) and sodium iodide (14.90 mg, 0.099 mmol) were added. The reaction was stirred for 20 h at RT and then the mixture was treated with water (25 mL) and extracted with DCM (25 mL×3). The combined organic layers were dried over anhydrous sodium sulfate, filtered and concentrated. The residue was purified by silica gel chromatography (0-25% THF/petroluem ether) to give the title compound.

Step 2: 4-(Cyclopropylmethoxy)piperidine

A solution of tert-butyl 4-(cyclopropylmethoxy)piperidine-1-carboxylate (290 mg, 1.136 mmol) in 4 M HCl in EtOAc (3 mL) was stirred at RT for 1 h. Volatiles were removed from the reaction under reduced pressure. The residue was dissolved in MeOH (2 mL) and basified by aqueous NaHCO$_3$ (saturated) to pH~8. The mixture was concentrated and the residue was treated with EtOAc (5 mL), filtered and concentrated to afford the title compound. $^1$H NMR (400 MHz, CDCl$_3$): δ3.50-3.53 (1H, m), 3.28 (2H, d, J=6.8 Hz), 3.17-3.21 (2H, m), 2.87-2.90 (2H, m), 1.99-2.04 (2H, m), 1.67-1.71 (2H, m), 1.06-1.03 (1H, m), 0.52-0.57 (2H, m), 0.17-0.21 (2H, m).

The following intermediates in table K were prepared according to scheme K using the procedure outlined in the synthesis of intermediate K1 using commercially available or prepared alkyl halides, mesylates or tosylates. In cases where additional chemical manipulation are to be carried out on the intermediate, the second step may be omitted.

TABLE K

| Intermediate | Structure | Name | MS (M + 1) |
|---|---|---|---|
| K2 | Cbz-N-piperidine-O-CH$_2$-C(CH$_3$)=CH$_2$ | benzyl 4-((2-methylallyl)oxy)piperidine-1-carboxylate | 290 |
| K3 | HN-piperidine-O-CH$_2$-cyclobutyl | 4-(cyclobutylmethoxy)piperidine | 170 |
| K4 | HN-piperidine-O-CH$_2$-cyclopentyl | 4-(cyclopentylmethoxy)piperidine | NMR data[1] |
| K5 | HN-piperidine-O-CH$_2$-cyclohexyl | 4-(cyclohexylmethoxy)piperidine | NMR data[2] |

[1] $^1$H NMR (400 MHz, methanol-d$_4$): δ 3.59-3.68 (m, 1 H), 3.35 (d, J = 6.80 Hz, 2 H), 3.20-3.25 (m, 2 H), 3.03-3.14 (m, 2 H), 2.09-2.16 (m, 1 H), 1.91-2.03 (m, 2 H), 1.81-1.88 (m, 2 H), 1.67-1.75 (m, 2 H), 1.45-1.65 (m, 4 H), 1.16-1.36 (m, 2 H).
[2] $^1$H NMR (400 MHz, methanol-d$_4$): δ 3.61 (br s, 1 H), 3.31-3.26 (m, 4 H), 3.12-3.09 (m, 2 H), 2.01-1.98 (m, 2 H), 1.88-1.72 (m, 7 H), 1.68 (br s, 1 H), 1.30-1.21 (m, 3 H), 1.03-0.97 (m, 2H).

SCHEME L

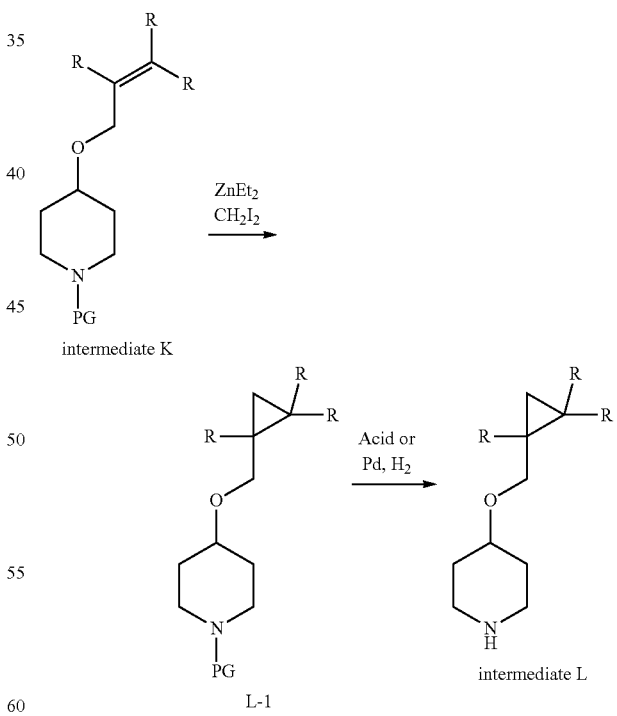

Intermediate L is prepared according to Scheme L from N-protected piperidine alcohol intermediate K in a two-step procedure involving Simmons-Smith reaction to form adduct L-1 and subsequent deprotection to reveal the piperidine amine.

INTERMEDIATE L1

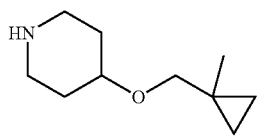

4-((1-Methylcyclopropyl)methoxy)piperidine (Scheme L)

Step 1: Benzyl 4-((1-methylcyclopropyl)methoxy)piperidine-1-carboxylate

To a solution of benzyl 4-((2-methylallyl)oxy)piperidine-1-carboxylate (9 g, 31.1 mmol) in DCM (100 mL) was added diiodomethane (41.7 g, 156 mmol) and diethylzinc (93 ml, 93 mmol) at −5° C. for 3 h. The reaction mixture was diluted with water (100 mL) and extracted with EtOAc (100 mL×3). The combined organic layers were washed with brine (80 mL), dried over anhydrous sodium sulfate, filtered and the filtrate was concentrated in vacuo.

The residue was purified by chromatography column (15% EtOAc/petroleum ether) to give the title compound.

Step 2: 4-((1-Methylcyclopropyl)methoxy)piperidine

To a solution of benzyl 4-((1-methylcyclopropyl)methoxy)piperidine-1-carboxylate (1 g, 3.30 mmol) in MeOH (10 mL) was added Pd/C (10 wt %, 3.51 g, 3.30 mmol). The reaction was stirred under an atmosphere of $H_2$ (15 psi) at RT for 1 h. The mixture was filtered and the filtrate was concentrated in vacuo to yield the title compound. MS: 170 (M+1).

SCHEME M

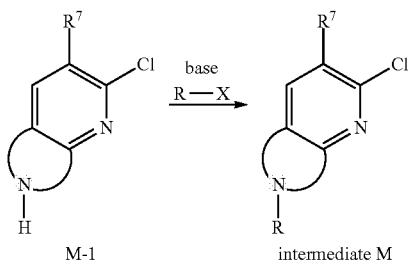

Intermediate M is prepared according to scheme M from prepared amine or amide M-1 after reaction with an alkyl halide in the presence of base.

INTERMEDIATE M1

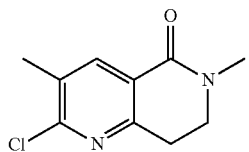

2-Chloro-3,6-dimethyl-7,8-dihydro-1,6-naphthyridin-5(6H)-one (Scheme M)

To a solution of 2-chloro-3-methyl-7,8-dihydro-1,6-naphthyridin-5(6H)-one (30 mg, 0.153 mmol) was added NaH (60%, 12.2 mg, 0.305 mmol) at 0° C. The mixture was stirred at 0° C. for 0.5 h before MeI (0.014 mL, 0.229 mmol) was added and the system was allowed to warm to RT and stir for 16 h. The mixture was diluted with water (20 mL), extracted with EtOAc (20 mL×3), the combined organic phased were then washed with brine (20 mL), dried over anhydrous magnesium sulfate, filtered, and concentrated. The residue was purified by prep-TLC (1:1 petroleum ether: EtOAc) to give the title compound. MS: 211 (M+1).

The following intermediates in table M were prepared according to scheme M using the procedure outlined in the synthesis of intermediate M1.

TABLE M

| Intermediate | Structure | Name | MS (M + 1) |
| --- | --- | --- | --- |
| M2 | ![structure] | 2-chloro-3,6-dimethylpyrido[2,3-d]pyridazin-5(6H)-one | 210 |
| M3 | ![structure] | 7-chloro-2,3,6-trimethylpyrido[2,3-d]pyrimidin-4(3H)-one | 224 |

SCHEME N

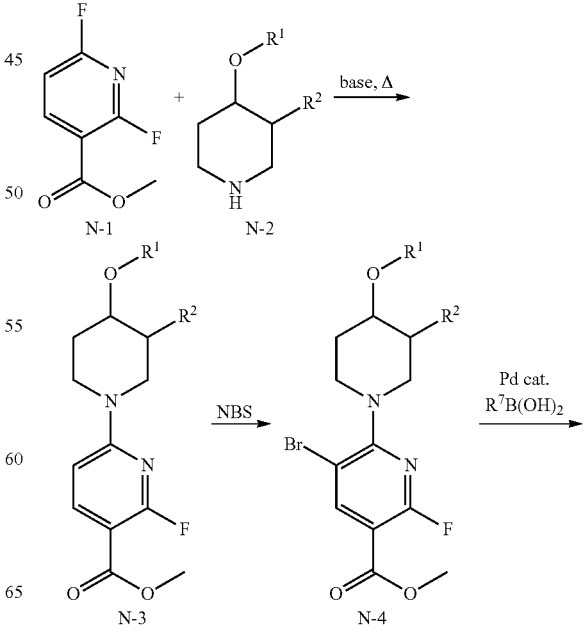

-continued

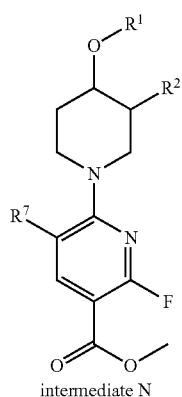

intermediate N

Intermediate N is prepared according to scheme N from an S$_N$Ar reaction of commercial 2-fluoropyridine N-1 with prepared or known piperidine N-2. Adduct N-3 is reacted with NBS to provide the brominated product N-4, which is subsequently functionalized via a Suzuki coupling reaction.

INTERMEDIATE N1

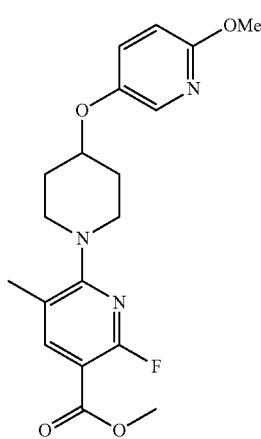

Methyl 2-fluoro-6-(4-((6-methoxypyridin-3-yl)oxy) piperidin-1-yl)-5-methylnicotinate (Scheme N)

Step 1: Methyl 2-fluoro-6-(4-((6-methoxypyridin-3-yl)oxy)piperidin-1-yl)nicotinate To a solution of methyl 2,6-difluoronicotinate (800 mg, 4.62 mmol) and DIPEA (4.04 mL, 23.1 mmol) in DMF (10 mL) was added 2-methoxy-5-(piperidin-4-yloxy)pyridine, HCl (1.24 g, 5.08 mmol) at 0° C. The reaction mixture was stirred at 0° C. for 1 h before diluting with water (15 mL) and extracting with EtOAc (20 mL×4). The combined organic phases were washed with water (50 mL×3), dried over anhydrous sodium sulfate, filtered and concentrated. The crude residue was purified by silica gel chromatography (0-30% EtOAc/petroleum ether) to give the title compound.

Step 2: Methyl 5-bromo-2-fluoro-6-(4-((6-methoxypyridin-3-yl)oxy)piperidin-1-yl)nicotinate To a solution of methyl 2-fluoro-6-(4-((6-methoxypyridin-3-yl)oxy)piperidin-1-yl)nicotinate (850 mg, 2.35 mmol) in chloroform (10 mL) was added NBS (502 mg, 2.82 mmol). The reaction mixture was stirred at 80° C. for 2 h. The solvent was evaporated under reduced pressure to give crude material which was purified by silica gel chromatography (0-30% EtOAc/petroleum ether) to afford the title compound.

Step 3: Methyl 2-fluoro-6-(4-((6-methoxypyridin-3-yl)oxy)piperidin-1-yl)-5-methylnicotinate To a solution of methyl 5-bromo-2-fluoro-6-(4-((6-methoxypyridin-3-yl)oxy)piperidin-1-yl)nicotinate (950 mg, 2.16 mmol), tribasic potassium phosphate (1.37 g, 6.47 mmol) and methylboronic acid (258 mg, 4.32 mmol) in THF (5 mL) and water (1 mL) was added 1,1'-bis(di-tert-butylphosphino)ferrocene palladium dichloride (141 mg, 0.216 mmol) under an inert nitrogen atmosphere. The reaction was stirred at 70° C. for 15 h. The mixture was cooled to RT and diluted with water (10 mL) and EtOAc (30 mL). The organic phase was dried over anhydrous sodium sulfate, filtered and the solvent was evaporated under reduced pressure. The resultant residue was purified by silica gel chromatography (0-30% EtOAc/petroleum ether) to afford the title compound. MS: 376 (M+1).

The following intermediates in table N were prepared according to scheme N using the procedure outlined in the synthesis of intermediate N1.

TABLE N

| Intermediate | Structure | Name | MS (M + 1) |
|---|---|---|---|
| N2 | 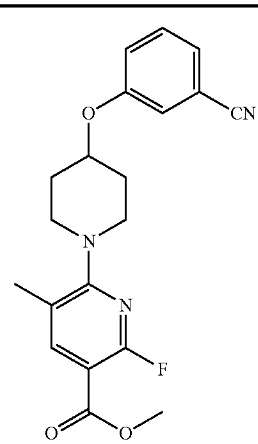 | methyl 6-(4-(3-cyanophenoxy)piperidin-1-yl)-2-fluoro-5-methylnicotinate | 356 |

SCHEME O

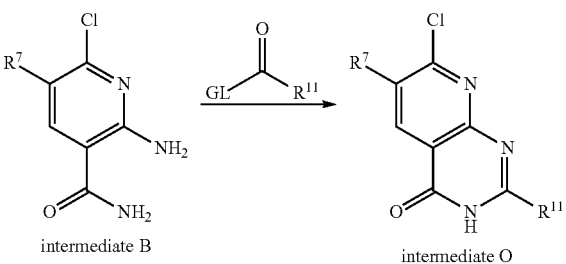

Intermediate O is prepared from intermediate B after condensation with an aldehyde (ie. formamide), aldehyde equivalent (triethyl orthoacetate) or acyl chloride.

INTERMEDIATE O1

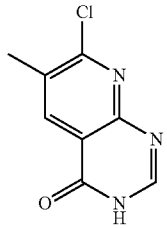

7-Chloro-6-methylpyrido[2,3-d]pyrimidin-4(3H)-one (Scheme O)

A solution of 2-amino-6-chloro-5-methylnicotinic acid (intermediate B1, 500 mg, 2.68 mmol) and formamide (724 mg, 16.1 mmol) was stirred at 140° C. for 18 h in a sealed tube. After cooling to RT, water (30 mL) was added and the mixture was the filtered and the solids were washed with water (2×3 mL). The solids were redissolved in hot water and the solution was allowed to cool to RT and the title compound was collected by filtration. MS: 196 (M+1).

INTERMEDIATE O2

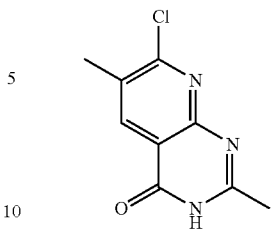

7-Chloro-2,6-dimethylpyrido[2,3-d]pyrimidin-4(3H)-one (Scheme O)

To a solution of 2-amino-6-chloro-5-methylnicotinamide (intermediate B1, 370 mg, 1.993 mmol) in pentan-1-ol (5 mL) was added 1,1,1-triethoxyethane (970 mg, 5.98 mmol). The reaction mixture was stirred at 120° C. for 12 h before the reaction was cooled to RT and diluted with water (50 mL) and extracted with EtOAc (70 mL×3). The combined organic layers were washed with brine (20 mL), dried over anhydrous $Na_2SO_4$, filtered and concentrated. The residue was purified by prep-TLC (50% EtOAc/petroleum ether) to give the title compound. MS: 210 (M+1).

The following intermediates in table O were prepared according to scheme O using the procedure outlined in the synthesis of intermediate O1 and O2 using reaction reagents and temperatures ranging from 80-140° C. as appropriate.

TABLE O

| Intermediate | Structure | Name | MS (M + 1) |
| --- | --- | --- | --- |
| O2[1] | 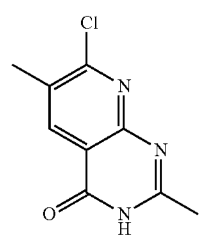 | 7-chloro-2,6-dimethylpyrido[2,3-d]pyrimidin-4(3H)-one | 210 |
| O3[2] | 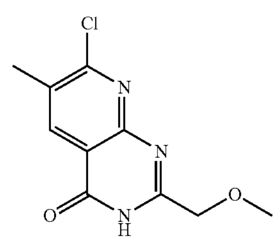 | 7-chloro-2-(methoxymethyl)-6-methylpyrido[2,3-d]pyrimidin-4(3H)-one | 186 |
| O4[3] | 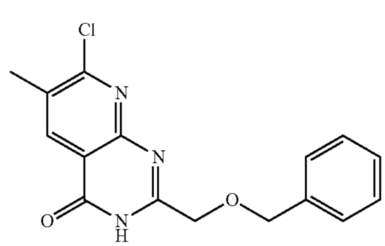 [SMILES: Cc1cc2c(=O)[nH]c(COCc3ccccc3)nc2nc1Cl] | 2-((benzyloxy)methyl)-7-chloro-6-methylpyrido[2,3-d]pyrimidin-4(3H)-one | 316 |

TABLE O-continued

| Intermediate | Structure | Name | MS (M + 1) |
|---|---|---|---|
| O5[2] | 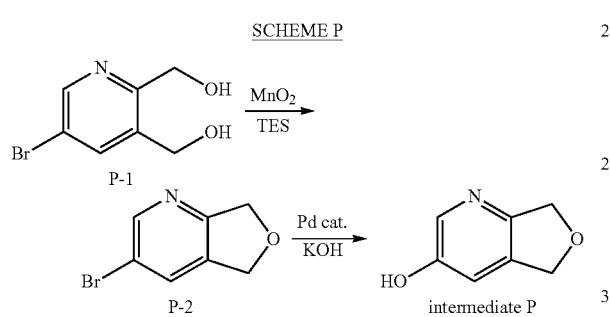 | 7-chloro-2-(2-methoxyethyl)-6-methylpyrido[2,3-d]pyrimidin-4(3H)-one | 254 |

[1]Synthetic protocol used triethyl orthoacetate as the reactive reagent.
[2]Synthetic protocol used 2-methoxyacetyl chloride as the reactive reagent in the presence of solid sodium bicarbonate.
[3]Synthetic protocol used 2-(benzyloxy)acetyl chloride as the reactive reagent in the presence of solid potassium carbonate.
[4]Synthetic protocol used 3-methoxypropanoyl chloride as the reactive reagent in the presence of solid sodium bicarbonate.

SCHEME P

Intermediate P is prepared according to scheme P beginning with commercial diol P-1. A one-pot oxidation, cyclization, and reduction sequence results in the formation of bromide P-2. A palladium-catalyzed hydroxylation reaction provides intermediate P.

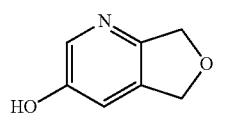

INTERMEDIATE P 5,7-Dihydrofuro[3,4-b]pyridin-3-ol (Scheme P)

Step 1: 3-Bromo-5,7-dihydrofuro[3,4-b]pyridine

TFA (35.3 mL, 459 mmol) was added to a stirred mixture of (5-bromopyridine-2,3-diyl)dimethanol (10 g, 45.9 mmol) in DCM (100 mL) to form a homogeneous solution. Manganese dioxide (18.8 g, 183 mmol) was added to the reaction and the mixture was stirred for 10 min at RT before the addition of triethylsilane (14.7 mL, 92 mmol). After stirring for 4 h at RT, the reaction was filtered and concentrated. The residue was purified by column chromatography on silica gel (10/1 EtOAc/hexane) to yield the title compound.

Step 2: 5,7-Dihydrofuro[3,4-b]pyridin-3-ol

KOH (841 mg, 15.0 mmol) in water (10 mL) was added to a stirred mixture of 3-bromo-5,7-dihydrofuro[3,4-b]pyridine (500 mg, 2.50 mmol), tris(dibenzylideneacetone)dipalladium-chloroform adduct (388 mg, 0.375 mmol) and Brettphos (403 mg, 0.750 mmol) in dioxane (10 mL). The reaction was stirred at 150° C. under microwave irradiation for 30 min. After cooling to RT, the reaction was partitioned and the lower layer was separated and concentrated. The residue was purified by column chromatography on silica gel (20:1 DCM:MeOH) to yield the title compound. $^1$H NMR (500 MHz, CDCl$_3$): δ7.81 (1H, s), 6.94-6.99 (2H, m), 6.88 (1H, d, J=8.3 Hz), 6.24 (1H, s), 4.69 (2H, s), 4.57 (1H, m), 4.37 (2H, s), 3.58 (2H, m), 3.20 (2H, m), 2.37 (3H, s), 2.14 (2H, m), 1.98 (2H, m).

SCHEME Q

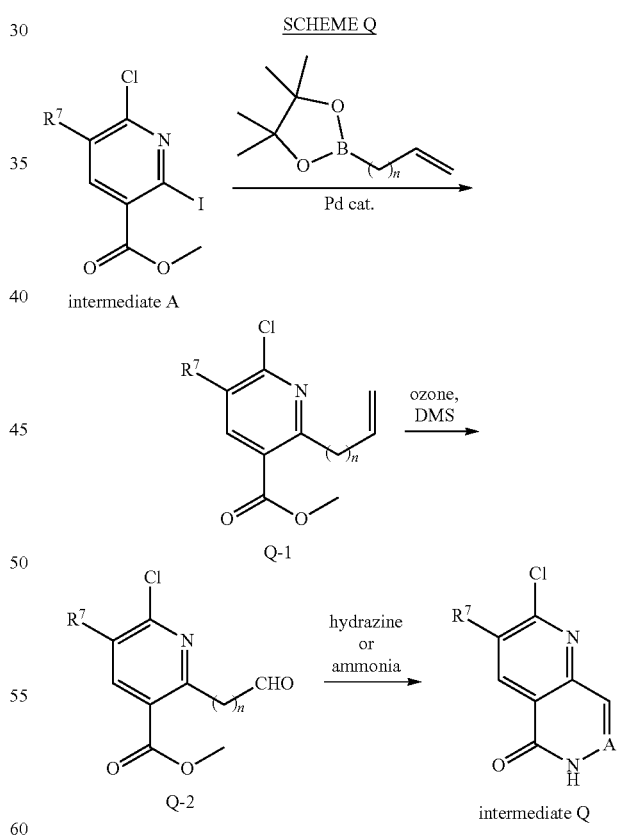

Intermediate Q is prepared from intermediate A which is transformed to adduct Q-1 after a Suzuki couping reaction with vinyl or allylboronic acid pinacol ester (where n=0 or 1). Ozonolysis of the terminal olefin yields the corresponding aldehyde Q-2, which is subsequently condensed with hydrazine or ammonia to afford intermediate Q.

INTERMEDIATE Q1

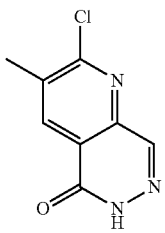

2-Chloro-3-methylpyrido[2,3-d]pyridazin-5(6H)-one
(Scheme Q)

Step 1: Methyl 6-chloro-5-methyl-2-vinylnicotinate

To a solution of methyl 6-chloro-2-iodo-5-methylnicotinate (intermediate A1,1.2 g, 3.85 mmol), 4,4,5,5-tetramethyl-2-vinyl-1,3,2-dioxaborolane (0.593 g, 3.85 mmol) and $K_2CO_3$ (1.331 g, 9.63 mmol) in THF (10 mL) and water (2 mL) was added $PdCl_2(dppf)$ (0.282 g, 0.385 mmol) at 18° C. The reaction was stirred at 40° C. for 16 h under an inert nitrogen atmosphere. The mixture was diluted with water (30 mL) and extracted with EtOAc (30 mL×3). The combined organic phases were washed with brine (20 mL), dried over anhydrous sodium sulfate, filtered, and concentrated in vacuo. The residue was purified by silica gel chromatography (10:1 petroleum ether:EtOAc) to give the title compound.

Step 2: Methyl 6-chloro-2-formyl-5-methylnicotinate

A solution of methyl 6-chloro-5-methyl-2-vinylnicotinate (230 mg, 1.09 mmol) in DCM (10 mL) was bubbled with ozone −78° C. for 3 min and then with nitrogen at RT for 1 h. Dimethyl sulfide (10 mL, 1.09 mmol) was added and the resulting mixture was stirred at RT for 16 h. The mixture was concentrated in vacuo and was directly purified by silica gel chromatography (100:1-5:1 petroleum ether:EtOAc) to afford the title compound.

Step 3: 2-Chloro-3-methylpyrido[2,3-d]pyridazin-5(6H)-one

A solution of methyl 6-chloro-2-formyl-5-methylnicotinate (120 mg, 0.562 mmol) and hydrazine hydrate (0.03 mL, 0.590 mmol) in EtOH (3 mL) was stirred at 17° C. for 1 h. The mixture was diluted with water (20 mL) and extracted with EtOAc (10 mL×3). The combined organic layers were washed with brine (20 mL), dried over anhydrous sodium sulfate, filtered, and concentrated in vacuo. The residue was purified by silica gel chromatography (10:1-1:1 petroleum ether:EtOAc) to the title compound. $^1$H NMR (400 MHz, methanol-$d_4$): δ 8.53 (1H, s), 8.30 (1H, s), 2.59 (3H, s).

INTERMEDIATE Q2

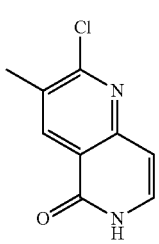

2-Chloro-3-methyl-1,6-naphthyridin-5(6H)-one
(Scheme Q)

Step 1: Methyl 2-allyl-6-chloro-5-methylnicotinate

A mixture of 2-allyl-4,4,5,5-tetramethyl-1,3,2-dioxaborolane (148 mg, 0.883 mmol), methyl 6-chloro-2-iodo-5-methylnicotinate (250 mg, 0.803 mmol) and CsF (366 mg, 2.41 mmol) in THF (10 mL) was placed under an atmosphere of nitrogen. $Pd(Ph_3P)_4$ (93 mg, 0.080 mmol) was added and the mixture was stirred at 70° C. for 16 h under an inert nitrogen atmosphere. The mixture was diluted with EtOAc (30 mL) and water (20 mL) and the organic phase was washed with brine (15 mL), dried over anhydrous sodium sulfate and filtered. The filtrate was concentrated in vacuo and the residue was purified by column chromatography on silica gel (3:1 petroleum ether:ethyl acetate) to afford the title compound.

Step 2: Methyl 6-chloro-5-methyl-2-(2-oxoethyl)nicotinate

A solution of methyl 2-allyl-6-chloro-5-methylnicotinate (100 mg, 0.443 mmol) in DCM (5 mL) and MeOH (0.5 mL) was cooled to −70° C. and bubbled with ozone for 15 min and then with nitrogen for 1 h at RT. Dimethyl sulfide (6.56 μL, 0.089 mmol) was added and the reaction was stirred for 16 h before the volatiles were removed in vacuo and the residue was and directly purified by silica gel chromatography (100:1-5:1 petroleum ether:EtOAc) to afford the title compound.

Step 3: 2-Chloro-3-methyl-1,6-naphthyridin-5(6H)-one

To a mixture of methyl 6-chloro-5-methyl-2-(2-oxoethyl)nicotinate (80 mg, 0.351 mmol) in THF (15 mL) was added ammonia (4 M in THF, 1 mL, 4.0 mmol). The reaction was stirred for 16 h at 15° C. and the volatiles were then removed in vacuo. The residue was dissolved in toluene (15 mL) and the mixture was stirred at 110° C. for 2 h. The cooled mixture was diluted with EtOAc (25 mL) and partitioned with water (25 mL). The organic phase was dried over anhydrous sodium sulfate, filtered and the filtrate was concentrated in vacuo to afford the title compound. MS: 195 (M+1).

The following intermediates in table Q were prepared according to scheme Q using the procedure outlined in the synthesis of intermediate Q1 or Q2.

TABLE Q

| Intermediate | Structure | Name | MS (M + 1) |
| --- | --- | --- | --- |
| Q3 | 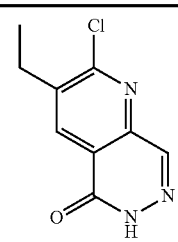 | 2-chloro-3-ethylpyrido[2,3-d]pyridazin-5(6H)-one | 210 |

SCHEME R

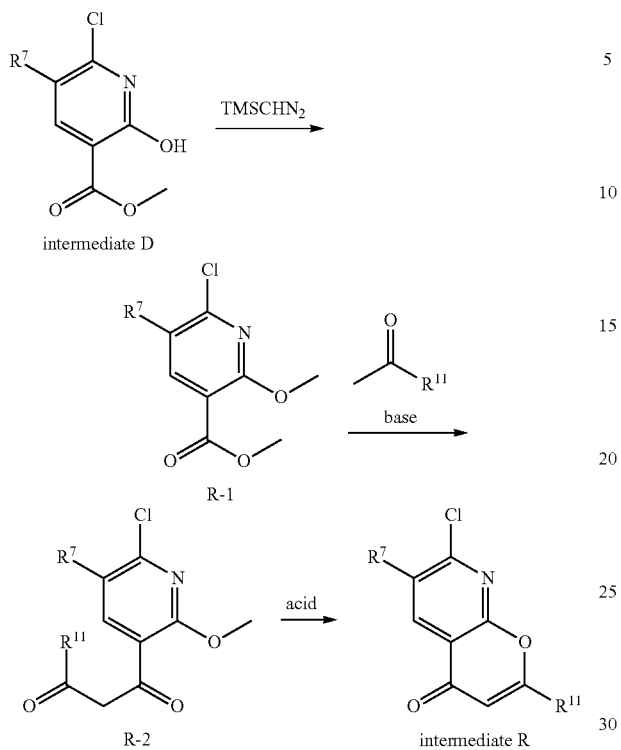

Intermediate R is prepared from intermediate D which is transformed to methyl ether R-1 after treatment with TMS-diazomethane. An aldol reaction with a commercial ketone in the presence of base provides adduct R-2 which under acidic conditions affords intermediate R.

INTERMEDIATE R

7-Chloro-2,6-dimethyl-4H-pyrano[2,3-b]pyridin-4-one (Scheme R)

Step 1: Methyl 6-chloro-2-methoxy-5-methylnicotinate

To a solution of methyl 6-chloro-2-hydroxy-5-methylnicotinate (754 mg, 3.74 mmol) in MeOH (20 mL) was added TMS-diazomethane (2 M, 9.35 mL, 18.7 mmol). The reaction was stirred at RT for 1 h before being dissolved in EtOAc (20 mL), washed with water (20 mL), dried over anhydrous sodium sulfate, filtered and concentrated. The residue was purified by silica gel chromatography (90:10 petroleum ether:EtOAc) to give the title compound.

Step 2: 1-(6-Chloro-2-methoxy-5-methylpyridin-3-yl)butane-1,3-dione

To a solution of propan-2-one (100 mg, 1.72 mmol) and methyl 6-chloro-2-methoxy-5-methylnicotinate (270 mg, 1.25 mmol) in THF (0.5 mL) was added potassium tert-butoxide (1 M, 1.75 mL, 1.75 mmol). The reaction was stirred at RT for 16 h before being diluted with water (20 mL) and EtOAc (20 mL). The organic phase was dried over anhydrous sodium sulfate, filtered and the filtrate was concentrated before purification by prep-TLC (10:1 petroleum ether:EtOAc) to give the title compound.

Step 3: 7-Chloro-2,6-dimethyl-4H-pyrano[2,3-b]pyridin-4-one

A mixture of 1-(6-chloro-2-methoxy-5-methylpyridin-3-yl)butane-1,3-dione (80 mg, 0.331 mmol) and TsOH (63.0 mg, 0.331 mmol) in toluene (1 mL) was stirred at 120° C. for 1 h. The reaction was diluted with water and extracted with EtOAc (15 mL), washed with aqueous $NaHCO_3$ (saturated, 10 mL), dried over anhydrous sodium sulfate, filtrated and concentrated. The residue was purified by prep-TLC (5:1 petroleum ether:EtOAc) to give the title compound. MS: 210 (M+1).

SCHEME 1

Compounds of formula (I) are synthesized from a palladium-mediated C—N coupling reaction of prepared 2-chloro pyridine 1-1 and known or prepared piperidine 1-2.

SCHEME 2

-continued

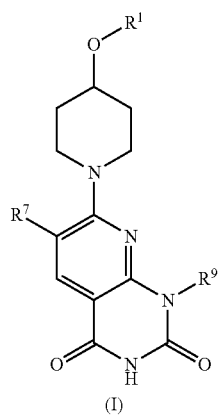

Compounds of formula (I) are synthesized from an $S_NAr$ reaction of prepared intermediate N with an amine to furnish adduct 2-1, which is subsequently reacted with sodium cyanate.

Compounds of formula (I) are synthesized beginning from an $S_NAr$ reaction of a protected amine (PG=protecting group) with prepared intermediate N. Adduct 3-1 is reacted with TFA to provide aniline 3-2. Saponification unveils the acid 3-3 which is coupled with HATU and ammonia or an amine to yield amide 3-4. Acylation and cyclization with triphosgene affords compounds with the formula (I).

SCHEME 4

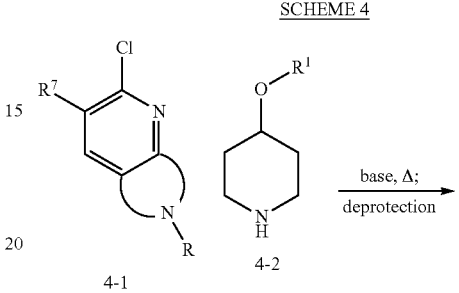

SCHEME 3

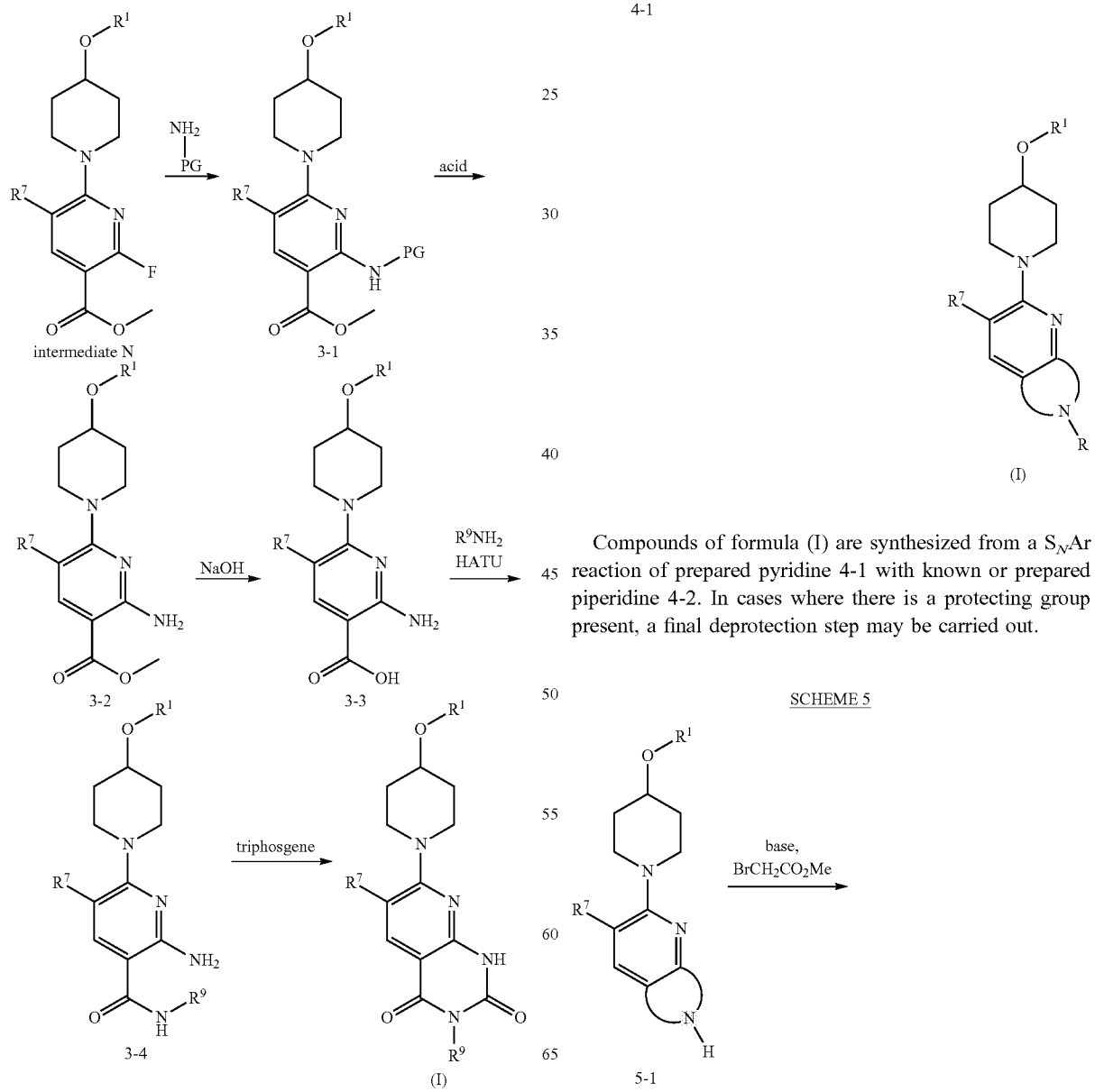

Compounds of formula (I) are synthesized from a $S_NAr$ reaction of prepared pyridine 4-1 with known or prepared piperidine 4-2. In cases where there is a protecting group present, a final deprotection step may be carried out.

SCHEME 5

SCHEME 7

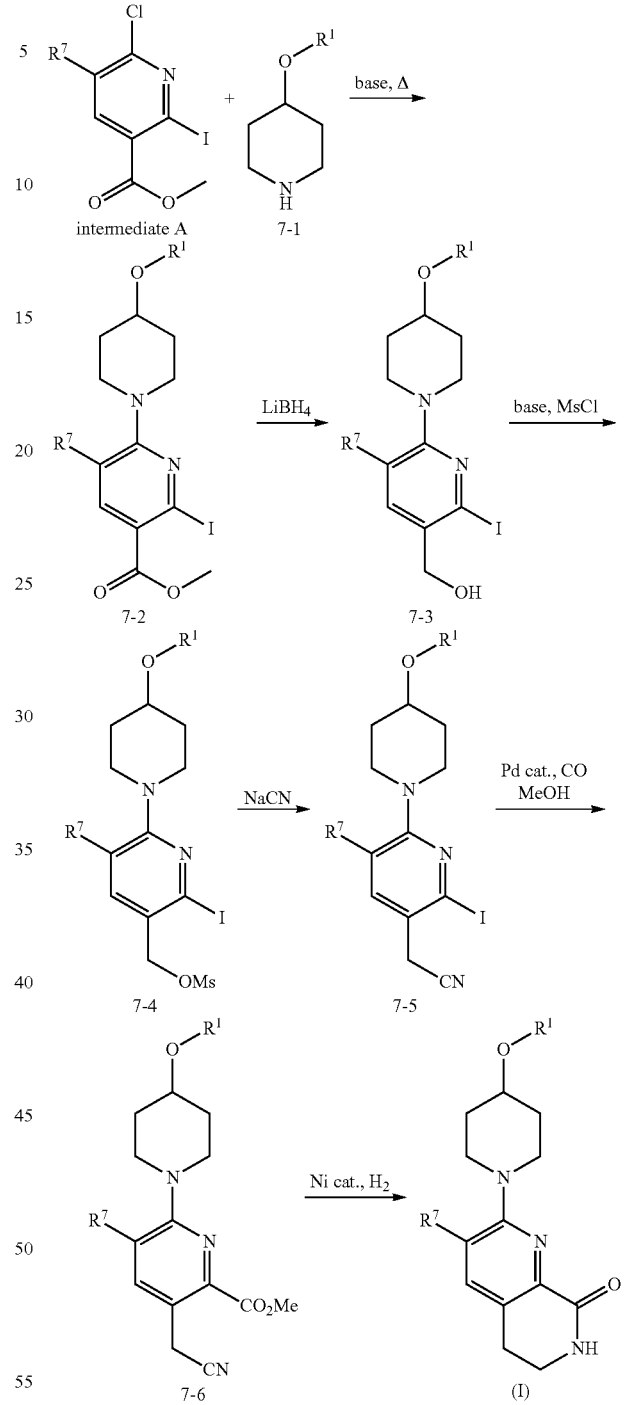

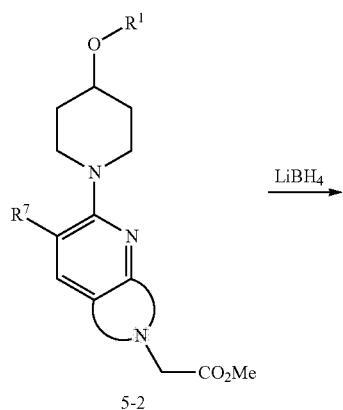

Compounds of formula (I) are synthesized from a prepared amine or amide 5-1, which is transformed to 5-2 via an alkylation with methyl 2-bromoacetate after treatment with base followed by reduction with a hydride source to furnish the corresponding alcohol.

SCHEME 6

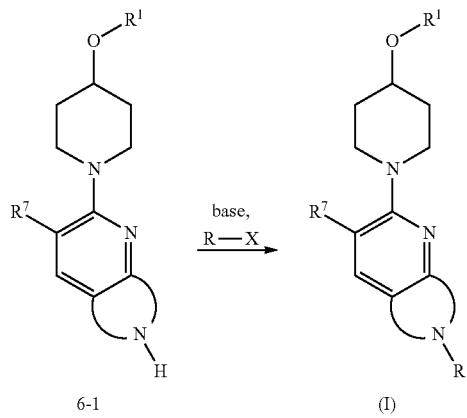

Compounds of formula (I) are synthesized from an amine 5-1 via an alkylation with a commercial alkyl halide after treatment with base.

Compounds of formula (I) are synthesized from an $S_NAr$ of intermediate A and a known or prepared piperdine 7-1. Reduction of ester 7-2 can be carried out with lithium borohydride to yield alcohol 7-3, which is activated to the corresponding mesylate 7-4 for a $S_N2$ displacement reaction with sodium cyanide to furnish nitrile adduct 7-5. A palladium-mediated carbonylation reaction of iodide 7-5 in the presence of methanol provides ester 7-6 which is then subjected to a nickel-catalyzed reduction such that the resulant amine cyclizes to form a lactam in the presence of base.

SCHEME 8

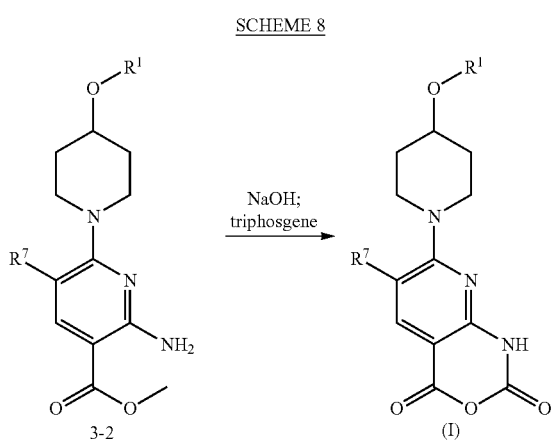

Compounds of formula (I) are synthesized from ester 3-2, prepared according to scheme 3, after serial reaction with first sodium hydroxide and then triphosgene.

SCHEME 9

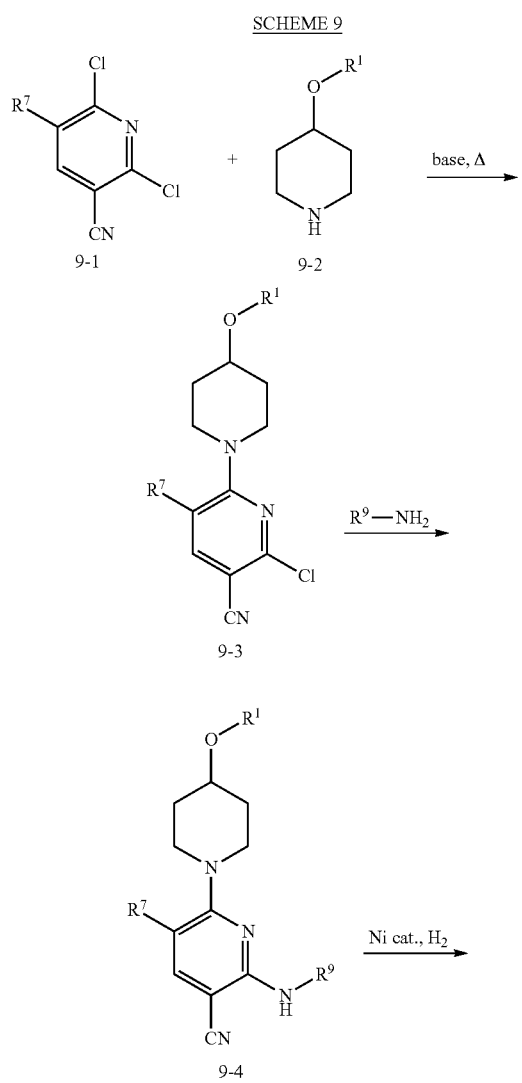

Compounds of formula (I) are synthesized from an $S_NAr$ of known pyridine 9-1 and a known or prepared piperdine 9-2. A second $S_NAr$ reaction of chloride 9-3 with ammonia or an amine provides aniline 9-4. A nickel-catalyzed nitile reduction furnishes amine 9-5, which is subsequently cyclized using CDI or triphosgene to produce compounds of the formula (I).

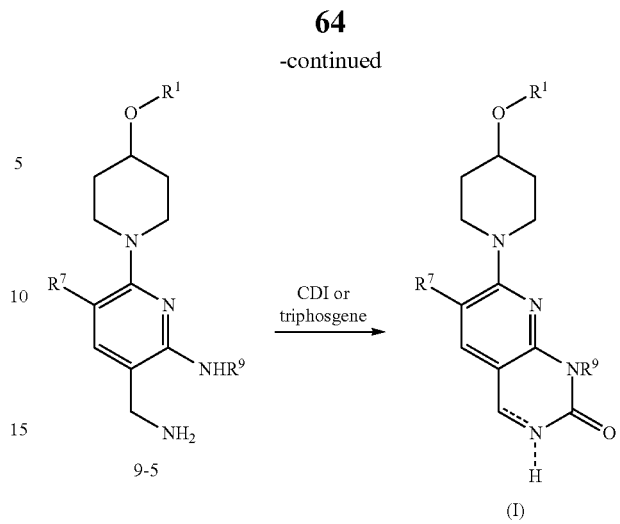

SCHEME 10

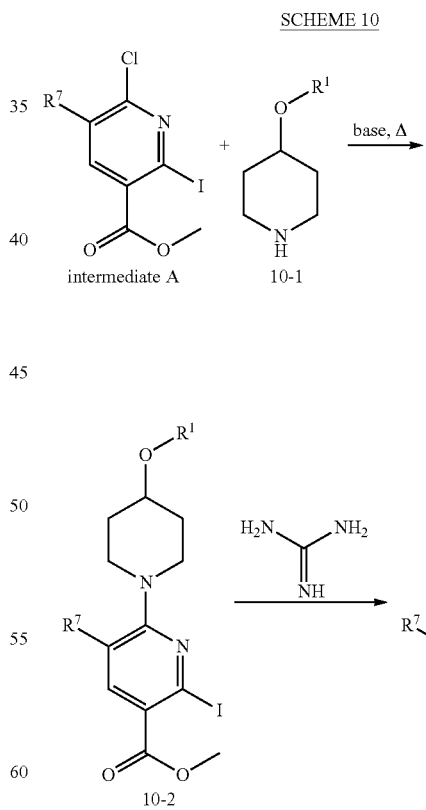

Compounds of formula (I) are synthesized from an $S_NAr$ of intermediate A and a known or prepared piperdine 10-1 followed by condensation with guanidine.

SCHEME 11

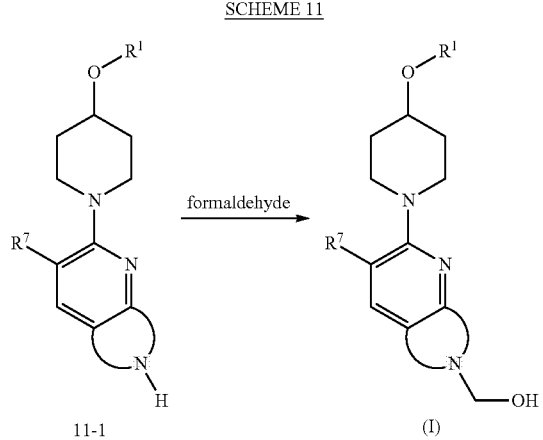

Compounds of formula (I) are synthesized from prepared compound 11-1 via a condensation with formaldehyde.

SCHEME 12

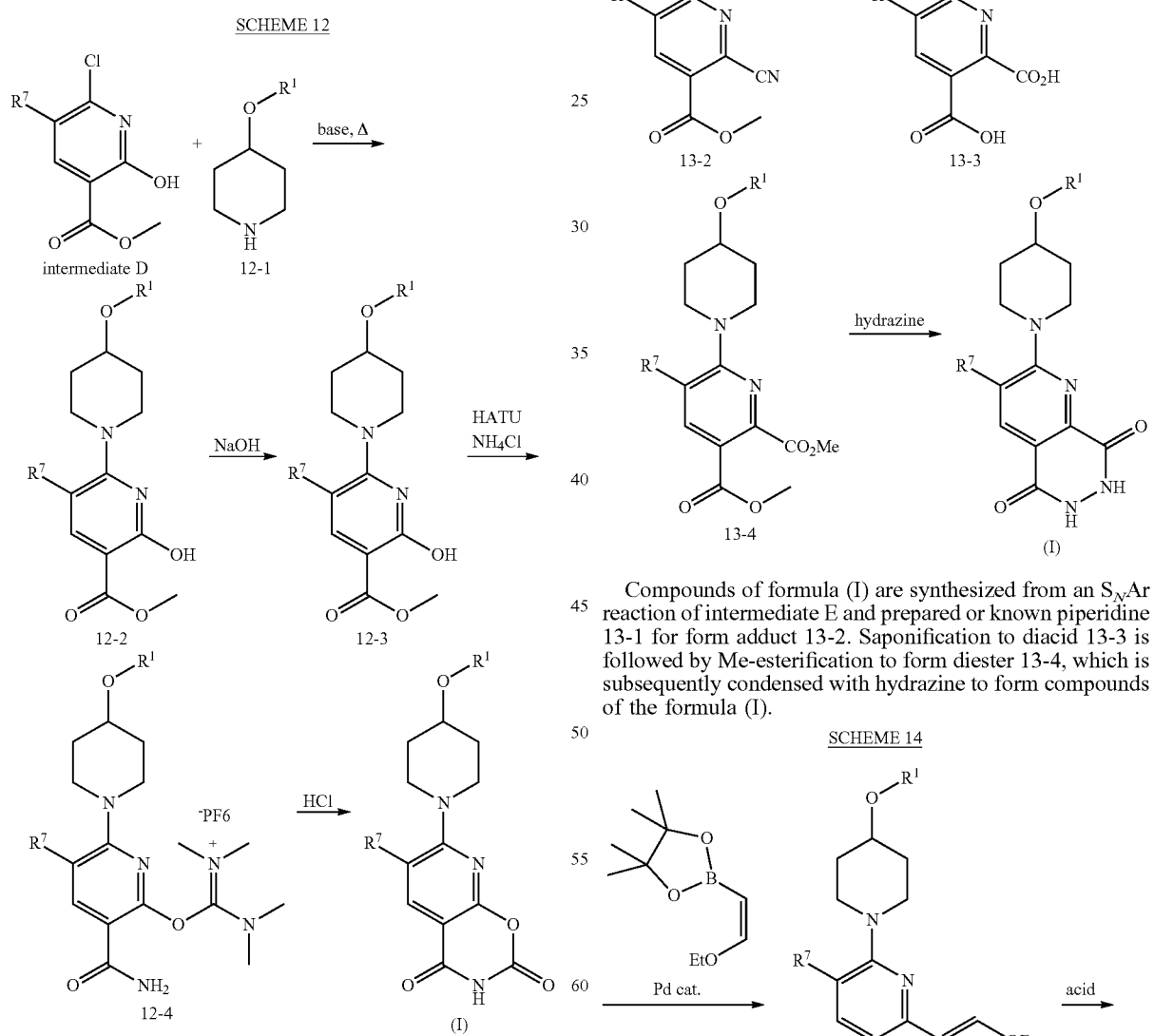

Compounds of formula (I) are synthesized from an $S_NAr$ reaction of intermediate D and prepared or known piperidine 12-1 for form adduct 12-2. Saponification to acid 12-3 is followed by an amide coupling reaction to form carboxamide 12-4 with concomitant isouronium formation. Treatment of carboxamide 12-4 with acid leads to the formation of compounds of the formula (I).

SCHEME 13

Compounds of formula (I) are synthesized from an $S_NAr$ reaction of intermediate E and prepared or known piperidine 13-1 for form adduct 13-2. Saponification to diacid 13-3 is followed by Me-esterification to form diester 13-4, which is subsequently condensed with hydrazine to form compounds of the formula (I).

SCHEME 14

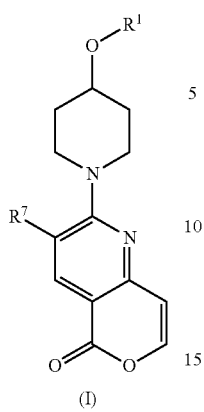

Compounds of formula (I) are synthesized from an S$_N$Ar reaction of intermediate A and prepared or known piperidine 14-1 for form adduct 14-2. A palladium-catalyzed Suzuki reaction of iodide 14-2 with vinyl boronic ester affords enol ether product 14-3, which was subsequently hydrolyzed to form cyclized compounds having the formula (I).

SCHEME 15

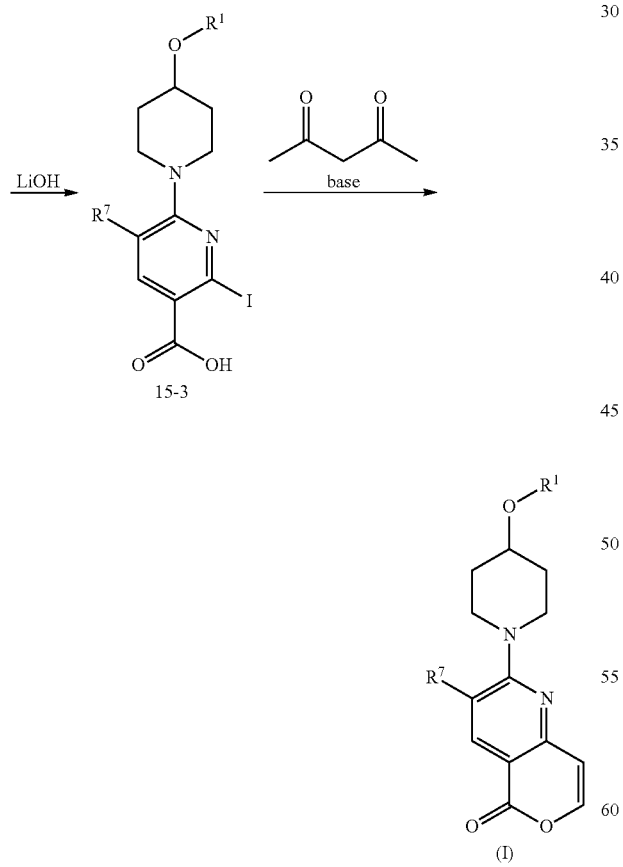

Compounds of formula (I) are synthesized from an S$_N$Ar reaction of intermediate A and a known or prepared piperidine 15-1. Ester 15-2 is saponified and 2-iodobenzoic acid 15-3 is reacted with a β-diketone in the presence of base for an ortho-induced, transition-metal-free C-arylation cyclization reaction.

Example 1

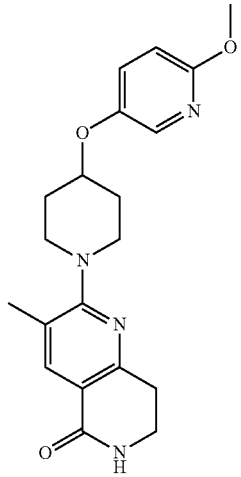

2-(4-((6-Methoxypyridin-3-yl)oxy)piperidin-1-yl)-3-methyl-7,8-dihydro-1,6-naphthyridin-5(6H)-one (Scheme 1)

In a 30 mL schlenk tube, a solution of 2-chloro-3-methyl-7,8-dihydro-1,6-naphthyridin-5(6H)-one (intermediate J, 10 mg, 0.051 mmol) and 2-methoxy-5-(piperidin-4-yloxy)pyridine (intermediate F1, 15.9 mg, 0.076 mmol) in THF (3 mL) was prepared. Sodium 2-methylpropan-2-olate (2 M, 0.102 mL, 0.203 mmol) and (ruphos)palladium(II) phenethylamine chloride (3.71 mg, 5.09 µmol) was added under a nitrogen atmosphere and the mixture was stirred at 50° C. for 3 h. The mixture was concentrated in vacuo and was directly purified by reverse phase HPLC (ACN/water with 0.1% TFA modifier) to afford the title compound. MS: 369 (M+1). $^1$NMR (500 MHz, methanol-d$_4$): δ7.98 (1H, s), 7.84 (1H, d, J=2.8 Hz), 7.46 (1H, dd, J=8.8, 2.8 Hz), 6.79 (1H, d, J=9.2 Hz), 4.48-4.54 (1H, m), 3.86 (3H, s), 3.62-3.70 (2H, m), 3.53 (2H, t, J=6.8 Hz), 3.24-3.30 (2H, m), 3.03 (2H, t, J=6.8 Hz), 2.34 (3H, s), 2.08-2.17 (2H, m), 1.80-1.91 (2H, m).

The following examples in table 1 were prepared according to scheme 1 using the procedure outlined in the synthesis of Example 1 using prepared piperidines and 2-chloropyridines.

TABLE 1

| Example | Structure | Name | MS (M + 1) |
|---|---|---|---|
| 2 | 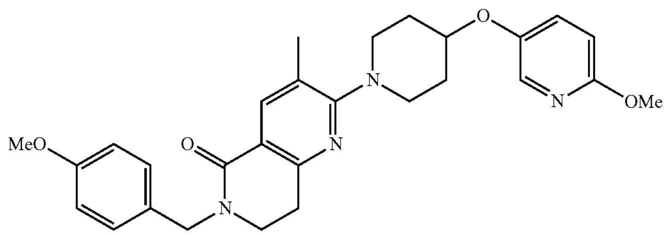 [SMILES: COc1ccc(CN2CCc3nc(N4CCC(Oc5ccc(OC)nc5)CC4)c(C)cc3C2=O)cc1] | 6-(4-methoxybenzyl)-2-(4-((6-methoxypyridin-3-yl)oxy)piperidin-1-yl)-3-methyl-7,8-dihydro-1,6-naphthyridin-5(6H)-one | 489 |
| 3 | 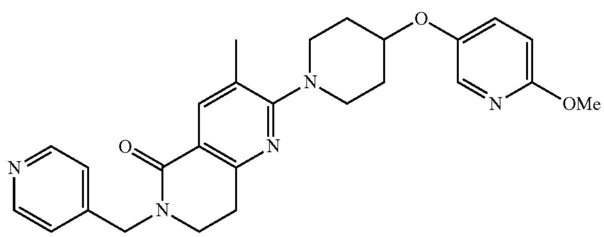 [SMILES: COc1ccc(OC2CCN(c3nc4c(cc3C)C(=O)N(Cc3ccncc3)CC4)CC2)cn1] | 2-(4-((6-methoxypyridin-3-yl)oxy)piperidin-1-yl)-3-methyl-6-(pyridin-4-ylmethyl)-7,8-dihydro-1,6-naphthyridin-5(6H)-one | 460 |
| 4 | 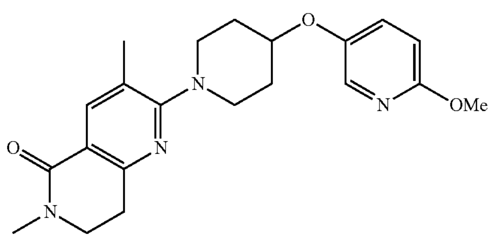 [SMILES: COc1ccc(OC2CCN(c3nc4c(cc3C)C(=O)N(C)CC4)CC2)cn1] | 2-(4-((6-methoxypyridin-3-yl)oxy)piperidin-1-yl)-3,6-dimethyl-7,8-dihydro-1,6-naphthyridin-5(6H)-one | 383 |

Example 5

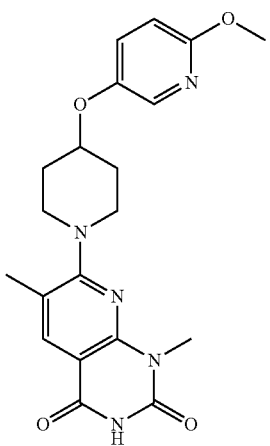

7-(4-((6-Methoxypyridin-3-yl)oxy)piperidin-1-yl)-1,6-dimethylpyrido[2,3-d]pyrimidine-2,4(1H,3H)-dione (Scheme 2)

Step 1: Methyl 6-(4-((6-methoxypyridin-3-yl)oxy)piperidin-1-yl)-5-methyl-2-(methylamino)nicotinate A solution of methyl 2-fluoro-6-(4-((6-methoxypyridin-3-yl)oxy)piperidin-1-yl)-5-methylnicotinate (300 mg, 0.799 mmol) and methanamine(2 M in THF, 20 mL, 40 mmol) was stirred at 120° C. in a sealed tube for 12 h. The reaction was cooled and the volatiles were removed under reduced pressure. The crude product was purified by silica gel chromatography (0-30% EtOAc/petroleum ether) to give the title compound. MS: 387 (M+1).

Step 2: 7-(4-((6-Methoxypyridin-3-yl)oxy)piperidin-1-yl)-1,6-dimethylpyrido[2,3-d]pyrimidine-2,4(1H,3H)-dione To a solution of methyl 6-(4-((6-methoxypyridin-3-yl)oxy)piperidin-1-yl)-5-methyl-2-(methylamino)nicotinate (270 mg, 0.699 mmol) in AcOH (5 mL) was added sodium cyanate (182 mg, 2.79 mmol). The reaction mixture was stirred at 110° C. for 3 days. The solvent was evaporated under reduced pressure and the resultant residue was purified by reverse phase HPLC (ACN/water with 0.1% TFA modifier) to yield the title compound. MS: 398 (M+1). $^1$H NMR (400 MHz, CDCl$_3$): δ7.97-8.00 (2H, m), 7.89 (1H, d, J=2.8 Hz), 6.73 (1H, dd, J=8.8 Hz 3.2 Hz), 4.42-4.47 (1H, m), 3.92 (3H, s), 3.72-3.83 (2H, m), 3.60 (3H, s), 3.37-3.41 (2H, m), 2.32 (3H, s), 2.09-2.13 (2H, m), 1.94-1.98 (2H, m).

Example 6

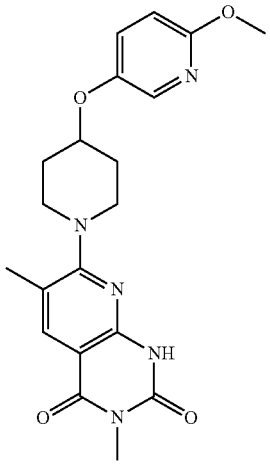

7-(4-((6-Methoxypyridin-3-yl)oxy)piperidin-1-yl)-3,6-dimethylpyrido[2,3-d]pyrimidine-2,4(1H,3H)-dione (Scheme 3)

Step 1: Methyl 2-((2,4-dimethoxybenzyl)amino)-6-(4-((6-methoxypyridin-3-yl)oxy)piperidin-1-yl)-5-methylnicotinate To a solution of methyl 2-fluoro-6-(4-((6-methoxypyridin-3-yl)oxy)piperidin-1-yl)-5-methylnicotinate (intermediate N1, 70 mg, 0.186 mmol) in acetonitrile (2 mL) was added $K_2CO_3$ (77 mg, 0.559 mmol) and (2,4-dimethoxyphenyl)methanamine (62.4 mg, 0.373 mmol). The reaction was stirred at 80° C. for 18 h, then it was diluted with water (10 mL) and extracted with EtOAc (20 mL×3). The combined organic layers was dried over anhydrous sodium sulfate, filtered and the filtrate was concentrated. The residue was purified by prep-TLC (2:1 petroleum ether:EtOAc) to afford the title compound. MS: 523 (M+1).

Step 2: Methyl 2-amino-6-(4-((6-methoxypyridin-3-yl)oxy)piperidin-1-yl)-5-methylnicotinate To a solution of methyl 2-((2,4-dimethoxybenzyl)amino)-6-(4-((6-methoxypyridin-3-yl)oxy)piperidin-1-yl)-5-methylnicotinate (100 mg, 0.191 mmol) in DCM (1 mL) was added TFA (1 mL) and the mixture was stirred at 30° C. for 18 h. The reaction was diluted with water (10 mL) and extracted with EtOAc (20 mL×3). The combined organic layers were dried over over anhydrous $Na_2SO_4$, filtered and the filtrate was concentrated. The residue was purified by prep-TLC (2:1 petroleum ether:EtOAc) to afford the title compound. MS: 373 (M+1).

Step 3: 2-Amino-6-(4-((6-methoxypyridin-3-yl)oxy)piperidin-1-yl)-5-methylnicotinic acid To a solution of methyl 2-amino-6-(4-((6-methoxypyridin-3-yl)oxy)piperidin-1-yl)-5-methylnicotinate (40 mg, 0.107 mmol) in MeOH (3 mL) and water (1 mL) was added NaOH (6.44 mg, 0.161 mmol). The reaction was stirred at 35° C. for 18 h and then it was acidified with aqueous HCl (1 M) to pH~6. The mixture was extracted with EtOAc (10 mL×3), the combined organic phases were dried over anhydrous $Na_2SO_4$, filtered and the filtrate was concentrated to give the title compound. MS: 359 (M+1).

Step 4: 2-Amino-6-(4-((6-methoxypyridin-3-yl)oxy)piperidin-1-yl)-N,5-dimethylnicotinamide To a solution of 2-amino-6-(4-((6-methoxypyridin-3-yl)oxy)piperidin-1-yl)-5-methylnicotinic acid (35 mg, 0.098 mmol) in DCM (3 mL) was added HATU (55.7 mg, 0.146 mmol) and triethylamine (49.4 mg, 0.488 mmol). The mixture was stirred at 20° C. for 18 h before it was concentrated under reduced pressure. The residue was purified by prep-TLC (1:1 petroleum ether:EtOAc) to give the title compound. MS: 372 (M+1).

Step 5: 7-(4(((6-Methoxypyridin-3-yl)oxy)piperidin-1-yl)-1,6-dimethylpyrido[2,3-d]pyrimidine-2,4(1H,3H)-dione To a solution of 2-amino-6-(4-((6-methoxypyridin-3-yl)oxy)piperidin-1-yl)-N,5-dimethylnicotinamide (20 mg, 0.054 mmol) in dioxane (1 mL) was added bis(trichloromethyl) carbonate (16.0 mg, 0.054 mmol). The reaction was stirred at 100° C. for 2 h. The volatiles were removed under reduced pressure and and the resultant residue was purified by reverse phase HPLC (ACN/water with 0.1% TFA modifier) to yield the title compound. MS: 398 (M+1) $^1$H NMR (400 MHz, $CDCl_3$): δ8.22 (1H, br s), 7.95-7.97 (2H, m), 7.36 (1H, dd, J=8.8, 2.4 Hz), 6.78 (1H, d, J=8.8 Hz), 4.44-4.46 (1H, m), 3.94 (3H, s), 3.63-3.68 (2H, m), 3.40 (3H, s), 3.27-3.32 (2H, m), 2.29 (3H, s), 2.04-2.08 (2H, m), 1.90-1.94 (2H, m).

The following examples in table 3 were prepared according to scheme 3 using the procedure outlined in the synthesis of Example 6 using commercially available amines or ammonium chloride in step 4.

TABLE 3

| Example | Structure | Name | MS (M + 1) |
|---|---|---|---|
| 7 | 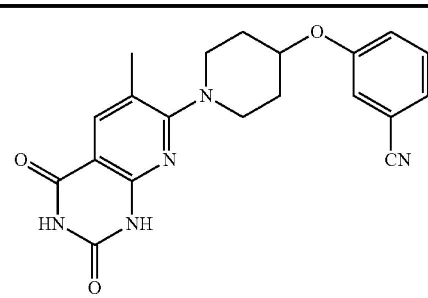 | 3-((1-(6-methyl-2,4-dioxo-1,2,3,4-tetrahydropyrido[2,3-d]pyrimidin-7-yl)piperidin-4-yl)oxy)benzonitrile | 378 |

Example 8

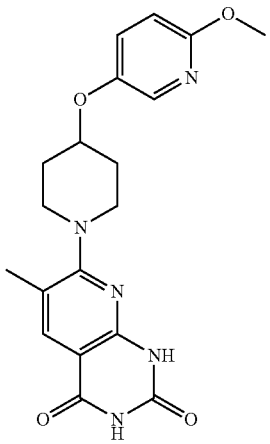

7-(4-((6-Methoxypyridin-3-yl)oxy)piperidin-1-yl)-6-methylpyrido[2,3-d]pyrimidine-2,4(1H,3H)-dione (Scheme 4)

To a solution of 2-methoxy-5-(piperidin-4-yloxy)pyridine, 2HCl (1.06 g, 3.78 mmol) and 7-chloro-6-methylpyrido[2,3-d]pyrimidine-2,4(1H,3H)-dione (intermediate H1, 0.8 g, 3.78 mmol) in DMF (15 mL) was added DIPEA (3.30 mL, 18.9 mmol). The reaction was stirred at 80° C. for 15 h before the mixture was cooled to RT and was diluted with water (10 mL) and was extracted with DCM (20 mL×3). The combined organic fractions were washed with water (20 mL×3), dried over anhydrous sodium sulfate, filtered and concentrated. The residue was purified by reverse phase HPLC (ACN/water with 0.1% TFA modifier) to yield the title compound. MS: 384 (M+1) $^1$H NMR (400 MHz, methanol-$d_4$): δ7.82-7.90 (2H, m), 7.52 (1H, dd, J=9.2, 3.2 Hz), 6.85 (1H, d, J=8.8 Hz), 4.50-4.55 (1H, m), 3.89 (3H, s), 3.69-3.76 (2H, m), 3.31-3.37 (2H, m), 2.32 (3H, s), 2.08-2.15 (2H, m), 1.80-1.90 (2H, m).

Example 9

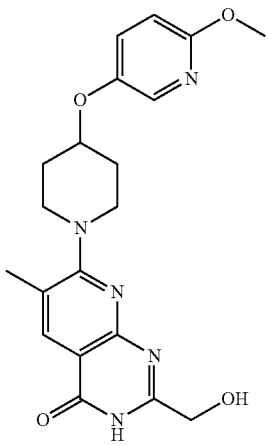

2-(Hydroxymethyl)-7-(4-((6-methoxypyridin-3-yl)oxy)piperidin-1-yl)-6-methylpyrido[2,3-d]pyrimidin-4(3H)-one (Scheme 4)

Step 1: 2-((Benzyloxy)methyl)-7-(4-((6-methoxypyridin-3-yl)oxy)piperidin-1-yl)-6-methylpyrido[2,3-d]pyrimidin-4(3H)-one To a solution of 2-((benzyloxy)methyl)-7-chloro-6-methylpyrido[2,3-d]pyrimidin-4(3H)-one (intermediate O4, 180 mg, 0.570 mmol) in NMP (3 mL) was added 2-methoxy-5-(piperidin-4-yloxy)pyridine hydrochloride (200 mg, 0.817 mmol) and tributylamine (820 mg, 4.42 mmol). The reaction was stirred 1 h at 180° C. under microwave irradiation. The mixture was diluted with water and extracted with DCM (20 mL×3). The combined organic layers were washed with brine (10 mL), dried over anhydrous sodium sulfate, filtered and concentrated. The residue was purified by silica gel chromatography (20-50% THF/petroleum ether) to furnish the title compound. MS: 488 (M+1).

Step 2: 2-(Hydroxymethyl)-7-(4-((6-methoxypyridin-3-yl)oxy)piperidin-1-yl)-6-methylpyrido[2,3-d]pyrimidin-4(3H)-one To a solution of 2-((benzyloxy)methyl)-7-(4-((6-methoxypyridin-3-yl)oxy)piperidin-1-yl)-6-methylpyrido[2,3-d]pyrimidin-4(3H)-one (200 mg, 0.41 mmol) in MeOH (10 mL) was added Pd/C (10 wt %, 50 mg, 0.47 mmol). The mixture was stirred 16 h at 15° C. under a hydrogen atmosphere (15 psi). The mixture was filtered and the filtrate was concentrated and the resultant residue was purified by reverse phase HPLC (ACN/water with 0.1% ammonium carbonate modifier) to yield the title compound. MS: 398 (M+1). $^1$H NMR (400 MHz, DMSO-$d_6$): δ11.80 (1H, br s), 8.00 (1H, s), 7.89 (1H, d, J=2.8 Hz), 7.44 (1H, dd, J=8.8, 3.2 Hz), 6.74 (1H, d, J=8.8 Hz), 5.59 (1H, t, J=6.0 Hz), 4.48-4.52 (1H, m), 4.33 (2H, d, J=6.0 Hz), 3.78 (3H, s), 3.52-3.64 (2H, m), 3.12-3.18 (2H, m), 2.31 (3H, s), 1.95-2.05 (2H, m), 1.66-1.75 (2H, m).

The following examples in table 4 were prepared according to scheme 4 using the procedure outlined in the synthesis of Examples 8 and 9 using prepared piperidines and 2-chloropyridines.

TABLE 4

| Example | Structure | Name | MS (M + 1) |
|---|---|---|---|
| 10 | 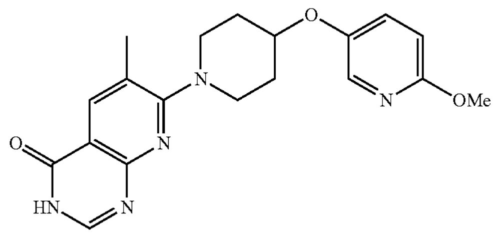 [SMILES: COc1ccc(OC2CCN(c3nc4nc[nH]c(=O)c4cc3C)CC2)cn1] | 7-(4-((6-methoxypyridin-3-yl)oxy)piperidin-1-yl)-6-methylpyrido[2,3-d]pyrimidin-4(3H)-one | 368 |
| 11 | 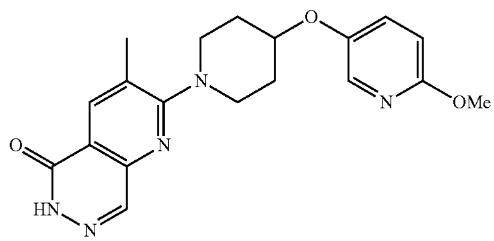 [SMILES: COc1ccc(OC2CCN(c3nc4cn[nH]c(=O)c4cc3C)CC2)cn1] | 2-(4-((6-methoxypyridin-3-yl)oxy)piperidin-1-yl)-3-methylpyrido[2,3-d]pyridazin-5(6H)-one | 368 |
| 12 | 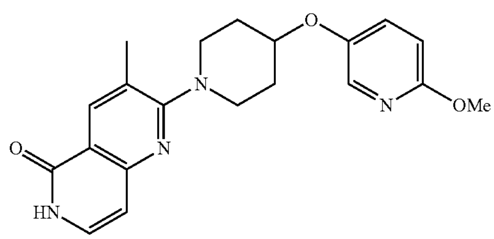 [SMILES: COc1ccc(OC2CCN(c3nc4cc[nH]c(=O)c4cc3C)CC2)cn1] | 2-(4-((6-methoxypyridin-3-yl)oxy)piperidin-1-yl)-3-methyl-1,6-naphthyridin-5(6H)-one | 367 |
| 13 | 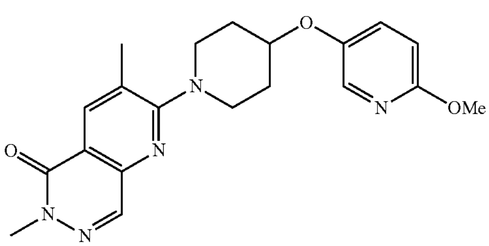 [SMILES: COc1ccc(OC2CCN(c3nc4cnn(C)c(=O)c4cc3C)CC2)cn1] | 2-(4-((6-methoxypyridin-3-yl)oxy)piperidin-1-yl)-3,6-dimethylpyrido[2,3-d]pyridazin-5(6H)-one | 382 |
| 14 | 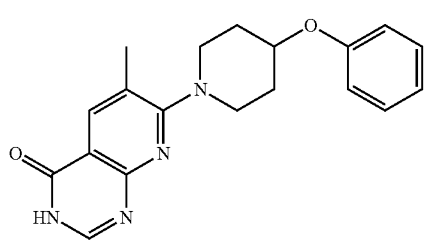 [SMILES: Cc1cc2c(=O)[nH]cnc2nc1N1CCC(Oc2ccccc2)CC1] | 6-methyl-7-(4-phenoxypiperidin-1-yl)pyrido[2,3-d]pyrimidin-4(3H)-one | 337 |
| 15 | 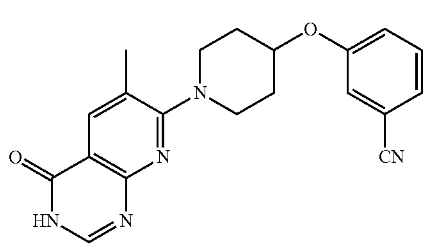 [SMILES: Cc1cc2c(=O)[nH]cnc2nc1N1CCC(Oc2cccc(C#N)c2)CC1] | 3-((1-(6-methyl-4-oxo-3,4-dihydropyrido[2,3-d]pyrimidin-7-yl)piperidin-4-yl)oxy)benzonitrile | 362 |

TABLE 4-continued

| Example | Structure | Name | MS (M + 1) |
| --- | --- | --- | --- |
| 16 | 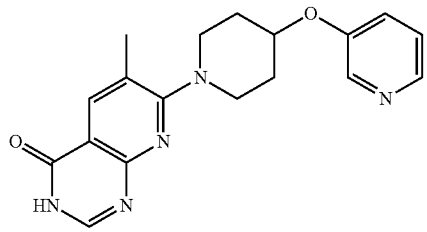 [SMILES: Cc1cc2c(=O)[nH]cnc2nc1N1CCC(Oc2cccnc2)CC1] | 6-methyl-7-(4-(pyridin-3-yloxy)piperidin-1-yl)pyrido[2,3-d]pyrimidin-4(3H)-one | 338 |
| 17 | 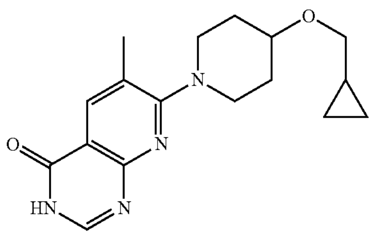 [SMILES: Cc1cc2c(=O)[nH]cnc2nc1N1CCC(OCC2CC2)CC1] | 7-(4-(cyclopropylmethoxy)piperidin-1-yl)-6-methylpyrido[2,3-d]pyrimidin-4(3H)-one | 315 |
| 18 | 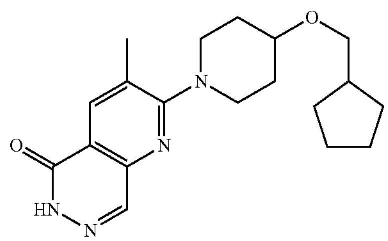 [SMILES: Cc1cc2c(=O)[nH]ncc2nc1N1CCC(OCC2CCCC2)CC1] | 2-(4-(cyclopentylmethoxy)piperidin-1-yl)-3-methylpyrido[2,3-d]pyridazin-5(6H)-one | 343 |
| 19 | 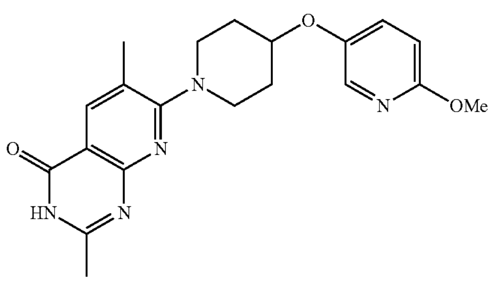 [SMILES: COc1ccc(OC2CCN(c3nc4nc(C)[nH]c(=O)c4cc3C)CC2)cn1] | 7-(4-((6-methoxypyridin-3-yl)oxy)piperidin-1-yl)-2,6-dimethylpyrido[2,3-d]pyrimidin-4(3H)-one | 382 |
| 20 | 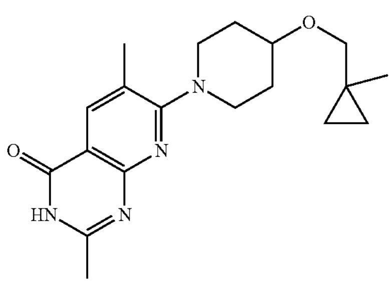 [SMILES: Cc1nc2nc(N3CCC(OCC4(C)CC4)CC3)c(C)cc2c(=O)[nH]1] | 2,6-dimethyl-7-(4-((1-methylcyclopropyl)methoxy)piperidin-1-yl)pyrido[2,3-d]pyrimidin-4(3H)-one | 343 |
| 21 | 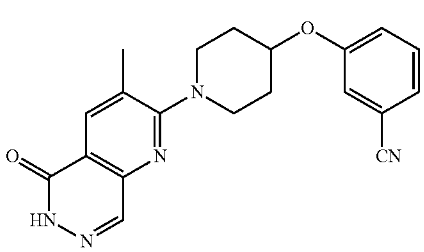 [SMILES: Cc1cc2c(=O)[nH]ncc2nc1N1CCC(Oc2cccc(C#N)c2)CC1] | 3-((1-(3-methyl-5-oxo-5,6-dihydropyrido[2,3-d]pyridazin-2-yl)piperidin-4-yl)oxy)benzonitrile | 362 |

TABLE 4-continued

| Example | Structure | Name | MS (M + 1) |
|---|---|---|---|
| 22 | 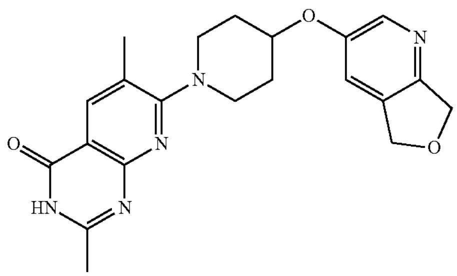 [SMILES: Cc1nc2nc(N3CCC(Oc4cnc5c(c4)COC5)CC3)c(C)cc2c(=O)[nH]1] | 7-(4-((5,7-dihydrofuro[3,4-b]pyridin-3-yl)oxy)piperidin-1-yl)-2,6-dimethylpyrido[2,3-d]pyrimidin-4(3H)-one | 394 |
| 23 | 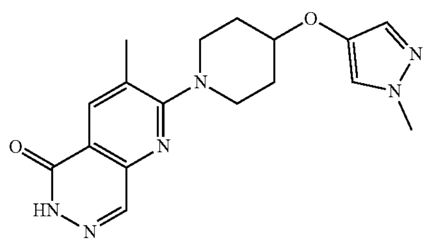 [SMILES: Cc1cc2c(=O)[nH]ncc2nc1N1CCC(Oc2cnn(C)c2)CC1] | 3-methyl-2-(4-((1-methyl-1H-pyrazol-4-yl)oxy)piperidin-1-yl)pyrido[2,3-d]pyridazin-5(6H)-one | 341 |
| 24 | 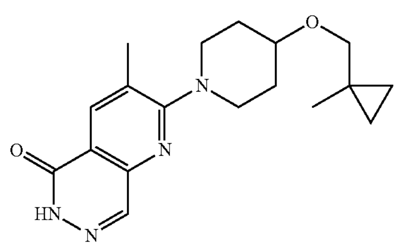 [SMILES: Cc1cc2c(=O)[nH]ncc2nc1N1CCC(OCC2(C)CC2)CC1] | 3-methyl-2-(4-((1-methylcyclopropyl)methoxy)piperidin-1-yl)pyrido[2,3-d]pyridazin-5(6H)-one | 329 |
| 25 | 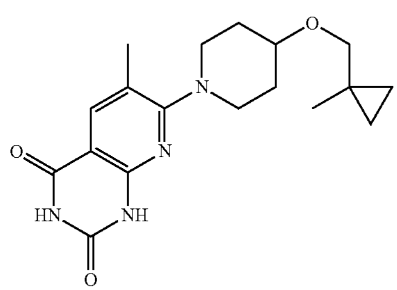 [SMILES: Cc1cc2c(=O)[nH]c(=O)[nH]c2nc1N1CCC(OCC2(C)CC2)CC1] | 6-methyl-7-(4-((1-methylcyclopropyl)methoxy)piperidin-1-yl)pyrido[2,3-d]pyrimidine-2,4(1H,3H)-dione | 345 |
| 26 | 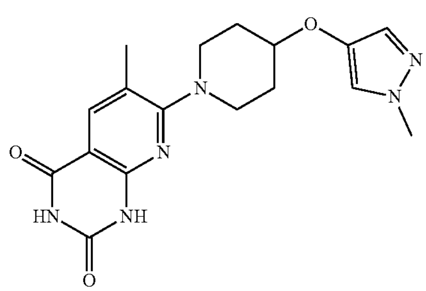 [SMILES: Cc1cc2c(=O)[nH]c(=O)[nH]c2nc1N1CCC(Oc2cnn(C)c2)CC1] | 6-methyl-7-(4-((1-methyl-1H-pyrazol-4-yl)oxy)piperidin-1-yl)pyrido[2,3-d]pyrimidine-2,4(1H,3H)-dione | 357 |
| 27 | 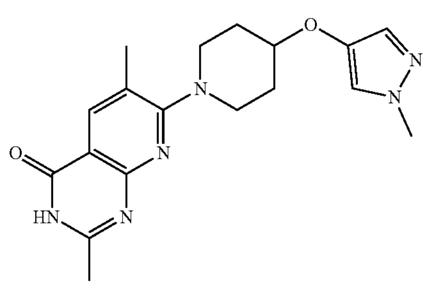 [SMILES: Cc1nc2nc(N3CCC(Oc4cnn(C)c4)CC3)c(C)cc2c(=O)[nH]1] | 2,6-dimethyl-7-(4-((1-methyl-1H-pyrazol-4-yl)oxy)piperidin-1-yl)pyrido[2,3-d]pyrimidin-4(3H)-one | 355 |

TABLE 4-continued

| Example | Structure | Name | MS (M + 1) |
|---|---|---|---|
| 28 | 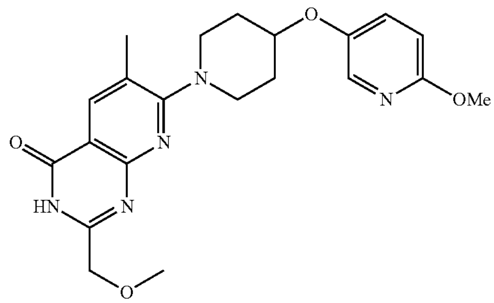 [SMILES: COCc1nc2nc(N3CCC(Oc4ccc(OC)nc4)CC3)c(C)cc2c(=O)[nH]1] | 2-(methoxymethyl)-7-(4-((6-methoxypyridin-3-yl)oxy)piperidin-1-yl)-6-methylpyrido[2,3-d]pyrimidin-4(3H)-one | 412 |
| 29 | 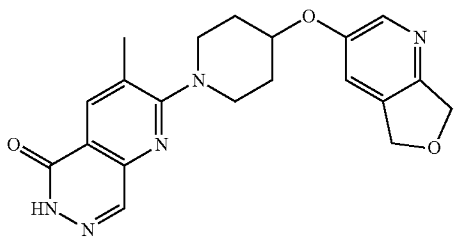 [SMILES: Cc1cc2c(=O)[nH]ncc2nc1N1CCC(Oc2cnc3c(c2)COC3)CC1] | 2-(4-((5,7-dihydrofuro[3,4-b]pyridin-3-yl)oxy)piperidin-1-yl)-3-methylpyrido[2,3-d]pyridazin-5(6H)-one | 380 |
| 30 | 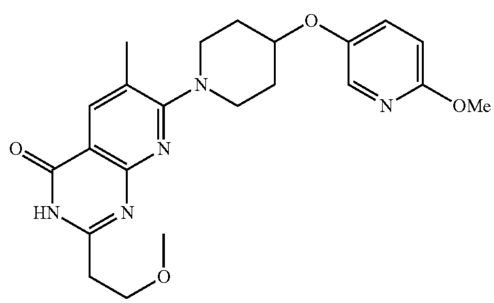 [SMILES: COCCc1nc2nc(N3CCC(Oc4ccc(OC)nc4)CC3)c(C)cc2c(=O)[nH]1] | 2-(2-methoxyethyl)-7-(4-((6-methoxypyridin-3-yl)oxy)piperidin-1-yl)-6-methylpyrido[2,3-d]pyrimidin-4(3H)-one | 426 |
| 31 | 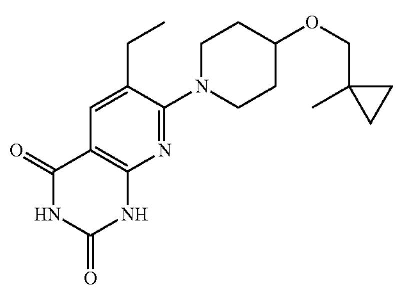 [SMILES: CCc1cc2c(=O)[nH]c(=O)[nH]c2nc1N1CCC(OCC2(C)CC2)CC1] | 6-ethyl-7-(4-((1-methylcyclopropyl)methoxy)piperidin-1-yl)pyrido[2,3-d]pyrimidine-2,4(1H,3H)-dione | 359 |
| 32 | 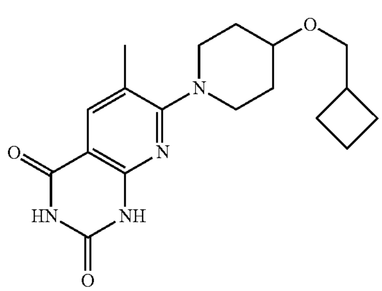 [SMILES: Cc1cc2c(=O)[nH]c(=O)[nH]c2nc1N1CCC(OCC2CCC2)CC1] | 7-(4-(cyclobutylmethoxy)piperidin-1-yl)-6-methylpyrido[2,3-d]pyrimidine-2,4(1H,3H)-dione | 345 |

TABLE 4-continued

| Example | Structure | Name | MS (M + 1) |
|---|---|---|---|
| 33 | 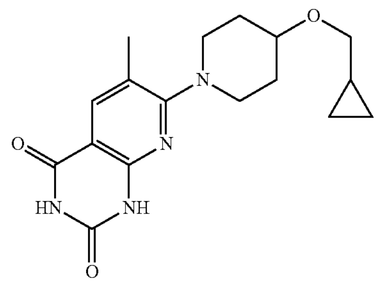 [SMILES: Cc1cc2c(=O)[nH]c(=O)[nH]c2nc1N1CCC(OCC2CC2)CC1] | 7-(4-(cyclopropyl-methoxy)piperidin-1-yl)-6-methylpyrido[2,3-d]pyrimidine-2,4(1H,3H)-dione | 331 |
| 34 | 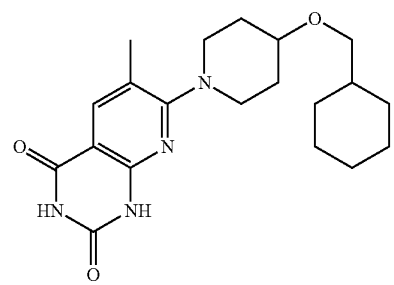 [SMILES: Cc1cc2c(=O)[nH]c(=O)[nH]c2nc1N1CCC(OCC2CCCCC2)CC1] | 7-(4-(cyclohexyl-methoxy)piperidin-1-yl)-6-methylpyrido[2,3-d]pyrimidine-2,4(1H,3H)-dione | 373 |
| 35 | 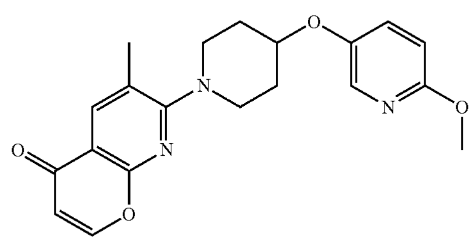 [SMILES: COc1ccc(OC2CCN(c3nc4occc(=O)c4cc3C)CC2)cn1] | 7-(4-((6-methoxypyridin-3-yl)oxy)piperidin-1-yl)-6-methyl-4H-pyrano[2,3-b]pyridin-4-one | 368 |
| 36 | 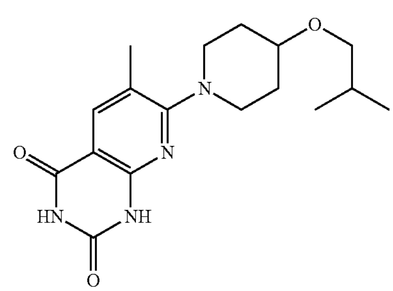 [SMILES: Cc1cc2c(=O)[nH]c(=O)[nH]c2nc1N1CCC(OCC(C)C)CC1] | 7-(4-isobutoxy-piperidin-1-yl)-6-methylpyrido[2,3-d]pyrimidine-2,4(1H,3H)-dione | 333 |
| 37 | 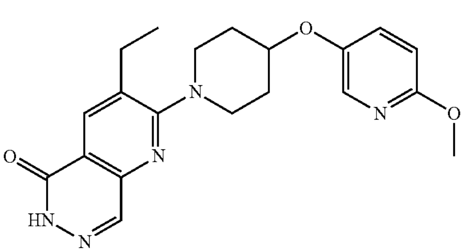 [SMILES: CCc1cc2c(=O)[nH]ncc2nc1N1CCC(Oc2ccc(OC)nc2)CC1] | 3-ethyl-2-(4-((6-methoxypyridin-3-yl)oxy)piperidin-1-yl)pyrido[2,3-d]pyridazin-5(6H)-one | 382 |
| 38 | 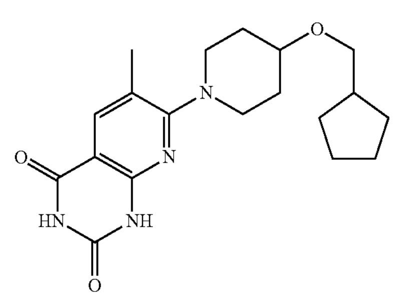 [SMILES: Cc1cc2c(=O)[nH]c(=O)[nH]c2nc1N1CCC(OCC2CCCC2)CC1] | 7-(4-(cyclopentyl-methoxy)piperidin-1-yl)-6-methylpyrido[2,3-d]pyrimidine-2,4(1H,3H)-dione | 359 |

TABLE 4-continued

| Example | Structure | Name | MS (M + 1) |
|---|---|---|---|
| 39 | 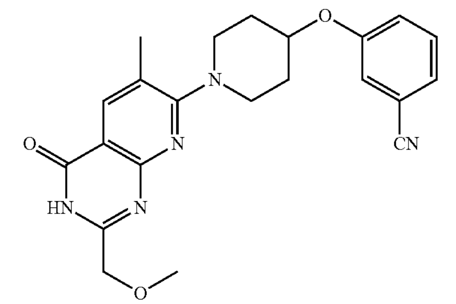 [SMILES: COCc1nc2nc(N3CCC(Oc4cccc(C#N)c4)CC3)c(C)cc2c(=O)[nH]1] | 3-((1-(2-(methoxymethyl)-6-methyl-4-oxo-3,4-dihydropyrido[2,3-d]pyrimidin-7-yl)piperidin-4-yl)oxy)benzonitrile | 406 |
| 40 | 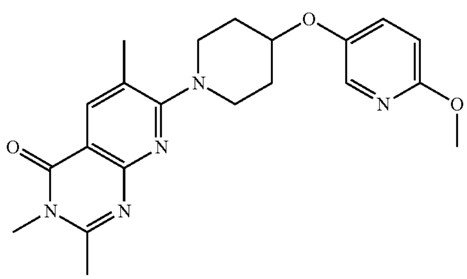 [SMILES: COc1ccc(OC2CCN(c3nc4nc(C)n(C)c(=O)c4cc3C)CC2)cn1] | 7-(4-((6-methoxypyridin-3-yl)oxy)piperidin-1-yl)-2,3,6-trimethyl-pyrido[2,3-d]pyrimidin-4(3H)-one | 396 |
| 41 | 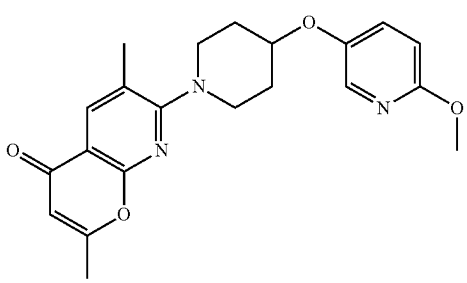 [SMILES: COc1ccc(OC2CCN(c3nc4oc(C)cc(=O)c4cc3C)CC2)cn1] | 7-(4-((6-methoxypyridin-3-yl)oxy)piperidin-1-yl)-2,6-dimethyl-4H-pyrano[2,3-b]pyridin-4-one | 382 |

Example 42

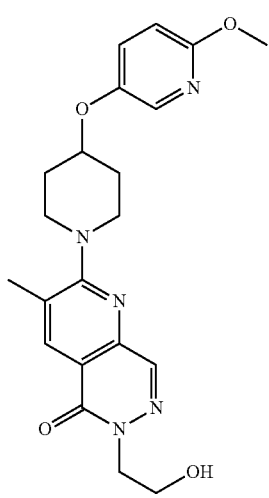

6-(2-Hydroxyethyl)-2-(4-((6-methoxypyridin-3-yl)oxy)piperidin-1-yl)-3-methylpyrido[2,3-d]pyridazin-5(6H)-one (Scheme 5)

Step 1: Methyl 2-(2-(4-((6-methoxypyridin-3-yl)oxy)piperidin-1-yl)-3-methyl-5-oxopyrido[2,3-d]pyridazin-6(5H)-yl)acetate To a solution of 2-(4-((6-methoxypyridin-3-yl)oxy)piperidin-1-yl)-3-methylpyrido[2,3-d]pyridazin-5(6H)-one (60 mg, 0.163 mmol) in THF (10 mL) was added NaH (60%, 13.1 mg, 0.327 mmol) at 15° C. After 15 min, methyl 2-bromoacetate (30 mg, 0.186 mmol) was added and the reaction was stirred for 2 h at RT. The reaction mixture was quenched with water (50 mL) and extracted with EtOAc (100 mL×3) and the combined organics were dried over anhydrous sodium sulfate, filtered and the filtrate was concentrated to afford the title compound. MS: 440 (M+1).

Step 2: 6-(2-Hydroxyethyl)-2-(4-((6-methoxypyridin-3-yl)oxy)piperidin-1-yl)-3-methylpyrido[2,3-d]pyridazin-5(6H)-one To a solution of methyl 2-(2-(4-((6-methoxypyridin-3-yl)oxy)piperidin-1-yl)-3-methyl-5-oxopyrido[2,3-d]pyridazin- 6(5H)-yl)acetate (50 mg, 0.114 mmol) in THF (10 mL) was added lithium borohydride (7.44 mg, 0.341 mmol) at 15° C. The reaction was stirred for 2 h and was then quenched with water (50 mL) and extracted with ethyl acetate (50 mL×3). The organic phases were dried over anhydrous sodium sulfate, filtered and the filtrate was concentrated. The resultant residue was purified by reverse phase HPLC (ACN/water with 0.1% TFA modifier) to yield the title compound. MS: 412 (M+1). $^1$H NMR (400 MHz, CDCl$_3$): δ8.25 (1H, s), 8.18 (1H, s), 7.88 (1H, d, J=2.8 Hz), 7.27 (1H, s), 6.71 (1H, d, J=8.8 Hz), 4.43 (3H, t, J=4.4 Hz), 4.05 (2H, m), 3.90 (3H, s), 3.65-3.75 (2H, m), 3.25-3.35 (2H, m), 2.44 (3H, s), 2.10-2.20 (2H, m), 1.95-2.04 (2H, m).

The following examples in table 5 were prepared according to scheme 5 using the procedure outlined in the synthesis of Example 42.

TABLE 5

| Example | Structure | Name | MS (M + 1) |
|---|---|---|---|
| 43 | 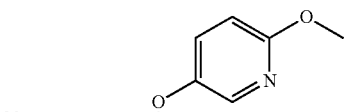 | 6-(2-hydroxyethyl)-3-methyl-2-(4-((1-methylcyclopropyl)methoxy)piperidin-1-yl)pyrido[2,3-d]pyridazin-5(6H)-one | 373 |

Example 44

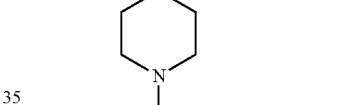
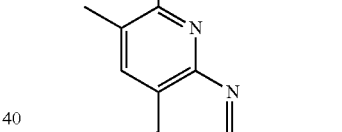
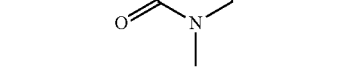

7-(4-((6-Methoxypyridin-3-yl)oxy)piperidin-1-yl)-3,6-dimethylpyrido[2,3-d]pyrimidin-4(3H)-one (Scheme 6)

To a solution of 7-(4-((6-methoxypyridin-3-yl)oxy)piperidin-1-yl)-6-methylpyrido[2,3-d]pyrimidin-4(3H)-one (15 mg, 0.041 mmol) in DMF (2 mL) was added sodium hydride (60%, 1.2 mg, 0.049 mmol) at 0° C. under an atmosphere of nitrogen. After 20 min, and MeI (3.06 μL, 0.049 mmol) was added and the reaction was stirred for 15 h at RT. The mixture was quenched with water (5 mL) and extracted with EtOAc (10 mL×3). The organic phases were dried over anhydrous sodium sulfate, filtered and the filtrate was concentrated. The resultant residue was purified by reverse phase HPLC (ACN/water with 0.1% TFA modifier) to yield the title compound. MS: 382 (M+1). $^1$H NMR (400 MHz, methanol-d$_4$): δ8.54 (1H, s), 8.15 (1H, s), 7.83 (1H, d, J=3.6 Hz), 7.44 (1H, dd, J=8.8, 3.2 Hz), 6.77 (1H, d, J=8.8 Hz), 4.50-4.57 (1H, m), 3.85 (3H, s), 3.75-3.84 (2H, m), 3.56 (3H, s), 3.35-3.44 (2H, m), 2.42 (3H, s), 2.08-2.15 (2H, m), 1.80-1.93 (2H, m).

The following examples in table 6 were prepared according to scheme 6 using the procedure outlined in the synthesis of Example 44.

TABLE 6

| Example | Structure | Name | MS (M + 1) |
|---|---|---|---|
| 45 | 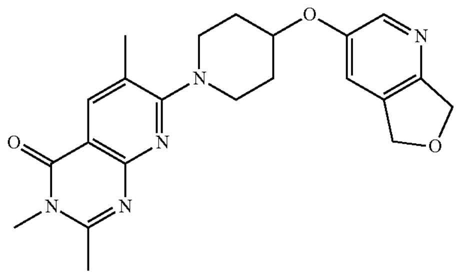 [SMILES: Cc1cc2c(=O)n(C)c(C)nc2nc1N1CCC(Oc2cnc3c(c2)COC3)CC1] | 7-(4-((5,7-dihydrofuro[3,4-b]pyridin-3-yl)oxy)piperidin-1-yl)-2,3,6-trimethyl-pyrido[2,3-d]pyrimidin-4(3H)-one | 430 |

Example 46

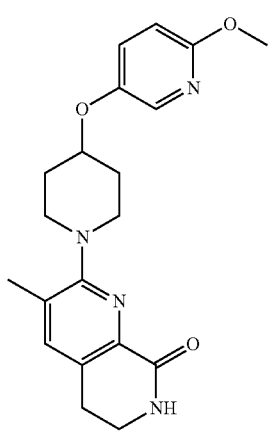

2-(4-((6-Methoxypyridin-3-yl)oxy)piperidin-1-yl)-3-methyl-6,7-dihydro-1,7-naphthyridin-8(51H)-one
(Scheme 7)

Step 1: Methyl 2-iodo-6-(4-((6-methoxypyridin-3-yl)oxy)piperidin-1-yl)-5-methylnicotinate A solution of methyl 6-chloro-2-iodo-5-methylnicotinate (500 mg, 1.61 mmol), 2-methoxy-5-(piperidin-4-yloxy)pyridine hydrochloride (393 mg, 1.605 mmol) and potassium carbonate (666 mg, 4.82 mmol) in DMF (10 mL) stirred for 5 h at 70° C. The mixture was cooled to RT and was diluted with water (50 mL), extracted with EtOAc (25 mL×3) and the combined organic layers were washed with brine (20 mL×3), dried over anhydrous sodium sulfate, filtered and concentrated. The residue was purified by silica gel chromatography (0-20% EtOAc/petroleum ether) to yield the title compound. MS: 484 (M+1).

Step 2: (2-Iodo-6-(4-((6-methoxypyridin-3-yl)oxy)piperidin-1-yl)-5-methylpyridin-3-yl)methanol To a solution of methyl 2-iodo-6-(4-((6-methoxypyridin-3-yl)oxy)piperidin-1-yl)-5-methylnicotinate (215 mg, 0.445 mmol) in THF (6 mL) was added LiBH$_4$ (14.5 mg, 0.667 mmol). The reaction was stirred for 2 h at 15° C. before methanol (1 mL) was added and the mixture was stirred for an additional 1 h. The mixture was quenched with water (30 mL), extracted with EtOAc (15 mL×3). The combined organic layers were dried over anhydrous sodium sulfate, filtered and the filtrate was concentrated in vacuo to give the title compound. MS: 456 (M+1).

Step 3: (2-Iodo-6-(4-((6-methoxypyridin-3-yl)oxy)piperidin-1-yl)-5-methylpyridin-3-yl)methyl methanesulfonate To a solution of (2-iodo-6-(4-((6-methoxypyridin-3-yl)oxy)piperidin-1-yl)-5-methylpyridin-3-yl)methanol (170 mg, 0.373 mmol) and triethylamine (0.156 ml, 1.120 mmol) in DCM (5 mL) was added methanesulfonyl chloride (86 mg, 0.747 mmol). The reaction was stirred for 18 h at 15° C. before being quenched with water (40 mL) and extracted with DCM (20 mL×3). The combined organic layers were dried over anhydrous sodium sulfate, filtered and concentrated in vacuo to afford the title compound. MS: 438 (M-OMs$^+$).

Step 4: 2-(2-Iodo-6-(4-((6-methoxypyridin-3-yl)oxy)piperidin-1-yl)-5-methylpyridin-3-yl)acetonitrile A solution of (2-iodo-6-(4-((6-methoxypyridin-3-yl)oxy)piperidin-1-yl)-5-methylpyridin-3-yl)methyl methanesulfonate (200 mg, 0.161 mmol) and sodium cyanide (15.80 mg, 0.322 mmol) in DMF (6 mL) was stirred for 8 h at 50° C. The mixture was cooled to RT, quenched with water (30 mL) and extracted with EtOAc (15 mL×3). The combined organic layers were washed with brine (15 mL×2), dried over anhydrous sodium sulfate, filtered and concentrated. The residue was purified by prep-TLC (2:1 petroleum ether/EtOAc) to yield the title compound. MS: 465 (M+1).

Step 5: Methyl 3-(cyanomethyl)-6-(4((6-methoxy-pyridin-3-yl)oxy)piperidin-1-yl)-5-methylpicolinate A solution of 2-(2-iodo-6-(4-((6-methoxypyridin-3-yl)oxy)piperidin-1-yl)-5-methylpyridin-3-yl)acetonitrile (30 mg, 0.032 mmol), [1,1'-bis(diphenylphosphino)ferrocene] dichloropalladium (II) (2.364 mg, 3.23 µmol) and triethylamine (13.1 mg, 0.129 mmol) in MeOH (5 mL) was stirred at 50° C. for 2 h under CO (50 psi). The mixture was filtered and the filtrate was concentrated and the residue was purified by prep-TLC (2:1 petroleum ether/EtOAc) to yield the title compound. MS: 397 (M+1).

Step 6: 2-(4-((6-Methoxypyridin-3-yl)oxy)piperidin-1-yl)-3-methyl-6,7-dihydro-1,7-naphthyridin-8(5H)-one A mixture of methyl 3-(cyanomethyl)-6-(4-((6-methoxy-pyridin-3-yl)oxy)piperidin-1-yl)-5-methylpicolinate (13 mg, 0.033 mmol), MeOH (5 mL), aqueous NH$_3$ (29% wt, 0.5 mL) and nickel (1.93 mg, 0.033 mmol) was stirred for 2 h at 15° C. under hydrogen (50 psi). The mixture was filtered and the filtrate was concentrated in vacuo. The resultant residue was purified by reverse phase HPLC (ACN/water with 0.1% TFA modifier) to yield the title compound. MS: 369 (M+1) $^1$H NMR (400 MHz, methanol-$d_4$): δ7.85 (1H, d, J=2.4 Hz), 7.60 (1H, s), 7.49 (1H, dd, J=8.8 Hz, 2.8 Hz), 6.82 (1H, d, J=8.8 Hz), 4.47-4.52 (1H, m), 3.87 (3H, s), 3.46-3.60 (4H, m), 3.19-3.25 (2H, m), 2.95 (2H, t, J=6.4 Hz), 2.39 (3H, s), 2.09-2.18 (2H, m), 1.81-1.92 (2H, m).

Example 47

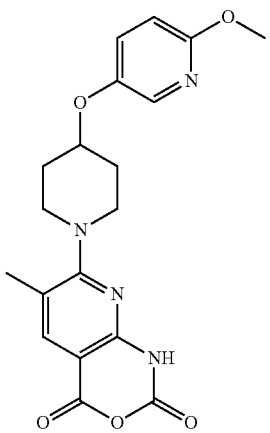

7-(4-((6-Methoxypyridin-3-yl)oxy)piperidin-1-yl)-6-methyl-2H-pyrido[2,3-d][1,3]oxazine-2,4(1H)-dione (Scheme 8)

Aqueous NaOH (2 M, 0.671 mL, 1.343 mmol) was added to a stirred mixture of methyl 2-amino-6-(4-((6-methoxypyridin-3-yl)oxy)piperidin-1-yl)-5-methylnicotinate (50 mg, 0.134 mmol) in MeOH (5 mL) and THF (5 mL). The mixture was stirred at 60° C. for 16 h before the volatiles were removed in vacuo. The residue was dissolved in THF (5 mL) and bis(trichloromethyl) carbonate (39.8 mg, 0.134 mmol) was added to the solution. The resulting mixture was stirred at 70° C. for 16 h before the volatiles were removed in vacuo. The residue was purified by column chromatography on silica gel (DCM/MeOH) to afford the title compound. MS: 385 (M+1). $^1$H NMR (500 MHz, CDCl$_3$): δ7.89 (2H, br s), 7.82 (1H, s), 7.28 (1H, dd, J=8.5, 2.8 Hz), 6.74 (1H, d, J=8.5 Hz), 4.48 (1H, m), 3.93 (3H, s), 3.77 (2H, m), 3.47 (2H, m), 2.33 (3H, s), 2.09 (2H, m), 1.96 (2H, m).

Example 48

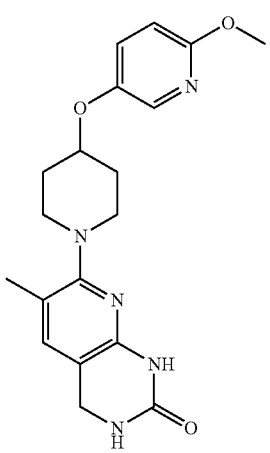

7-(4-((6-Methoxypyridin-3-yl)oxy)piperidin-1-yl)-6-methyl-3,4-dihydropyrido[2,3-d]pyrimidin-2(1H)-one (Scheme 9)

Step 1: 2-Chloro-6-(4-((6-methoxypyridin-3-yl)oxy) piperidin-1-yl)-5-methylnicotinonitrile To a solution of 2-methoxy-5-(piperidin-4-yloxy)pyridine hydrochloride (432 mg, 1.76 mmol) and 2,6-dichloro-5-methylnicotinonitrile (prepared according to literature, see: Villarelle, D. V., et al. *Tetrahedron* 2004, 2, 275-283, 300 mg, 1.60 mmol) in DMF (8 mL) was added potassium carbonate (665 mg, 4.81 mmol) at RT. The resulting mixture was stirred at RT for 2 h and was then diluted with water (50 mL) and extracted with EtOAc (50 mL×3). The combined organic layers were washed with water (20 mL) and brine (20 mL), dried over anhydrous sodium sulfate, filtered and concentrated. The crude product was purified by silica gel chromatography (100:1-3:1 petroleum ether/EtOAc) to give the title compound. MS: 359 (M+1).

Step 2: 2-Amino-6-(4-((6-methoxypyridin-3-yl)oxy) piperidin-1-yl)-5-methylnicotinonitrile A mixture of 2-chloro-6-(4-((6-methoxypyridin-3-yl)oxy) piperidin-1-yl)-5-methylnicotinonitrile (200 mg, 0.557 mmol) and ammonia (4 M in EtOH, 10 mL) was heated to 100° C. in a sealed tube for 24 h. The reaction was cooled to RT and concentrated under reduced pressure. The residue was purified by prep-TLC (3:1 petroleum ether/EtOAc) to afford the title compound. MS: 340 (M+1).

Step 3: 3-(Aminomethyl)-6-(4-((6-methoxypyridin-3-yl)oxy)piperidin-1-yl)-5-methylpyridin-2-amine A mixture of 2-amino-6-(4-((6-methoxypyridin-3-yl)oxy) piperidin-1-yl)-5-methylnicotinonitrile (120 mg, 0.354 mmol), MeOH (5 mL), aqueous NH$_3$ (29 wt %, 0.1 mL) and nickel (20.8 mg, 0.354 mmol) was stirred under a hydrogen atmosphere (50 psi) for 2 h at 15° C. The mixture was filtered and the filtrate was concentrated in vacuo to give the title compound. MS: 344 (M+1).

Step 4: 7-(4-((6-methoxypyridin-3-yl)oxy)piperidin-1-yl)-6-methyl-3,4-dihydropyrido[2,3-d]pyrimidin-2 (1H)-one To a solution of 3-(aminomethyl)-6-(4-((6-methoxypyridin-3-yl)oxy)piperidin-1-yl)-5-methylpyridin-2-amine (60 mg, 0.175 mmol) in THF (2 mL) was added CDI (283 mg, 1.747 mmol) at 0° C. The reaction mixture was stirred for 1 h at 15° C. before being quenched with water (0.5 mL) at 0° C. The mixture was directly purified by reverse phase HPLC (ACN/water with 0.1% ammonium hydroxide modifier) to yield the title compound. MS: 370 (M+1). $^1$H NMR (400 MHz, CDCl$_3$): δ7.95 (1H, d, J=2.4 Hz), 7.02 (1H, s), 6.72 (1H, s), 6.63 (1H, d, J=8.8 Hz), 4.32 (2H, s), 4.24 (1H, m), 3.83 (3H, s), 3.29-3.32 (2H, m), 2.86-2.92 (2H, m), 2.20 (3H, s), 2.01-2.13 (2H, m), 1.78-1.83 (2H, m).

Example 49

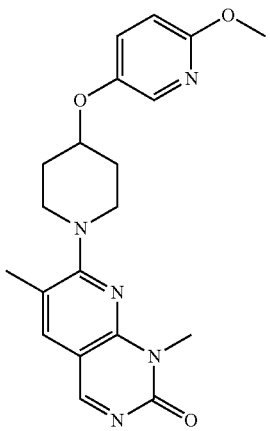

7-(4-((6-Methoxypyridin-3-yl)oxy)piperidin-1-yl)-1,6-dimethylpyrido[2,3-d]pyrimidin-2(1H)-one (Scheme 9)

Step 1: 2-Chloro-6-(4-((6-methoxypyridin-3-yl)oxy)piperidin-1-yl)-5-methylnicotinonitrile To a solution of 2-methoxy-5-(piperidin-4-yloxy)pyridine hydrochloride (432 mg, 1.76 mmol) and 2,6-dichloro-5-methylnicotinonitrile (prepared according to literature, see: Villarelle, D. V., et al. *Tetrahedron* 2004, 2, 275-283, 300 mg, 1.60 mmol) in DMF (8 mL) was added potassium carbonate (665 mg, 4.81 mmol) at RT. The resulting mixture was stirred at RT for 2 h and was then diluted with water (50 mL) and extracted with EtOAc (50 mL×3). The combined organic layers were washed with water (20 mL) and brine (20 mL), dried over anhydrous sodium sulfate, filtered and concentrated. The crude product was purified by silica gel chromatography (100:1-5:1 petroleum ether/EtOAc) to give the title compound. MS: 359 (M+1).

Step 2: 6-(4-((6-Methoxypyridin-3-yl)oxy)piperidin-1-yl)-5-methyl-2-(methylamino)nicotinonitrile A mixture of 2-chloro-6-(4-((6-methoxypyridin-3-yl)oxy)piperidin-1-yl)-5-methylnicotinonitrile (200 mg, 0.557 mmol) and methylamine (33 wt % in EtOH, 10 mL) was heated to 100° C. in a sealed tube for 48 h. The reaction was cooled to RT and concentrated under reduced pressure. The residue was purified by prep-TLC (1:1 petroleum ether/EtOAc) to afford the title compound. MS: 354 (M+1).

Step 3: 3-(Aminomethyl)-6-(4-((6-methoxypyridin-3-yl)oxy)piperidin-1-yl)-N,5-dimethylpyridin-2-amine A mixture of 6-(4-((6-methoxypyridin-3-yl)oxy)piperidin-1-yl)-5-methyl-2-(methylamino)nicotinonitrile (30 mg, 0.085 mmol), MeOH (5 mL), aqueous NH₃ (29 wt %, 0.1 mL) and nickel (4.98 mg, 0.085 mmol) was stirred under a hydrogen atmosphere (50 psi) for 2 h at 15° C. Aqueous HCl (2 M, 3 mL) was added to the reaction and the mixture was filtered and the filtrate was concentrated in vacuo to afford the title compound. MS: 358 (M+1).

Step 4: 7-(4-((6-Methoxypyridin-3-yl)oxy)piperidin-1-yl)-1,6-dimethylpyrido[2,3-d]pyrimidin-2(1H)-one To a solution of sodium bicarbonate (35.3 mg, 0.420 mmol) in water (1 mL) was added a solution of bis(trichloromethyl) carbonate (49.8 mg, 0.168 mmol) in DCM (1 mL) dropwise at 0° C. A solution of 3-(aminomethyl)-6-(4-((6-methoxypyridin-3-yl)oxy)piperidin-1-yl)-N,5-dimethylpyridin-2-amine (30 mg, 0.084 mmol) in water (1.0 mL) was added dropwise slowly to the mixture. The reaction was stirred at 0° C. for 20 min before being quenched with aqueous K₂CO₃ (saturated, 3 mL). The mixture was diluted with water (30 mL) and extracted with EtOAc (30 mL×3). The combined organic layers were washed with brine (30 mL), dried over anhydrous sodium sulfate, filtered, and concentrated in vacuo. The residue was purified by reverse phase HPLC (ACN/water with 0.1% TFA modifier) to yield the title compound. MS: 382 (M+1). $^1$NMR (400 MHz, methanol-d₄): δ8.77 (1H, s), 7.87 (1H, d, J=2.4 Hz), 7.82 (1H, s), 7.45 (1H, dd, J=9.2, 2.8 Hz), 6.78 (1H, d, J=9.2 Hz), 4.14-4.20 (2H, m), 3.95-4.01 (2H, m), 3.86 (4H, s), 3.71 (3H, s), 2.46 (3H, s), 2.13-2.19 (2H, m), 1.97-2.03 (2H, m).

Example 50

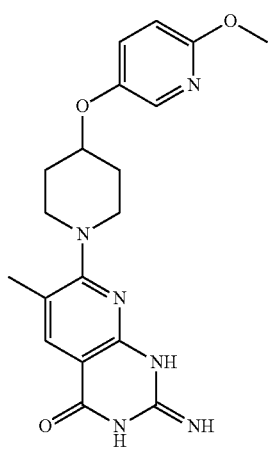

2-Imino-7-(4-((6-methoxypyridin-3-yl)oxy)piperidin-1-yl)-6-methyl-2,3-dihydropyrido[2,3-d]pyrimidin-4(1H)-one (Scheme 10)

Step 1: Methyl 2-iodo-6-(4-((6-methoxypyridin-3-yl)oxy)piperidin-1-yl)-5-methylnicotinate A mixture of methyl 6-chloro-2-iodo-5-methylnicotinate (1 g, 3.21 mmol), 2-methoxy-5-(piperidin-4-yloxy)pyridine hydrochloride (0.786 g, 3.21 mmol) and potassium carbonate (1.33 g, 9.63 mmol) in DMF (20 mL) was stirred for 5 h at 70° C. The reaction was quenched with water (50 mL), extracted with EtOAc (25 mL×3) and the combined organic layers were washed with brine (20 mL×3), dried over anhydrous sodium sulfate, filtered and concentrated. The residue was purified silica gel chromatography (10:1 hexanes/EtOAc) to give the title compound. MS: 484 (M+1).

Step 2: 2-Imino-7-(4-((6-methoxypyridin-3-yl)oxy)piperidin-1-yl)-6-methyl-2,3-dihydropyrido[2,3-d]pyrimidin-4(1H)-one Guanidine hydrochloride (37.6 mg, 0.393 mmol) was added to a stirred mixture of methyl 2-iodo-6-(4-((6-methoxypyridin-3-yl)oxy)piperidin-1-yl)-5-methylnicotinate (95 mg, 0.197 mmol) in t-BuOH (3 mL). The mixture was stirred at 90° C. for 16 h and was concentrated to dryness. The residue was purified by silica gel chromatography (DCM/MeOH) to give the title compound. MS: 383

(M+1). ¹H NMR (500 MHz, DMSO-d₆,): δ7.91 (1H, d, J=3 Hz), 7.80 (1H, s), 7.46 (1H, dd, J=8.9, 3.0 Hz), 6.75 (1H, d, J=8.9 Hz), 6.50 (3H, br s), 4.51 (1H, m), 3.79 (3H, s), 3.57 (2H, m), 3.12 (2H, m), 2.23 (3H, s), 2.02 (2H, m), 1.73 (2H, m).

Example 51

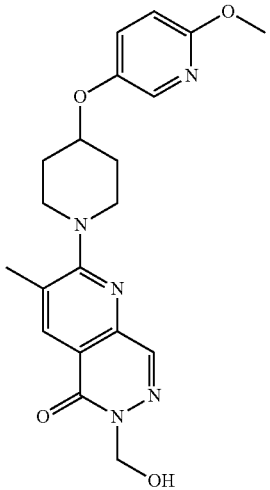

6-(Hydroxymethyl)-2-(4-((6-methoxypyridin-3-yl) oxy)piperidin-1-yl)-3-methylpyrido[2,3-d]pyridazin-5(6H)-one (Scheme 11)

To a solution of compound 3-((1-(3-methyl-5-oxo-5,6-dihydropyrido[2,3-d]pyridazin-2-yl)piperidin-4-yl)oxy) benzonitrile (600 mg, 1.66 mmol) in MeOH (10 mL) was added formaldehyde (2.7 g, 33.2 mmol). The reaction was stirred at 70° C. for 40 h before being concentrated to dryness. The residue was purified by silica gel chromatography (0-60% EtOAc/petroleum ether) to afford the title compound. MS: 392 (M+1). ¹H NMR (400 MHz, methanol-d₄): δ8.32-8.35 (m, 2H), 7.46-7.50 (m, 1H), 7.38 (s, 1H), 7.30-7.34 (m, 2H), 5.55 (s, 2H), 4.75-4.82 (m, 1H), 3.84-3.89 (m, 2H), 3.57-3.62 (m, 2H), 2.54 (s, 3H), 2.20-2.26 (m, 2H), 2.01-2.03 (m, 2H).

Example 52

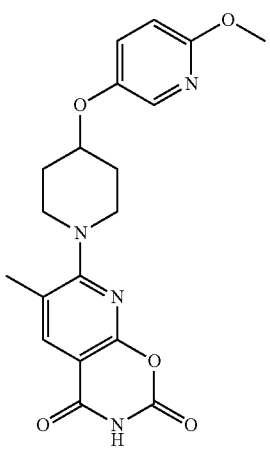

7-(4-((6-Methoxypyridin-3-yl)oxy)piperidin-1-yl)-6-methyl-2H-pyrido[3,2-e][1,3]oxazine-2,4(3H)-dione (Scheme 12)

Step 1: Methyl 2-hydroxy-6-(4-((6-methoxypyridin-3-yl)oxy)piperidin-1-yl)-5-methylnicotinate To a solution of methyl 6-chloro-2-hydroxy-5-methylnicotinate (intermediate D, 300 mg, 1.49 mmol) and 2-methoxy-5-(piperidin-4-yloxy)pyridine, HCl (473 mg, 1.93 mmol) in DMF (5 mL) was added DIPEA (0.780 mL, 4.46 mmol). The reaction mixture was stirred at 80° C. for 1 h. Water (10 mL) was added and the mixture was extracted with EtOAc (10 mL×3). The combined organic fractions were washed with water (20 mL×3), dried over anhydrous sodium sulfate, filtered and the volatiles were evaporated under reduced pressure. The residue was purified by silica gel chromatography (0-40% EtOAc/petroleum ether) to yield the title compound. MS: 374 (M+1).

Step 2: 2-Hydroxy-6-(4-((6-methoxypyridin-3-yl) oxy)piperidin-1-yl)-5-methylnicotinic acid A solution of methyl 2-hydroxy-6-(4-((6-methoxypyridin-3-yl)oxy)piperidin-1-yl)-5-methylnicotinate (220 mg, 0.589 mmol) and NaOH (707 mg, 17.68 mmol) in 1:1 MeOH:water (10 mL) was stirred at 60° C. for 15 h. Aqueous HCl (6 M) was added to pH~6 and the mixture was extracted with DCM (20 mL×3). The combined organic fractions were washed with water (40 mL×3), dried over anhydrous sodium sulfate, filtered and concentrated to afford the title compound as a crude solid. MS: 360 (M+1).

Step 3: 2-(3-Carbamoyl-6-(4-((6-methoxypyridin-3-yl)oxy)piperidin-1-yl)-5-methylpyridin-2-yl)-1,1,3,3-tetramethylisouronium hexafluorophosphate(V)

To a solution of 2-hydroxy-6-(4-((6-methoxypyridin-3-yl) oxy)piperidin-1-yl)-5-methylnicotinic acid (100 mg, 0.278 mmol) and ammonium chloride (22.3 mg, 0.417 mmol) in DCM (3 mL) was added HATU (159 mg, 0.417 mmol) and TEA (0.310 mL, 2.23 mmol). The reaction mixture was stirred at 20° C. for 2 h before the volatiles were removed under reduced pressure to afford the title compound. MS: 457 (M⁺-PF₆).

Step 4: 7-(4-((6-Methoxypyridin-3-yl)oxy)piperidin-1-yl)-6-methyl-2H-pyrido[3,2-e][1,3]oxazine-2,4 (3H)-dione To a solution of 2-(3-carbamoyl-6-(4-((6-methoxypyridin-3-yl)oxy)piperidin-1-yl)-5-methylpyridin-2-yl)-1,1,3,3-tetramethylisouronium hexafluorophosphate(V) (200 mg, 0.437 mmol) in THF (4 mL) was added conc. HCl (4 mL). The reaction mixture was stirred at 80° C. for 2 h and was then cooled to RT. Aqueous NaHCO₃ (saturated) was added until the reaction mixture was pH-9. The mixture was extracted with DCM (10 mL×3) and the combined organic fractions were washed with water (20 mL), dried over anhydrous sodium sulfate, filtered and concentrated. The residue was purified by prep-TLC (10:1 DCM:MeOH) to give the title compound. MS: 385 (M+1). ¹H NMR (400 MHz, DMSO-d₆): δ11.86 (1H, s), 7.92 (2H, d, J=4.4 Hz), 7.48 (1H, dd, J=9.2 Hz 3.2 Hz), 6.78 (1H, d, J=9.2 Hz), 4.56-4.59 (1H, m), 3.79 (3H, s), 3.69-3.71 (2H, m), 3.27-3.30 (2H, m), 2.30 (3H, s), 2.03-2.08 (2H, m), 1.70-1.75 (2H, m).

Example 53

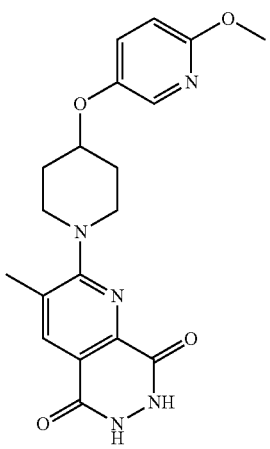

2-(4-((6-Methoxypyridin-3-yl)oxy)piperidin-1-yl)-3-methyl-6,7-dihydropyrido[2,3-d]pyridazine-5,8-dione (Scheme 13)

Step 1: Methyl 2-cyano-6-(4-((6-methoxypyridin-3-yl)oxy)piperidin-1-yl)-5-methylnicotinate A mixture of 2-methoxy-5-(piperidin-4-yloxy)pyridine hydrochloride (300 mg, 1.23 mmol), methyl 6-chloro-2-cyano-5-methylnicotinate (258 mg, 1.23 mmol) and DIPEA (475 mg, 3.68 mmol) in dry DMF (25 mL) was stirred at 80° C. for 15 h. The reaction was cooled to RT and was treated with water (100 mL) and extracted with EtOAc (100 mL×3). The combined organic layers were dried over anhydrous sodium sulfate, filtered and concentrated to give the title compound. MS: 405 (M+1).

Step 2: 6-(4-((6-Methoxypyridin-3-yl)oxy)piperidin-1-yl)-5-methylpyridine-2,3-dicarboxylic acid A mixture of methyl 2-cyano-6-(4-((6-methoxypyridin-3-yl)oxy)piperidin-1-yl)-5-methylnicotinate (400 mg, 1.05 mmol) and NaOH (167 mg, 4.18 mmol) in 1:1 water:i-PrOH (10 mL) was stirred at 80° C. for 16 h. The mixture was concentrated and diluted with EtOAc (30 mL) and water (20 mL). The aqueous phase was adjusted pH~3 with aqueous HCl (2 M) and was extracted with EtOAc (30 mL×3). The combined organic layers were dried over anhydrous sodium sulfate, filtered and the filtrate was concentrated in vacuum to afford the title compound. MS: 388 (M+1).

Step 3: Dimethyl 6-(4-((6-methoxypyridin-3-yl)oxy)piperidin-1-yl)-5-methylpyridine-2,3-dicarboxylate A solution of 6-(4-((6-methoxypyridin-3-yl)oxy)piperidin-1-yl)-5-methylpyridine-2,3-dicarboxylic acid (400 mg, 1.03 mmol) in MeOH (10 mL) and conc. HCl (2.0 mL, 24.4 mmol) was stirred at 80° C. for 16 h. The mixture was concentrated and diluted with EtOAc (30 mL) and water (20 mL). The combined organics were washed with water (10 mL), brine (10 mL), dried over anhydrous sodium sulfate, filtered and concentrated. The residue was purified by silica gel chromatography (10-80% EtOAc/petroleum ether) to give the title compound. MS: 438 (M+1).

Step 4: 2-(4-((6-methoxypyridin-3-yl)oxy)piperidin-1-yl)-3-methyl-6,7-dihydropyrido[2,3-d]pyridazine-5,8-dione A mixture of dimethyl 6-(4-((6-methoxypyridin-3-yl)oxy)piperidin-1-yl)-5-methylpyridine-2,3-dicarboxylate (200 mg, 0.481 mmol) and hydrazine (2.0 mL, 63.7 mmol) in MeOH (20 mL) was stirred at 80° C. for 16 h. The mixture was concentrated and purified by reverse phase HPLC (ACN/water with 0.1% ammonium hydroxide modifier) to afford the title compound. MS: 384 (M+1). $^1$H NMR (400 MHz, methanol-$d_4$): δ8.13 (1H, s), 7.85 (1H, d, J=3.2 Hz), 7.44 (1H, dd, J=8.8, 2.8 Hz), 6.76 (1H, d, J=9.2 Hz), 4.48-4.53 (1H, m), 3.85 (3H, s), 3.72-3.78 (2H, m), 3.34-3.36 (2H, m), 2.47 (3H, s), 2.12-2.16 (2H, m), 1.85-1.94 (2H, m).

Example 54

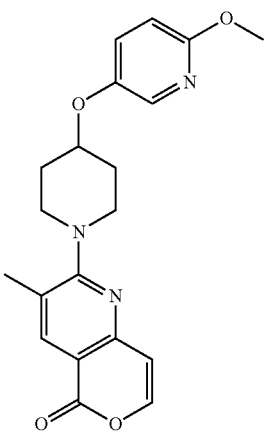

2-(4-((6-Methoxypyridin-3-yl)oxy)piperidin-1-yl)-3-methyl-5H-pyrano[4,3-b]pyridin-5-one (Scheme 14)

Step 1: Methyl 2-iodo-6-(4-((6-methoxypyridin-3-yl)oxy)piperidin-1-yl)-5-methylnicotinate A mixture of 2-methoxy-5-(piperidin-4-yloxy)pyridine hydrochloride (283 mg, 1.16 mmol), methyl 6-chloro-2-iodo-5-methylnicotinate (300 mg, 0.963 mmol), DIPEA (0.168 mL, 0.963 mmol) in in DMF (3 mL) was stirred at 30° C. for 12 h. The reaction mixture was diluted with water (50 mL) and extracted with ethyl acetate (30 mL×3) and the combined organic layers were washed with brine (10 mL), dried over anhydrous sodium sulfate, filtered and concentrated. The residue was purified by prep-TLC (50% ethyl acetate/petroleum ether) to furnish the title compound. MS: 483 (M+1).

Step 2: (E)-Methyl 2-(2-ethoxyvinyl)-6-(4-((6-methoxypyridin-3-yl)oxy)piperidin-1-yl)-5-methylnicotinate To a solution of methyl 2-iodo-6-(4-((6-methoxypyridin-3-yl)oxy)piperidin-1-yl)-5-methylnicotinate (100 mg, 0.207 mmol) in 1,4-dioxane (5 mL) and water (1 mL) was added (Z)-2-(2-ethoxyvinyl)-4,4,5,5-tetramethyl-1,3,2-dioxaborolane (41.0 mg, 0.207 mmol), tribasic potassium phosphate (132 mg, 0.621 mmol) and PdCl$_2$(dppf) (76 mg, 0.103 mmol) under an inert nitrogen atmosphere. The reaction mixture was stirred at 80° C. for 12 h before cooling to RT and diluting with water (50 mL) and extracting with EtOAc (100 mL×3). The combined organic layers were washed with brine (10 mL), dried over anhydrous sodium sulfate, filtered and the filtrate was concentrated. The residue was purified by prep-TLC (25% EtOAc/petroleum ether) to give the title compound. MS: 428 (M+1).

Step 3: 2-(4-((6-Methoxypyridin-3-yl)oxy)piperidin-1-yl)-3-methyl-5H-pyrano[4,3-b]pyridin-5-one To a solution of (E)-methyl 2-(2-ethoxyvinyl)-6-(4-((6-methoxypyridin-3-yl)oxy)piperidin-1-yl)-5-methylnicotinate (40 mg, 0.094 mmol) in EtOH (3 mL) was added conc. HCl (7.68 μL, 0.094 mmol). The reaction mixture was stirred at 80° C. for 2 h before cooling to RT and diluting with water (50 mL) and extracting with EtOAc (30 mL×3). The combined organic layers were washed with brine (10 mL), dried over anhydrous sodium sulfate, filtered and the filtrate was concentrated. The residue was purified by reverse phase HPLC (ACN/water with 0.1% TFA modifier) to afford the title compound. MS: 368 (M+1). $^1$H NMR (400 MHz, methanol-d$_4$): δ8.08 (1H, s), 7.88 (1H, d, J=3.2 Hz), 7.56 (2H, dd, J=9.2, 3.6 Hz), 6.87 (1H, d, J=9.2 Hz), 6.62 (1H, d, J=5.6 Hz), 4.54-4.60 (1H, m), 3.90 (3H, s), 3.74-3.80 (2H, m), 3.37-3.43 (2H, m), 2.40 (3H, s), 2.13-2.40 (2H, m), 1.86-1.93 (2H, m).

Example 55

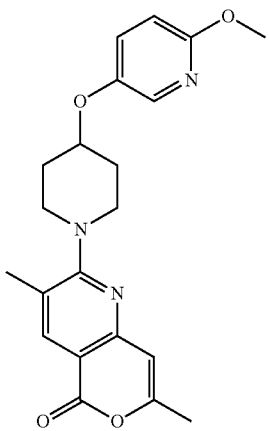

2-(4-((6-Methoxypyridin-3-yl)oxy)piperidin-1-yl)-3,7-dimethyl-5H-pyrano[4,3-b]pyridin-5-one (Scheme 15)

Step 1: Methyl 2-iodo-6-(4-((6-methoxypyridin-3-yl)oxy)piperidin-1-yl)-5-methylnicotinate A mixture of methyl 6-chloro-2-iodo-5-methylnicotinate (200 mg, 0.642 mmol), DIPEA (415 mg, 3.21 mmol) and 2-methoxy-5-(piperidin-4-yloxy)pyridine, 2 HCl (271 mg, 0.963 mmol) in DMF (5 mL) was stirred at 80° C. for 18 h. The reaction was diluted with water (20 mL), extracted with ethyl acetate (10 mL×3), dried over anhydrous sodium sulfate, filtered, and concentrated. The residue was purified by prep-TLC (10/1 petroleum ether/EtOAc) to furnish the title compound. MS: 484 (M+1).

Step 2: 2-Iodo-6-(4-((6-methoxypyridin-3-yl)oxy)piperidin-1-yl)-5-methylnicotinic acid To a solution of methyl 2-iodo-6-(4-((6-methoxypyridin-3-yl)oxy)piperidin-1-yl)-5-methylnicotinate (120 mg, 0.248 mmol) in MeOH (3 mL) and water (0.6 mL) was added lithium hydroxide, H$_2$O (20.8 mg, 0.497 mmol). The resulting mixture was stirred at 20° C. for 12 h before the volatiles were removed under reduced pressure. The residue was dissolved in water (10 mL) and aqueous HCl (1 M) was added to adjust the pH~7 before extracting the aqueous phase with ethyl acetate (10 mL×3). The combined organics were dried over anhydrous sodium sulfate, filtered, and concentrated to dryness to afford the title compound. MS: 470 (M+1).

Step 3: 2-(4-((6-Methoxypyridin-3-yl)oxy)piperidin-1-yl)-3,7-dimethyl-5H-pyrano[4,3-b]pyridin-5-one To a solution of pentane-2,4-dione (9.81 mg, 0.098 mmol) and 2-iodo-6-(4-((6-methoxypyridin-3-yl)oxy)piperidin-1-yl)-5-methylnicotinic acid (23 mg, 0.049 mmol) in acetonitrile (2 mL) was added cesium carbonate (16.0 mg, 0.049 mmol). The resulting mixture was stirred at 110° C. for 12 h and was cooled to RT before being quenched with water (10 mL) and extracting with ethyl acetate (10 mL×3). The combined organic layers were dried over anhydrous sodium sulfate, filtered and the filtrate was concentrated. The residue was purified by reverse phase HPLC (ACN/water with 0.1% TFA modifier) to afford the title compound. MS: 382 (M+1). $^1$H NMR (400 MHz, CDCl$_3$) δ: 8.15 (1H, s), 8.00 (1H, s), 7.43 (1H, d, J=8.4 Hz), 6.83 (1H, d, J=9.2 Hz), 6.54 (1H, s), 4.51-4.54 (1H, m), 3.97 (3H, s), 3.74-3.86 (2H, m), 3.43-3.56 (2H, m), 2.40 (3H, s), 2.32 (3H, s), 2.08-2.22 (2H, m), 1.98-2.02 (2H, m).

Assay Protocol

The utility of the compounds as M4 muscarinic receptor allosteric modulators may be demonstrated by methodology known in the art, including by the assay described herein.

CHO-K1 cells stably transfected with human M4 receptor and chimeric G-protein Gαqi5 are thawed from liquid N$_2$ storage, resuspended in growth medium, plated in black, clear bottom 384 well plates, and incubated 16-20 hours at 37° C., 5% CO$_2$.

On the day of assay, growth medium is removed, the cells are washed 2 times with wash buffer, and cells are incubated in dye loading buffer at 37° C., 5% CO$_2$ for ~1 h. Following dye loading the cell plates are placed in a FLIPR Tetra instrument and while monitoring dye fluorescence (excitation 470-495 nM/emission 515-575 nM), 10 uL of test substance at increasing concentrations is added, and fluorescence values are recorded for 4 min. Next, 10 uL of acetylcholine is added (final concentration calculated so as to achieve 20% of the maximum acetylcholine response), and the fluorescence reading is continued for 3.5 min. In some cases, a third addition of acetylcholine (final concentration calculated to achieve 70% of the maximal acetylcholine response) is performed.

The following table shows representative data for the compounds of the Examples as modulators of the M4 muscarinic acetylcholine receptor as determined by the assays described herein. Such results are indicative of the intrinsic activity of the compounds for use as allosteric modulators of the M4 muscarinic acetylcholine receptor.

TABLE 7

| Example | M4 PAM IP (nM) |
|---|---|
| 1 | 393 |
| 2 | 988 |
| 3 | 453 |
| 4 | 431 |
| 5 | 366 |
| 6 | 59 |
| 7 | 41 |
| 8 | 18 |
| 9 | 140 |
| 10 | 34 |
| 11 | 22 |
| 12 | 114 |
| 13 | 61 |
| 14 | 80 |
| 15 | 23 |
| 16 | 213 |
| 17 | 121 |
| 18 | 254 |
| 19 | 74 |
| 20 | 50 |
| 21 | 26 |
| 22 | 158 |
| 23 | 158 |
| 24 | 18 |
| 25 | 19 |
| 26 | 90 |
| 27 | 494 |
| 28 | 95 |
| 29 | 53 |
| 30 | 546 |
| 31 | 42 |
| 32 | 236 |
| 33 | 52 |
| 34 | 361 |
| 35 | 38 |
| 36 | 138 |
| 37 | 71 |
| 38 | 112 |
| 39 | 32 |
| 40 | 155 |
| 41 | 100 |
| 42 | 110 |
| 43 | 133 |
| 44 | 135 |
| 45 | 361 |
| 46 | 587 |
| 47 | 78 |
| 48 | 272 |
| 49 | 210 |
| 50 | 469 |
| 51 | 46 |
| 52 | 15 |
| 53 | 260 |
| 54 | 85 |
| 55 | 70 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of the formula I:

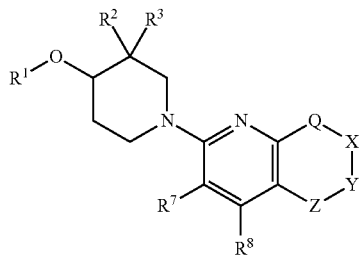

wherein:

the group:

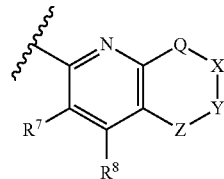

is selected from:

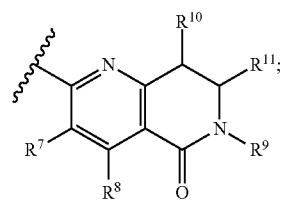

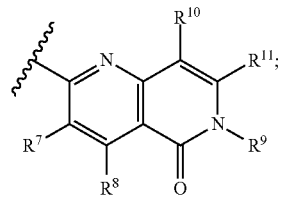

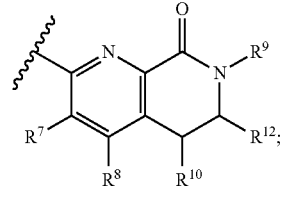

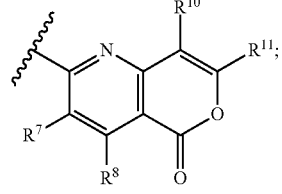

-continued

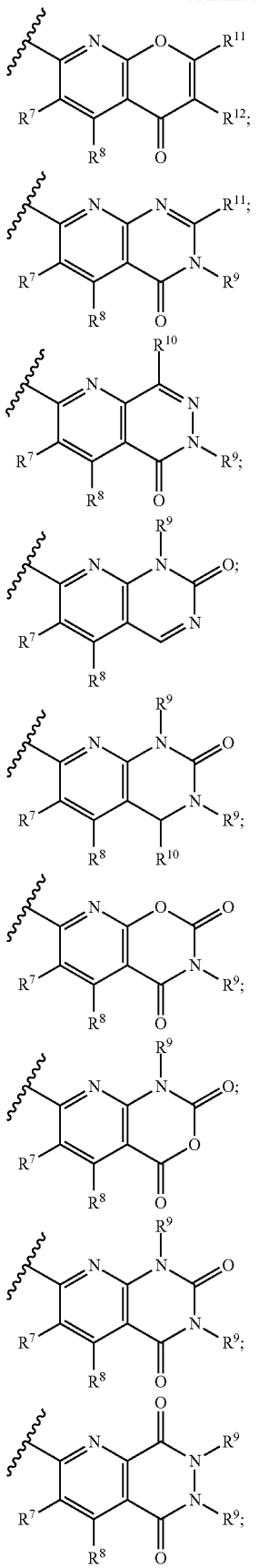

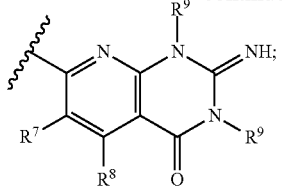

R¹ is selected from the group consisting of:
  (1) —C₁₋₆alkyl, which is unsubstituted or substituted with substituents selected from the group consisting of: hydroxy, fluoro, —CN, —O—C₁₋₆alkyl, and C₃₋₆cycloalkyl;
  (2) a phenyl, heteroaryl or heterocyclyl ring, wherein the phenyl, heteroaryl or heterocyclyl ring is substituted with one or more R$^{1a}$, R$^{1b}$ and R$^{1c}$, wherein R$^{1a}$, R$^{1b}$ and R$^{1c}$ are independently selected from the group consisting of:
    (a) hydrogen,
    (b) halogen,
    (c) C₁₋₆alkyl, which is unsubstituted or substituted with substituents selected from the group consisting of: hydroxy and fluoro,
    (d) —O—C₁₋₆alkyl,
    (e) C₃₋₆cycloalkyl, and
    (f) —CN;
R² and R³ are independently selected from the group consisting of:
  (1) hydrogen, and
  (2) fluoro;
R⁷ and R⁸ are independently selected from the group consisting of:
  (1) hydrogen, and
  (2) C₁₋₆alkyl;
R⁹ is selected from the group consisting of:
  (1) hydrogen,
  (2) —C₁₋₆alkyl, which is unsubstituted or substituted with substituents selected from the group consisting of: hydroxy, methoxy, fluoro, phenyl, or pyridyl;
each of R¹⁰, R¹¹ and R¹² is independently selected from the group consisting of:
  (1) hydrogen,
  (2) fluoro,
  (3) —OH,
  (4) —CH₃,
  (5) —CF₃,
  (6) —CH₂OH,
  (7) —CH₂CH₂OH,
  (8) —CH₂OCH₃, and
  (9) —CH₂CH₂OCH₃;
or a pharmaceutically acceptable salt thereof.

2. The compound of claim 1, or a pharmaceutically acceptable salt thereof, wherein R¹ is selected from the group consisting of: benzodioxolyl, benzoimidazolyl, benzoxazoly, benzooxazinone, benzooxazolone, benzothiazolyl, chromanyl, cyclopentapyridinyl, dihydrobenzo[1,4]dioxinyl, dihydrobenzofuranyl, dihydrobenzo[1,4]oxazinyl, dihydrofuropyridinyl, dihydroisobenzofuranyl, dihydroisoquinolinone, dihydropyranopyridinyl, dihydroimidazopyridine, dihydropyrido[1,4]oxazinyl, dihydroquinolinone, indazolyl, indanyl, indolyl, isochromanone, isobenzofuranone, isochromanyl, isoindolinyl, isoxazolyl, oxoisoindolinyl, phenyl, pyrazolopyridinyl, pyrazolyl, pyridyl, pyrrolopyridinyl, pyrimidinyl, quinolinone, quinolinyl, tetrahydrofuranyl, tetrahydroisoquinolinyl, tetrahydroquinolinyl, and tetrahydropyranyl, which is substituted with $R^{1a}$, $R^{1b}$ and $R^{1c}$.

3. The compound of claim 1, or a pharmaceutically acceptable salt thereof, wherein $R^1$ is phenyl or pyridyl, which is substituted with $R^{1a}$, $R^{1b}$ and $R^{1c}$, wherein $R^{1a}$, $R^{1b}$ and $R^{1c}$ are independently selected from the group consisting of
   (a) hydrogen,
   (b) halogen,
   (c) $C_{1-6}$alkyl, which is unsubstituted or substituted with substituents selected from the group consisting of: hydroxy and fluoro,
   (d) —O—$C_{1-6}$alkyl,
   (e) $C_{3-6}$cycloalkyl, and
   (f) —CN.

4. The compound of claim 1, or a pharmaceutically acceptable salt thereof, wherein $R^1$ is phenyl, which is unsubstituted or substituted with —CN.

5. The compound of claim 1, or a pharmaceutically acceptable salt thereof, wherein $R^1$ is pyridyl, which is unsubstituted or substituted with —$OCH_3$.

6. The compound of claim 1, or a pharmaceutically acceptable salt thereof, wherein $R^2$ is hydrogen and $R^3$ is hydrogen.

7. The compound of claim 1, or a pharmaceutically acceptable salt thereof, wherein $R^7$ is —$CH_3$.

8. The compound of claim 1, or a pharmaceutically acceptable salt thereof, wherein $R^8$ is hydrogen.

9. The compound of claim 1, or a pharmaceutically acceptable salt thereof, wherein $R^9$ is selected from the group consisting of:
   (1) hydrogen, and
   (2) —$C_{1-6}$alkyl, which is unsubstituted or substituted with hydroxy, methoxy, or 1-3 fluoro.

10. A compound which is selected from the group consisting of:
   2-(4-((6-methoxypyridin-3-yl)oxy)piperidin-1-yl)-3-methyl-7,8-dihydro-1,6-naphthyridin-5(6H)-one;
   6-(4-methoxybenzyl)-2-(4-((6-methoxypyridin-3-yl)oxy)piperidin-1-yl)-3-methyl-7,8-dihydro-1,6-naphthyridin-5(6H)-one;
   2-(4-((6-methoxypyridin-3-yl)oxy)piperidin-1-yl)-3-methyl-6-(pyridin-4-ylmethyl)-7,8-dihydro-1,6-naphthyridin-5(6H)-one;
   2-(4-((6-methoxypyridin-3-yl)oxy)piperidin-1-yl)-3,6-dimethyl-7,8-dihydro-1,6-naphthyridin-5(6H)-one;
   7-(4-((6-methoxypyridin-3-yl)oxy)piperidin-1-yl)-1,6-dimethylpyrido[2,3-d]pyrimidine-2,4(1H,3H)-dione;
   7-(4-((6-methoxypyridin-3-yl)oxy)piperidin-1-yl)-3,6-dimethylpyrido[2,3-d]pyrimidine-2,4(1H,3H)-dione;
   3-((1-(6-methyl-2,4-dioxo-1,2,3,4-tetrahydropyrido[2,3-d]pyrimidin-7-yl)piperidin-4-yl)oxy)benzonitrile;
   7-(4-((6-methoxypyridin-3-yl)oxy)piperidin-1-yl)-6-methylpyrido[2,3-d]pyrimidine-2,4(1H,3H)-dione;
   2-(hydroxymethyl)-7-(4-((6-methoxypyridin-3-yl)oxy)piperidin-1-yl)-6-methylpyrido[2,3-d]pyrimidin-4(3H)-one;
   7-(4-((6-methoxypyridin-3-yl)oxy)piperidin-1-yl)-6-methylpyrido[2,3-d]pyrimidin-4(3H)-one;
   2-(4-((6-methoxypyridin-3-yl)oxy)piperidin-1-yl)-3-methylpyrido[2,3-d]pyridazin-5(6H)-one;
   2-(4-((6-methoxypyridin-3-yl)oxy)piperidin-1-yl)-3-methyl-1,6-naphthyridin-5(6H)-one;
   2-(4-((6-methoxypyridin-3-yl)oxy)piperidin-1-yl)-3,6-dimethylpyrido[2,3-d]pyridazin-5(6H)-one;
   6-methyl-7-(4-phenoxypiperidin-1-yl)pyrido[2,3-d]pyrimidin-4(3H)-one;
   3-((1-(6-methyl-4-oxo-3,4-dihydropyrido[2,3-d]pyrimidin-7-yl)piperidin-4-yl)oxy)benzonitrile;
   6-methyl-7-(4-(pyridin-3-yloxy)piperidin-1-yl)pyrido[2,3-d]pyrimidin-4(3H)-one;
   7-(4-(cyclopropylmethoxy)piperidin-1-yl)-6-methylpyrido[2,3-d]pyrimidin-4(3H)-one;
   2-(4-(cyclopentylmethoxy)piperidin-1-yl)-3-methylpyrido[2,3-d]pyridazin-5 (6H)-one;
   7-(4-((6-methoxypyridin-3-yl)oxy)piperidin-1-yl)-2,6-dimethylpyrido[2,3-d]pyrimidin-4(3H)-one;
   2,6-dimethyl-7-(4-((1-methylcyclopropyl)methoxy)piperidin-1-yl)pyrido[2,3-d]pyrimidin-4(3H)-one;
   3-((1-(3-methyl-5-oxo-5,6-dihydropyrido[2,3-d]pyridazin-2-yl)piperidin-4-yl)oxy)benzonitrile;
   7-(4-((5,7-dihydrofuro[3,4-b]pyridin-3-yl)oxy)piperidin-1-yl)-2,6-dimethylpyrido[2,3-d]pyrimidin-4(3H)-one;
   3-methyl-2-(4-((1-methyl-1H-pyrazol-4-yl)oxy)piperidin-1-yl)pyrido[2,3-d]pyridazin-5 (6H)-one;
   3-methyl-2-(4-((1-methylcyclopropyl)methoxy)piperidin-1-yl)pyrido[2,3-d]pyridazin-5 (6H)-one;
   6-methyl-7-(4-((1-methylcyclopropyl)methoxy)piperidin-1-yl)pyrido[2,3-d]pyrimidine-2,4(1H,3H)-dione;
   6-methyl-7-(4-((1-methyl-1H-pyrazol-4-yl)oxy)piperidin-1-yl)pyrido[2,3-d]pyrimidine-2,4(1H,3H)-dione;
   2,6-dimethyl-7-(4-(1-methyl-1H-pyrazol-4-yl)oxy)piperidin-1-yl)pyrido[2,3-d]pyrimidin-4(3H)-one;
   2-(methoxymethyl)-7-(4-((6-methoxypyridin-3-yl)oxy)piperidin-1-yl)-6-methylpyrido[2,3-d]pyrimidin-4(3H)-one;
   2-(4-((5,7-dihydrofuro[3,4-b]pyridin-3-yl)oxy)piperidin-1-yl)-3-methylpyrido[2,3-d]pyridazin-5 (6H)-one;
   2-(2-methoxyethyl)-7-(4-((6-methoxypyridin-3-yl)oxy)piperidin-1-yl)-6-methylpyrido[2,3-d]pyrimidin-4(3H)-one;
   6-ethyl-7-(4-((1-methylcyclopropyl)methoxy)piperidin-1-yl)pyrido[2,3-d]pyrimidine-2,4(1H,3H)-dione;
   7-(4-(cyclobutylmethoxy)piperidin-1-yl)-6-methylpyrido[2,3-d]pyrimidine-2,4(1H,3H)-dione;
   7-(4-(cyclopropylmethoxy)piperidin-1-yl)-6-methylpyrido[2,3-d]pyrimidine-2,4(1H,3H)-dione;
   7-(4-(cyclohexylmethoxy)piperidin-1-yl)-6-methylpyrido[2,3-d]pyrimidine-2,4(1H,3H)-dione;
   7-(4-((6-methoxypyridin-3-yl)oxy)piperidin-1-yl)-6-methyl-4H-pyrano[2,3-b]pyridin-4-one;
   7-(4-isobutoxypiperidin-1-yl)-6-methylpyrido[2,3-d]pyrimidine-2,4(1H,3H)-dione;
   3-ethyl-2-(4-((6-methoxypyridin-3-yl)oxy)piperidin-1-yl)pyrido[2,3-d]pyridazin-5 (6H)-one;
   7-(4-(cyclopentylmethoxy)piperidin-1-yl)-6-methylpyrido[2,3-d]pyrimidine-2,4(1H,3H)-dione;
   3-((1-(2-(methoxymethyl)-6-methyl-4-oxo-3,4-dihydropyrido[2,3-d]pyrimidin-7-yl)piperidin-4-yl)oxy)benzonitrile;
   7-(4-((6-methoxypyridin-3-yl)oxy)piperidin-1-yl)-2,3,6-trimethylpyrido[2,3-d]pyrimidin-4(3H)-one;
   7-(4-((6-methoxypyridin-3-yl)oxy)piperidin-1-yl)-2,6-dimethyl-4H-pyrano[2,3-b]pyridin-4-one;
   6-(2-hydroxyethyl)-2-(4-((6-methoxypyridin-3-yl)oxy)piperidin-1-yl)-3-methylpyrido[2,3-d]pyridazin-5 (6H)-one;
   6-(2-hydroxyethyl)-3-methyl-2-(4-((1-methylcyclopropyl)methoxy)piperidin-1-yl)pyrido[2,3-d]pyridazin-5 (6H)-one;
   7-(4-((6-methoxypyridin-3-yl)oxy)piperidin-1-yl)-3,6-dimethylpyrido[2,3-d]pyrimidin-4(3H)-one;

7-(4-((5,7-dihydrofuro[3,4-b]pyridin-3-yl)oxy)piperidin-1-yl)-2,3,6-trimethylpyrido[2,3-d]pyrimidin-4(3H)-one;

2-(4-((6-methoxypyridin-3-yl)oxy)piperidin-1-yl)-3-methyl-6,7-dihydro-1,7-naphthyridin-8 (5H)-one;

7-(4-((6-methoxypyridin-3-yl)oxy)piperidin-1-yl)-6-methyl-2H-pyrido[2,3-d][1,3]oxazine-2,4(1H)-dione;

7-(4-((6-methoxypyridin-3-yl)oxy)piperidin-1-yl)-6-methyl-3,4-dihydropyrido[2,3-d]pyrimidin-2(1H)-one;

7-(4-((6-methoxypyridin-3-yl)oxy)piperidin-1-yl)-1,6-dimethylpyrido[2,3-d]pyrimidin-2(1H)-one;

2-imino-7-(4-((6-methoxypyridin-3-yl)oxy)piperidin-1-yl)-6-methyl-2,3-dihydropyrido[2,3-d]pyrimidin-4(1H)-one;

6-(hydroxymethyl)-2-(4-((6-methoxypyridin-3-yl)oxy)piperidin-1-yl)-3-methylpyrido[2,3-d]pyridazin-5(6H)-one;

7-(4-((6-methoxypyridin-3-yl)oxy)piperidin-1-yl)-6-methyl-2H-pyrido[3,2-e][1,3]oxazine-2,4(3H)-dione;

2-(4-((6-methoxypyridin-3-yl)oxy)piperidin-1-yl)-3-methyl-6,7-dihydropyrido[2,3-d]pyridazine-5,8-dione;

2-(4-((6-methoxypyridin-3-yl)oxy)piperidin-1-yl)-3-methyl-5H-pyrano[4,3-b]pyridin-5-one; and 2-(4-((6-methoxypyridin-3-yl)oxy)piperidin-1-yl)-3,7-dimethyl-5H-pyrano[4,3-b]pyridin-5-one;

or a pharmaceutically acceptable salt thereof.

11. A pharmaceutical composition which comprises an inert carrier and a compound of claim 1, or a pharmaceutically acceptable salt thereof.

12. A method for the treatment of schizophrenia in a mammal comprising the step of administering at least one compound of claim 1, or a pharmaceutically acceptable salt of said compound, to a patient in need thereof in an amount effective to treat said disorder.

13. The method of claim 12, wherein the mammal has been diagnosed with a need for treatment of schizophrenia prior to the administering step.

* * * * *